United States Patent
Beaudoin et al.

(10) Patent No.: US 12,012,433 B1
(45) Date of Patent: Jun. 18, 2024

(54) EXPRESSION AND PURIFICATION OF CAS ENZYMES

(71) Applicant: INTEGRATED DNA TECHNOLOGIES INC., Coralville, IA (US)

(72) Inventors: Sarah Franz Beaudoin, Iowa City, IA (US); Michael Allen Collingwood, North Liberty, IA (US); Christopher Anthony Vakulskas, North Liberty, IA (US); Mark Aaron Behlke, Coralville, IA (US)

(73) Assignee: INTEGRATED DNA TECHNOLOGIES INC., Coralville, IA (US)

(*) Notice: Subject to any disclaimer, the term of this patent is extended or adjusted under 35 U.S.C. 154(b) by 106 days.

(21) Appl. No.: 17/185,788

(22) Filed: Feb. 25, 2021

Related U.S. Application Data

(60) Provisional application No. 62/982,231, filed on Feb. 27, 2020.

(51) Int. Cl.
| | |
|---|---|
| *C07K 1/36* | (2006.01) |
| *C07K 1/18* | (2006.01) |
| *C07K 1/22* | (2006.01) |
| *C12N 9/22* | (2006.01) |

(52) U.S. Cl.
CPC .............. *C07K 1/36* (2013.01); *C07K 1/18* (2013.01); *C07K 1/22* (2013.01); *C12N 9/22* (2013.01); *C12Y 301/00* (2013.01)

(58) Field of Classification Search
CPC ... C07K 1/36; C07K 1/18; C07K 1/22; C12N 9/22; C12Y 301/00
See application file for complete search history.

(56) References Cited

U.S. PATENT DOCUMENTS

| | | | | |
|---|---|---|---|---|
| 7,560,529 | B2* | 7/2009 | Gabibov | C07K 16/1063 530/350 |
| 9,790,490 | B2* | 10/2017 | Zhang | C12N 15/82 |
| 9,840,702 | B2 | 12/2017 | Collingwood et al. | |
| 10,266,886 | B2* | 4/2019 | Abudayyeh | C12Q 1/68 |
| 10,717,978 | B2 | 7/2020 | Vakulskas et al. | |
| 10,767,176 | B2 | 9/2020 | Collingwood et al. | |
| 2016/0177304 | A1 | 6/2016 | Collingwood et al. | |
| 2016/0208243 | A1 | 7/2016 | Zhang et al. | |
| 2017/0044536 | A1 | 2/2017 | Collingwood et al. | |
| 2018/0179523 | A1 | 6/2018 | Collingwood et al. | |

(Continued)

FOREIGN PATENT DOCUMENTS

| | | |
|---|---|---|
| WO | 2017127807 A1 | 7/2017 |
| WO | 2017184768 A1 | 10/2017 |

(Continued)

OTHER PUBLICATIONS

Carmignotto et al., On the expression of recombinant Cas9 protein in *E. coli* BL21(DE3) and BL21(DE3) Rosetta strains, J Biotechnol. vol. 306:62-70 (epub Sep. 20, 2019) (Year: 2019).*

(Continued)

*Primary Examiner* — Randall L Beane
(74) *Attorney, Agent, or Firm* — Michael Best & Friedrich LLP

(57) ABSTRACT

Described herein are methods for the expression and purification of Cas13a and methods for detecting target RNA using Cas13a.

14 Claims, 4 Drawing Sheets

Specification includes a Sequence Listing.

(56) References Cited

U.S. PATENT DOCUMENTS

| | | |
|---|---|---|
| 2018/0187176 A1 | 7/2018 | Behlke et al. |
| 2018/0273938 A1 | 9/2018 | Turk et al. |
| 2018/0320201 A1 | 11/2018 | Vakulskas et al. |
| 2019/0010481 A1 | 1/2019 | Joung et al. |
| 2019/0032131 A1 | 1/2019 | Turk et al. |
| 2020/0080096 A1 | 3/2020 | Flasinski et al. |
| 2020/0109382 A1 | 4/2020 | Zhang et al. |

FOREIGN PATENT DOCUMENTS

| | | |
|---|---|---|
| WO | 2018195545 A2 | 10/2018 |
| WO | 2019138052 A1 | 7/2019 |
| WO | 2020172502 A1 | 8/2020 |
| WO | 20210937752 A1 | 5/2021 |
| WO | 2023097316 A1 | 6/2023 |

OTHER PUBLICATIONS

East-Seletsky et al., Two distinct RNase activities of CRISPR-C2c2 enable guide-RNA processing and RNA detection, Nature, vol. 538:270-273 and 13 pages of Supplemental Information (Oct. 2016) (Year: 2016).*

Evans et al., Concentration of proteins and removal of solutes, Methods Enzymol., vol. 463:97-120 (2009), PMID: 19892169 (Year: 2009).*

Francis et al., Strategies to Optimize Protein Expression in *E. coli.*, Current Protocols in Protein Science 5.24.1-5.24.29 (Aug. 2010) (Year: 2010).*

HiTrap Sp Hp cation exchange columns Protocol, SP Sepharose™ High Performance Ion Exchange Medium Instructions 18-1060-26-AG, GE Life Sciences, 20 pages (2014) (Year: 2014).*

Livingstone et al., Protein sequence alignments, CABIOS, vol. 9(6):745-756 (1993) (Year: 1993).*

PET System manual (Novagen, pET System Manual 10th Edition, 68 pages, published May 2003 (Year: 2003).*

Rodrigues et al, Chapter 5: One-Step Isothermal Assembly of DNA Fragments, Synthetic Biology, Methods in Molecular Biology, vol. 1073:43-47 (2013) (Year: 2013).*

Spriestersbach et al., Purification of His-Tagged Proteins, Methods Enzymol., vol. 559:1-15, PMID: 26096499 (Epub May 4, 2015) (Year: 2015).*

International Search Report and Written Opinion for Application No. PCT/US2021/030089 dated May 20, 2022 (25 pages).

Studer, R.A. et al. "Residue mutations and their impact on protein structure and function: detecting beneficial and pathogenic changes." Biochemical journal 449.3 (2013): 581-594.

Australian Patent Office Examination Report No. 1 for application 2020226864, dated Jan. 19, 2023 (4 pages).

Canadian Patent Office Action for application 3,130,087, dated Nov. 24, 2022 (6 pages).

Abudayyeh et al., "C2c2 is a single component programmable RNA-guided RNA-targeting CRISPR effector", Science, vol. 353(6299), 2016.

Bowie et al., "Deciphering the Message in Protein Sequences: Tolerance to Amino Acid Substitutions", Science, vol. 247, 1990, pp. 1306-1310.

East-Seletsky et al., "Two distinct RNase activities of CRISPR-C2c2 enable guide-RNA processing and RNA detection", Nature, vol. 538 (7624), 2016, pp. 270-273.

Gao et al., "Engineered Cpf1 variants with altered PAM specificities increase genome targeting range", Nat Biotechnol., vol. 35, No. 8, 2017, pp. 789-792.

Gao et al., "Type V CRISPR-Cas Cas12a endonuclease employs a unique mechanism for crRNA-mediated target DNA recognition," Cell Research, vol. 26, 2016, pp. 901-913.

Gibson et al., "Enzymatic assembly of DNA molecules up to several hundred kilobases", Nature Methods, vol. 5, No. 5, 2009, pp. 343-34.

Gootenberg et al., "Nucleic acid detection with CRISPR-Cas13a/C2c2" Science, vol. 356(6336), 2017, pp. 438-442.

Hur et al., "Targeted mutagenesis in mice by electroporation of Cpf1 ribonucleoproteins," Nature Biotechnology 34(8):807-808 (2016).

International Search Report and Written Opinion for Application No. PCT/US2020/19168 dated Jul. 23, 2020 (13 pages).

Jinek et al., "A programmable dual-RNA-guided DNA endonuclease in adaptive bacterial 5 immunity", Science, vol. 337, 2012, pp. 816-821.

Kim et al., "CRISPR/Cpf1-mediated DNA-free plant genome editing," Nature Commun., vol. 8(14406), 2017, pp. 1-7.

Kim et al., "Generation of knockdown mice by Cpf1-mediated gene targeting," Nature Biotechnology, vol. 34, No. 8, 2016, pp. 808-810.

Kim et al., "In vivo high-throughput profiling of CRISPR-Cpf1 activity," Nature Methods, vol. 14, No. 2, 2017, pp. 153-159.

Kleinstiver et al., "Engineered CRISPR-Cas 12a variants with increased activities and improved targerting ranges for gene, epigenetic and base editing", Nat. Biotechnol., vol. 37, 2019, pp. 276-282.

Kleinstiver et al., "Genome-wide specificities of CRISPR-Cas Cpf1 nucleases in human cells," Nature Biotechnology, vol. 34, No. 8, 2016, pp. 869-874.

Schindele et al., "Engineering CRISPR/LbCas12a for highly efficient, temperature tolerant plant gene editing", Plant Biotechnol J., vol. 18, No. 5, 2020, pp. 1118-1120.

Wrenbeck et al., "Plasmid-based one-pot saturation mutagenesis", Nat Methods, vol. 13, 2016, pp. 928-930.

Yamano et al., "Crystal Structure of Cpf1 in Complex with Guide RNA and Target RNA," Cell vol. 65, 2016, pp. 949-962.

Zetsche et al., "Cpf1 Is a Single RNA-Guided Endonuclease of a Class 2 CRISPR-Cas System", Cell, vol. 163, 2015, pp. 759-771.

Zetsche et al., "Multiplex gene editing by CRISPR-Cpf1 using a single rRNA array," Nature Biotechnology, vol. 35, No. 1, 2017, pp. 31-34.

Cebrian-Serrano et al., "CRISPR-Cas orthologues and variants: optimizing the repertoire, specificity and delivery of genome engineering tools", Mammalian Genome, 2017, vol. 28, No. 7, pp. 247-261.

Geneseq, "Lachnospiraceae bacterium Cpf1 gene (PL-LbCpf1-RR) encoded nuclease", Nov. 2017, EBI Accession No. GS_PROT:BEK39676, 1 pages.

Japanese Patent Office Notification of Reasons for Rejection for Application No. 2021-548687, dated Aug. 4, 2023, 14 pages with translation.

Chinese Patent Office Notification of First Office Action for Application No. 202080015167.9, dated Sep. 27, 2023, 17 pages with translation.

Lu Yifan et al., LbCpf1 "Prokaryotic Expression, Purification of LbCpf1 Protein Gene and in Vitro Cleavage Activity Assay." China Biotechnology 40.8 (2020): 41-48. With English Abstract.

Zhang, Y., et al. "Highly efficient genome editing in plant protoplasts by ribonucleoprotein delivery of CRISPR-Cas12a nucleases." Frontiers in Genome Editing 4 (2022): 780238.

Australian Patent Office Examination Report No. 2 for Application No. 2020226864, dated Jun. 26, 2023 (9 pages).

Yamano T., et al., "Structural basis for the canonical and non-canonical PAM recognition by CRISPR-Cpf1." Molecular cell 67.4 (2017): 633-645.

European Patent Office Extended European Search Report for Application No. 20760344.0, dated Feb. 26, 2024 (8 pages).

Canadian Patent Office Action for application 3,130,087, dated Feb. 19, 2024 (3 pages).

"SEQ ID No. 3 vs SEQ ID No. 109" Downloaded from <https://blast.ncbi.nlm.nih.gov/Blast.cgi> Apr. 3, 2024. (Year: 2016) (2 pages).

"SEQ ID No. 6 vs SEQ ID No. 109" Downloaded from <https://blast.ncbi.nlm.nih.gov/Blast.cgi> Apr. 3, 2024. (Year: 2016) (2 pages).

* cited by examiner

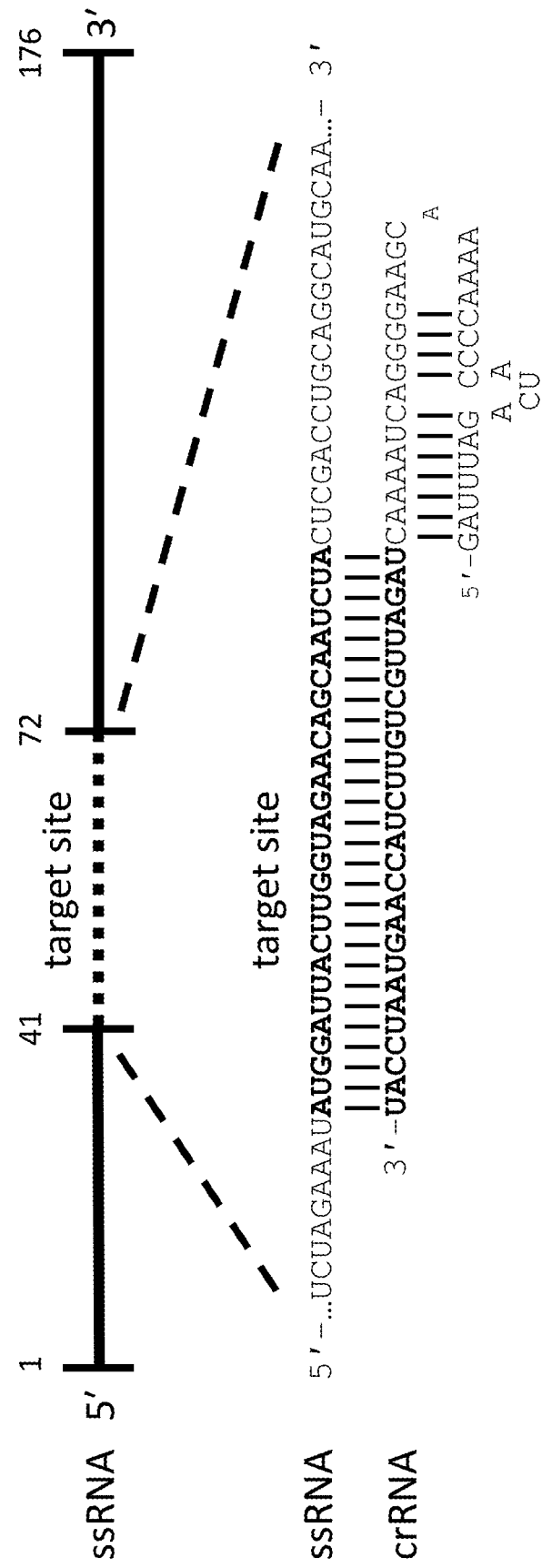

EXPRESSION AND PURIFICATION OF CAS ENZYMES

CROSS-REFERENCE TO RELATED APPLICATIONS

This application claims priority to U.S. Provisional Patent Application No. 62/982,231 filed on Feb. 27, 2020, which is incorporated by reference herein in its entirety.

REFERENCE TO SEQUENCE LISTING

This application is filed with a Computer Readable Form of a Sequence Listing in accordance with 37 C.F.R. § 1.821(c). The text file submitted by EFS, "013670-9065-US02_sequence_listing_25 Feb. 2021_ST25," was created on Feb. 25, 2021, contains 44 sequences, has a file size of 226 Kbytes, and is hereby incorporated by reference in its entirety.

TECHNICAL FIELD

Described herein are methods for the expression and purification of Cas13a and methods for detecting target RNA using Cas13a.

BACKGROUND

The RNA targeting enzyme family Cas13 is a CRISPR system identified in an effort to identify new CRISPR systems in addition to Cas9 and Cas12a (also referred to as Cpf1). Cas13 has four subtypes (Cas13a-d) and Cas13a (formerly known as C2c2) is a single effector protein that lacks homology with any known DNA nuclease; however, the protein contains two Higher Eukaryotes and Prokaryotes Nucleotide-binding (HEPN) domains that more commonly function as ribonucleases (RNases). Abudayyeh et al., demonstrated that Cas13a could act as an RNA-directed RNase [1].

Cas13a is classified as a class 2 type VI Clustered Regularly Interspaced Short Palindromic Repeat (CRISPR) adaptive immune system protein that provides direct cleavage of RNA when complexed with a CRISPR RNA (crRNA). This complex is called a CRISPR ribonucleoprotein (RNP) complex. Once the Cas13a RNP recognizes and cleaves its RNA target, the protein engages in collateral cleavage of nonspecific RNAs. For this reason, Cas13a can provide specific RNA sensing in vitro by utilizing its non-specific RNase activity in the degradation of fluorescent-labeled RNA. This system has led to the rapid and inexpensive detection of nucleic acids by Cas13a and can be applied in disease diagnostics and epidemiology by detecting single RNA molecules with high specificity.

A method for nucleic acid detection by Cas13a RNP is described by Gootenberg et al., using *Leptotrichia wadei* (Lwa) Cas13a and denoted as SHERLOCK (Specific High Sensitivity Enzymatic Reporter UnLOCKing) [2]. Gootenberg et al. describe LwaCas13a as a superior protein over both *Leptotrichia buccalis* (Lbu) and *Leptotrichia shahii* (Lsh) species, as it yields detection sensitivity of approximately 50 fM. They surveyed the applications of the SHERLOCK technology towards infectious diseases, bacterial pathogens, low frequency cancer mutations in cell free DNA fragments, among others. For instance, they could discriminate between the Zika virus and the related flavivirus, Dengue, down to 2 aM. The SHERLOCK technology is a sensitive nucleic acid detection that can easily be applied for field applications.

The purification of LwaCas13a, as described by Gootenberg et al., consists of four purification steps: affinity chromatography, followed by removal of the 6×His/Twin Strep by SUMO digestion, cation exchange chromatography and finally, gel filtration chromatography [2].

What is needed is a simplified process for the expression and purification of Cas13 proteins.

SUMMARY

One embodiment described herein is a method for expressing and purifying a Cas13a protein, the method comprising: (a) inserting a nucleotide sequence encoding polypeptides having 95-99% identity to polypeptide sequences of SEQ ID NO: 2, 4, 6, 8, 10, 12, or 14 into an expression plasmid; (b) transforming one or more cells with the expression plasmid; (c) inducing expression of the transformed plasmid; (d) isolating the cells; (e) extracting the Cas13a protein; and (f) purifying the protein using affinity purification and ion exchange purification. In one aspect, the Cas13a protein comprises one or more of *Leptotrichia buccalis* (Lbu), *Leptotrichia shahii* (Lsh), and *Leptotrichia wadei* (Lwa) Cas13a proteins, or mutants thereof. In another aspect, the nucleotide sequence has 90-99% identity to SEQ ID NO: 1, 3, 5, 7, 9, 11, or 13. In another aspect, the nucleotide sequence is selected from SEQ ID NO: 1, 3, 5, 7, 9, 11, or 13. In another aspect, the encoded polypeptides are selected from SEQ ID NO: 2, 4, 6, 8, 10, 12, or 14. In another aspect, the cell comprises *E. coli* BL21(DE3). In another aspect, the expression plasmid comprises pET28 or pET28-MBP-TEV plasmids. In another aspect, the nucleotide sequence is inserted into the expression plasmid using isothermal assembly. In another aspect, the affinity purification comprises a nickel or a maltose affinity media.

In one aspect, the affinity purification comprises affinity chromatography comprising: (a) equilibrating a nickel affinity column with a binding buffer and loading the extracted Cas13a protein; (b) washing the nickel affinity column with a wash buffer; and (c) eluting the affinity purified Cas13a protein from the nickel affinity column using an elution buffer.

In one aspect, the affinity purification comprises affinity chromatography comprising: (a) equilibrating a maltose affinity column with a binding buffer and loading the extracted Cas13a protein; (b) washing the maltose affinity column with a wash buffer; and (c) eluting the affinity purified Cas13a protein from the maltose affinity column using an elution buffer. In another aspect, the ion exchange purification comprises a cation exchange media.

In one aspect, the ion exchange purification comprises cation exchange chromatography comprising: (a) equilibrating a cation exchange column with a binding buffer and loading the extracted Cas13a protein; (b) washing the cation exchange column with a wash buffer; and (c) eluting the cation exchange purified Cas13a protein from the cation exchange column using an elution buffer. In another aspect, the method further comprises concentrating the purified Cas13a protein to approximately 10 mg/mL. In another aspect, the method further comprises dialyzing the concentrated purified Cas13a protein.

Another embodiment described herein is a method for purifying a recombinant Cas13a protein, the method comprising: (a) providing an expressed recombinant Cas13a protein having 95-99% identity to the polypeptide sequences of SEQ ID NO: 2, 4, 6, 8, 10, 12, or 14; (b) performing an affinity purification comprising a nickel affinity media; (c) performing an affinity purification comprising maltose affinity media; (d) performing an ion exchange purification comprising a cation exchange media; and (e) collecting the purified Cas12 protein. In another aspect, the Cas13a proteins are encoded by a nucleotide sequence having 90-99% to SEQ ID NO: 1, 3, 5, 7, 9, 11, or 13. In another aspect, the Cas13a proteins are encoded by a nucleotide sequence of SEQ ID NO: 1, 3, 5, 7, 9, 11, or 13. In another aspect, the Cas13a proteins are selected from polypeptide sequences of SEQ ID NO: 2, 4, 6, 8, 10, 12, or 14. In another aspect, the method further comprises comprising concentrating the purified Cas13a protein to approximately 10 mg/mL. In another aspect, the method further comprises dialyzing the concentrated purified Cas13a protein against three rounds of dialysis buffer.

Another embodiment described herein is a nucleic acid detection system comprising: a Cas13a protein; one or more guide RNA designed to hybridize to a corresponding target nucleic acid; and a degradation reporter probe. In one aspect, the Cas13a protein is selected from the group comprising Lwa Cas13a, Lbu Cas13a, or Lsh Cas13a. In another aspect, the Lwa Cas13a or Lbu Cas13a is present at a concentration of 0.98 nM to 1000 nM. In another aspect, the Lbu Cas13a is present at a concentration of 0.98 nM to 1000 nM. In another aspect, the Lbu Cas13a is present at a concentration of 3.91 nM to 31.3 nM. In another aspect, the degradation reporter probe is fluorescently labeled.

Another embodiment described herein is a method of detecting a target nucleic acid comprising: (a) providing a Cas13a protein; (b) one or more guide RNA designed to hybridize to a corresponding target nucleic acid; and (c) a degradation reporter probe; wherein the Cas13a protein is present at an effective concentration to promote cleavage of the corresponding target nucleic acid and the degradation reporter probe to generate a detectable signal. In one aspect, the detectable signal is a fluorescent signal.

BRIEF DESCRIPTION OF THE DRAWINGS

FIG. 2A shows the nucleic acid target sequence with the complementery sequence bolded.

FIG. 2B shows the nucleic acid target and crRNA interactions (bold).

DETAILED DESCRIPTION

Figure 1:
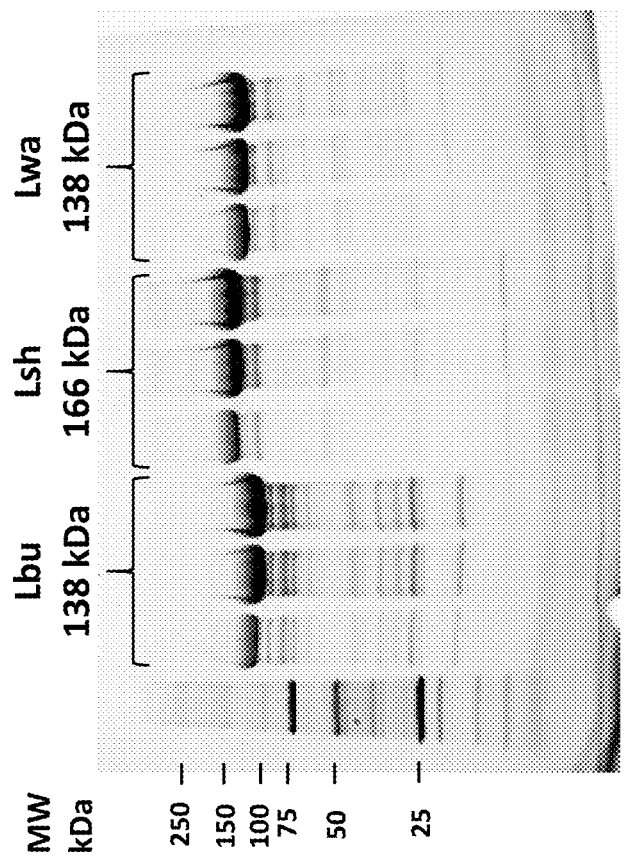
FIG. 1 shows an SDS-PAGE indicating the purity of Cas13a variants after the final step in purification and dialysis into storage buffer.

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present document, including definitions, will control. Representative compositions, methods, and materials are described herein, although equivalent materials and methods can be used in practice.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "-" means "about" or "approximately." All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

The methods and compositions escribed herein can be used with any CRISPR system wherein the Cas nuclease targets RNA. In one embodiment, the methods described herein utilize Cas13 enzyme. In another embodiment the Cas13 enzyme is a Cas13a subtype. There are two distinct subfamilies of the Cas13a protein family, adenosine (A) or uridine (U) cleaving. In another embodiment described herein, the methods utilize a LbuCas13a, a single effector RNA-directed RNase, an example being a LbuCas13a from the *Leptotrichia buccalis* CRISPR adaptive immune system, which resides in the uridine (U) cleaving subfamily of Cas13a proteins. The ability of LbuCas13a to act as a non-specific RNase was described by East-Seletsky et al. and showed that this class of enzymes is capable of two RNA cleavage activities: crRNA-mediated cleavage of target RNA, followed by non-specific RNase activity [3].

The purification of Cas13a has been described by both Gootenberg et al. [2], and East-Seletsky et al. [3] and consists of four purification steps each. Gootenberg et al. [2] describes the overexpression of LwaCas13a from a pET SUMO expression plasmid. The purification begins with affinity chromatography by StrepTactin® Sepharose (IBL Lifescieneces), followed by removal of the 6×His/Twin Strep by SUMO digestion. The native protein is further purified by cation exchange chromatography (HiTrap™ SP HP) and gel filtration chromatography (Superdex®200).

The purification described by East-Seletsky et al. [3] uses a similar procedure, except that LbuCas13a is N-terminally expressed with a 6×His-MBP-TEV tag. The purification procedure consists of affinity chromatography, removal of 6×His-MBP by TEV protease, cation exchange chromatography with a HiTrap™ SP column (Cytiva) and gel filtration chromatography (Superdex® 200).

The methods described herein simplify the purification process by only using two steps: affinity chromatography and cation exchange chromatography. The purification protocol leaves the 6×HisTag (CTD) intact while not sacrificing activity. Unlike previous methods which use 45 nM purified LwaCas13a with 22.5 nM crRNA to form the RNP complex, the current method utilizes LbuCas13a and a 10-fold reduction of purified protein (4 nM) with an equal concentration of crRNA.

One embodiment described herein is a method for expressing and purifying a Cas13a protein, the method comprising: (a) inserting a nucleotide sequence encoding polypeptides having 95-99% identity to polypeptide sequences of SEQ ID NO: 2, 4, 6, 8, 10, 12, or 14 into an expression plasmid; (b) transforming one or more cells with the expression plasmid; (c) inducing expression of the transformed plasmid; (d) isolating the cells; (e) extracting the Cas13a protein; and (f) purifying the protein using affinity purification and ion exchange purification. In one aspect, the Cas13a protein comprises one or more of *Leptotrichia buccalis* (Lbu), *Leptotrichia shahii* (Lsh), and *Leptotrichia wadei* (Lwa) Cas13a proteins, or mutants thereof. In another aspect, the nucleotide sequence has 90-99% identity to SEQ ID NO: 1, 3, 5, 7, 9, 11, or 13. In another aspect, the nucleotide sequence is selected from SEQ ID NO: 1, 3, 5, 7, 9, 11, or 13. In another aspect, the encoded polypeptides are selected from SEQ ID NO: 2, 4, 6, 8, 10, 12, or 14. In another aspect, the cell comprises *E. coli* BL21(DE3). In another aspect, the expression plasmid comprises pET28 or pMAL plasmids. In another aspect, the nucleotide sequence is inserted into the expression plasmid using isothermal assembly. In another aspect, the affinity purification comprises a nickel or a maltose affinity media.

In one aspect, the affinity purification comprises affinity chromatography comprising: (a) equilibrating a nickel affinity column with a binding buffer and loading the extracted Cas13a protein; (b) washing the nickel affinity column with a wash buffer; and (c) eluting the affinity purified Cas13a protein from the nickel affinity column using an elution buffer.

In one aspect, the affinity purification comprises affinity chromatography comprising: (a) equilibrating a maltose affinity column with a binding buffer and loading the extracted Cas13a protein; (b) washing the maltose affinity column with a wash buffer; and (c) eluting the affinity purified Cas13a protein from the maltose affinity column using an elution buffer. In another aspect, the ion exchange purification comprises a cation exchange media.

In one aspect, the ion exchange purification comprises cation exchange chromatography comprising: (a) equilibrating a cation exchange column with a binding buffer and loading the extracted Cas13a protein; (b) washing the cation exchange column with a wash buffer; and (c) eluting the cation exchange purified Cas13a protein from the cation exchange column using an elution buffer. In another aspect, the method further comprises concentrating the purified Cas13a protein to approximately 10 mg/mL. In another aspect, the method further comprises dialyzing the concentrated purified Cas13a protein.

Another embodiment described herein is a method for purifying a recombinant Cas13a protein, the method comprising: (a) providing an expressed recombinant Cas13a protein having 95-99% identity to the polypeptide sequences of SEQ ID NO: 2, 4, 6, 8, 10, 12, or 14; (b) performing an affinity purification comprising a nickel affinity media; (c) performing an affinity purification comprising maltose affinity media; (d) performing an ion exchange purification comprising a cation exchange media; and (e) collecting the purified Cas12 protein. In another aspect, the Cas13a proteins are encoded by a nucleotide sequence having 90-99% to SEQ ID NO: 1, 3, 5, 7, 9, 11, or 13. In another aspect, the Cas13a proteins are encoded by a nucleotide sequence of SEQ ID NO: 1, 3, 5, 7, 9, 11, or 13. In another aspect, the Cas13a proteins are selected from polypeptide sequences of SEQ ID NO: 2, 4, 6, 8, 10, 12, or 14. In another aspect, the method further comprises comprising concentrating the purified Cas13a protein to approximately 10 mg/mL. In another aspect, the method further comprises dialyzing the concentrated purified Cas13a protein against three rounds of dialysis buffer.

Another embodiment described herein is a nucleic acid detection system comprising: a Cas13a protein; one or more guide RNA designed to hybridize to a corresponding target nucleic acid; and a degradation reporter probe. In one aspect, the Cas13a protein is selected from the group comprising Lwa Cas13a, Lbu Cas13a, or Lsh Cas13a. In another aspect, the Lwa Cas13a or Lbu Cas13a is present at a concentration of 0.98 nM to 1000 nM. In another aspect, the Lbu Cas13a is present at a concentration of 0.98 nM to 1000 nM. In another aspect, the Lbu Cas13a is present at a concentration of 3.91 nM to 31.3 nM. In another aspect, the degradation reporter probe is fluorescently labeled.

Another embodiment described herein is a method of detecting a target nucleic acid comprising: (a) providing a Cas13a protein; (b) one or more guide RNA designed to hybridize to a corresponding target nucleic acid; and (c) a degradation reporter probe; wherein the Cas13a protein is present at an effective concentration to promote cleavage of the corresponding target nucleic acid and the degradation reporter probe to generate a detectable signal. In one aspect, the detectable signal is a fluorescent signal.

Another embodiment described herein is a polynucleotide vector comprising one or more nucleotide sequences described herein.

Another embodiment described herein is a cell comprising one or more nucleotide sequences described herein or a polynucleotide vector described herein.

Another embodiment is a polypeptide encoded by a nucleotide sequence described herein. In one aspect, the polypeptide has 85% to 99% identity to SEQ ID NO: 2, 4, 6, 8, 10, 12, or 14. In another aspect, the polypeptide is selected from SEQ ID NO: 2, 4, 6, 8, 10, 12, or 14.

Another embodiment described herein is a process for manufacturing one or more of the nucleotide sequence described herein or a polypeptide encoded by the nucleotide sequence described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence of described herein; isolating the polypeptide encoded by a nucleotide described herein.

Another embodiment described herein is a means for manufacturing one or more of the nucleotide sequences described herein or a polypeptide encoded by a nucleotide sequence described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence of described herein; isolating the polypeptide encoded by a nucleotide described herein.

Another embodiment described herein is a nucleotide sequence or a polypeptide encoded by the nucleotide sequence produced by the method or the means described herein.

Another embodiment described herein is the use of an effective amount of a polypeptide encoded by one or more of the nucleotide sequences described herein in SEQ ID NO: 1, 3, 5, 7, 9, 11, or 13.

Another embodiment described herein is a research tool comprising a polypeptide encoded by a nucleotide sequence described herein.

Another embodiment described herein is a reagent comprising a polypeptide encoded by a nucleotide sequence described herein.

The polynucleotides described herein include variants that have substitutions, deletions, and/or additions that can involve one or more nucleotides. The variants can be altered in coding regions, non-coding regions, or both. Alterations in the coding regions can produce conservative or non-conservative amino acid substitutions, deletions, or additions. Especially preferred among these are silent substitutions, additions, and deletions, which do not alter the properties and activities of the binding.

Further embodiments described herein include (a) nucleotide sequences about 50%, 55%, 60%, 65%, 70%, 75%, 80%, 85%, 90%, 91%, 92%, 93%, 94%, 95%, 96%, 97%, 98%, or 99% identical, and more preferably at least about 90-99% or 100% identical to nucleotide sequences encoding polypeptide SEQ ID NO: 2, 4, 6, 8, 10, 12, or 14; (b) nucleotide sequences, or degenerate, homologous, or codon-optimized variants thereof, encoding polypeptides having the amino acid sequences in SEQ ID NO: 2, 4, 6, 8, 10, 12, or 14; and (c) nucleotide sequences capable of hybridizing to the complement of any of the nucleotide sequences in (a) or (b) above and capable of expressing functional polypeptides of amino acid sequences in SEQ ID NO: 2, 4, 6, 8, 10, 12, or 14.

By a polynucleotide having a nucleotide sequence at least, for example, 90-99% "identical" to a reference nucleotide sequence encoding a Cas13 protein is intended that the nucleotide sequence of the polynucleotide be identical to the reference sequence except that the polynucleotide sequence can include up to about 10 to 1 point mutations, additions, or deletions per each 100 nucleotides of the reference nucleotide sequence encoding the Cas13 protein.

In other words, to obtain a polynucleotide having a nucleotide sequence about at least 90-99% identical to a reference nucleotide sequence, up to 10% of the nucleotides in the reference sequence can be deleted, added, or substituted, with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence. The same is applicable to polypeptide sequences about at least 90-99% identical to a reference polypeptide sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* 2: 4 82-489 (1981). This algorithm can be extended to use with peptide sequences using the scoring matrix developed by Dayhoff, *Atlas of Protein Sequences and Structure*, M. O. Dayhoff ed., 5 suppl. 3: 353-358, National Biomedical Research Foundation, Washington, D.C., USA, and normalized by Gribskov, *Nucl. Acids Res.* 14(6): 6745-6763 (1986).

For example, due to the degeneracy of the genetic code, one having ordinary skill in the art will recognize that a large number of the nucleic acid molecules having a sequence at least 50%, 55%, 60%, 65%, 70%, 75%, 80%, 85%, 90%, 91%, 92%, 93%, 94%, 95%, 96%, 97%, 98%, 99%, or 100% identical to the nucleic acid sequence shown in SEQ ID NO: 1, 3, 5, 7, 9, 11, or 13, or degenerate, homologous, or codon-optimized variants thereof, will encode a Cas13 protein.

The polynucleotides described herein include those encoding mutations, variations, substitutions, additions, deletions, and particular examples of the polypeptides described herein. For example, guidance concerning how to make phenotypically silent amino acid substitutions is provided in Bowie, J. U. et al., "Deciphering the Message in Protein Sequences: Tolerance to Amino Acid Substitutions," *Science* 247: 1306-1310 (1990), wherein the authors indicate that proteins are surprisingly tolerant of amino acid substitutions.

Thus, fragments, derivatives, or analogs of the polypeptides of SEQ ID NO: 2, 4, 6, 8, 10, 12, or 14 can be (i) ones in which one or more of the amino acid residues (e.g., 1, 2, 3, 4, 5, 7, 8, 9, 10, 11, 12, 13, 14, 15, 16, 17, 18, 19, 20, 25, 30, 35, 40, 45, or 50 residues, or even more) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 1, 2, 3, 4, 5, 7, 8, 9, 10, 15, 20, 25, 30, 35, 40, 45, or 50 residues or even more), or (iii) ones in which the mature polypeptide is fused with another polypeptide or compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives, and analogs are deemed to be within the scope of those skilled in the art from the teachings herein.

In addition, fragments, derivatives, or analogs of the polypeptides of SEQ ID NO: 2, 4, 6, 8, 10, 12, or 14 can be substituted with one or more conserved or non-conserved amino acid residue (preferably a conserved amino acid residue). In some cases these polypeptides, fragments, derivatives, or analogs thereof will have a polypeptide sequence at least 50%, 55%, 60%, 65%, 70%, 75%, 80%, 85%, 90%, 91%, 92%, 93%, 94%, 95%, 96%, 97%, 98%, 99% or 100% identical to the polypeptide sequence shown in SEQ ID NO: 2, 4, 6, 8, 10, 12, or 14 and will comprise functional or non-functional proteins or enzymes. Similarly, additions or deletions to the polypeptides can be made either at the N- or C-termini or within non-conserved regions of the polypeptide (which are assumed to be non-critical because they have not been photogenically conserved).

As described herein, in many cases the amino acid substitutions, mutations, additions, or deletions are preferably of a minor nature, such as conservative amino acid substitutions that do not significantly affect the folding or activity of the protein or additions or deletions to the N- or C-termini. Of course, the number of amino acid substitutions, additions, or deletions a skilled artisan would make depends on many factors, including those described herein. Generally, the number of substitutions, additions, or deletions for any given polypeptide will not be more than about 100, 90, 80, 70, 60, 50, 40, 30, 25, 20, 19, 18, 17, 16, 15, 14, 13, 12, 11, 10, 9, 8, 7, 5, 6, 4, 3, 2, or 1.

It will be apparent to one of ordinary skill in the relevant art that suitable modifications and adaptations to the compositions, formulations, methods, processes, apparata, assemblies, and applications described herein can be made without departing from the scope of any embodiments or aspects thereof. The compositions, apparata, assemblies, and methods provided are exemplary and are not intended to limit the scope of any of the disclosed embodiments. All the various embodiments, aspects, and options disclosed herein can be combined in any variations or iterations. The scope of the compositions, formulations, methods, apparata, assemblies, and processes described herein include all actual or potential combinations of embodiments, aspects, options, examples, and preferences described herein. The compositions, formulations, apparata, assemblies, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

REFERENCES

1. Abudayyeh et al., "C2c2 is a single-component programmable RNA-guided RNA-targeting CRISPR effector," *Science* 353(6299): aaf5573 (2016).
2. Gootenberg et al., "Nucleic acid detection with CRISPR-Cas13a/C2c2," *Science* 356(6336): 438-442 (2017).
3. East-Seletsky et al., "Two distinct RNase activities of CRISPR-C2c2 enable guide-RNA processing and RNA detection," *Nature* 538 (7624): 270-273 (2016).
4. Gibson et al., "Enzymatic assembly of DNA molecules up to several hundred kilobases," *Nature Methods* 6 (5): 343-34 (2009).

EXAMPLES

Example 1

Three Cas13a variants from *Leptotrichia buccalis* (Lbu), *Leptotrichia shahii* (Lsh), and *Leptotrichia wadei* (Lwa) were overexpressed in *E. coli* cells and purified from lysates thereof. See Table 1. The genes encoding the Lbu, Lsh, and Lwa Cas13a variants were synthesized as gBlocks® Gene Fragments (Integrated DNA Technologies) and inserted into pET28b (SEQ ID NO: 43) and pET28-MBP-TEV (SEQ ID NO: 44) expression plasmids by isothermal assembly of DNA fragments (see [4]) (Table 2). All primers were manufactured by Integrated DNA Technologies Inc.

TABLE 1

Polynucleotide and Polypeptide Sequences of Cas Constructs

LbuCas13a CTD-His Polynucleotide Sequence

SEQ ID NO: 1

```
ATGAAGGTGACCAAAGTTGGTGGTATCAGCCATAAAAAGTATACCAGCGAAGGTCGTCTGGTTAAAAGCGAAAGCG
AAGAAAATCGTACCGATGAACGTCTGAGCGCACTGCTGAATATGCGTCTGGATATGTATATCAAAAATCCGAGCAG
CACCGAAACCAAAGAAAATCAGAAACGTATCGGCAAGCTGAAAAAGTTCTTCAGCAACAAAATGGTGTACCTGAAA
GATAACACCCTGAGCCTGAAAAACGGCAAGAAAGAAAATATCGATCGCGAGTATAGCGAAACCGATATTCTGGAAA
GTGATGTGCGTGACAAAAAAACTTTGCCGTCCTGAAAAAGATCTATCTGAACGAAAATGTGAACAGCGAAGAACT
GGAAGTGTTTCGCAACGACATTAAAAAGAAGCTGAACAAGATCAACAGCCTGAAATATAGCTTCGAGAAAAACAAA
GCCAACTATCAGAAGATCAACGAGAACAACATCGAAAAGTGGAAGGTAAAAGCAAGCGCAACATCATCTATGATT
ATTATCGTGAAAGCGCCAAACGTGATGCCTATGTTAGCAATGTTAAAGAGGCCTTCGACAAGCTGTATAAAGAAGA
AGATATTGCCAAACTGGTGCTGGAAATTGAAAATCTGACCAAGCTGGAAAAATACAAGATCCGCGAATTCTATCAC
GAAATCATTGGTCGCAAAAACGATAAAGAGAACTTCGCCAAAATCATCTACGAAGAAATTCAGAACGTGAATAACA
TGAAAGAACTGATCGAGAAAGTTCCGGATATGAGCGAACTGAAAAAAAGCCAGGTGTTCTACAAATATTACCTGGA
CAAAGAGGAACTGAACGATAAAAACATCAAATACGCCTTTTGCCACTTCGTGGAAATCGAAATGAGCCAGCTGCTG
AAAAACTATGTGTATAAACGCCTGAGCAACATCAGCAACGATAAGATTAAACGCATCTTCGAGTACCAGAACCTGA
AGAAACTGATTGAAAACAAACTGCTTAACAAACTGGATACCTATGTGCGTAATTGCGGCAAATACAACTATTATCT
GCAGGATGGTGAAATTGCGACCAGCGATTTTATTGCACGTAATCGTCAGAATGAAGCCTTTCTGCGTAACATTATT
GGTGTTAGCAGCGTTGCATATTTTAGCCTGCGTAATATCCTGGAAACCGAAACGAGAATGATATCACCGGTCGTA
TGCGTGGTAAAACCGTGAAAAACAATAAAGGCGAAGAGAAATATGTGAGCGGTGAGGTGGATAAAATCTACAACGA
AAACAAAAGAACGAAGTGAAAGAAAAACCTGAAAATGTTTTACAGCTACGACTTTAACATGGACAACAAGAACGAG
ATCGAAGATTTTTTCGCCAACATTGATGAAGCCATTAGCAGCATTCGTCATGGCATTGTTCACTTTAATCTGGAAC
```

TABLE 1-continued

Polynucleotide and Polypeptide Sequences of Cas Constructs

TTGAGGGCAAAGACATCTTCGCGTTTAAAAACATTGCACCGAGCGAGATTAGCAAAAAGATGTTCCAGAACGAAAT
TAACGAGAAAAAACTGAAACTGAAGATCTTTCGCCAGCTGAATAGCGCAAATGTTTTTCGCTATCTTGAGAAATAC
AAAATCCTGAACTATCTGAAACGCACCCGCTTTGAATTTGTGAACAAAAACATTCCGTTTGTGCCGAGCTTTACCA
AACTGTATAGCCGTATTGATGATCTGAAAAACAGCCTGGGCATTTATTGGAAAACCCCGAAAACCAACGATGATAA
CAAGACGAAAGAAATCATCGATGCCCAGATTTATCTGCTTAAGAACATCTACTATGGCGAATTTCTGAACTATTTT
ATGAGCAACAACGGCAACTTCTTTGAAATCAGCAAAGAGATTATCGAACTGTGAATAAAAACGACAAACGCAATCTGA
AAACCGGCTTCTATAAACTGCAGAAGTTTGAGGGATATCCAAGAAAAGATCCCGAAAGAATATCTGGCGAATATTCA
GAGCCTGTACATGATTAATGCAGGCAATCAGGATGAGGAAGAGAAAGATACCTATATCGATTTCATCCAGAAAATC
TTTCTGAAAGGCTTTATGACCTATCTGGCCAATAATGGTCGTCTGAGTCTGATTTATATCGGTAGTGATGAAGAAA
CCAATACCAGCCTGGCAGAAAAAAAACAAGAGTTCGATAAGTTCCTGAAGAAGTACGAACAGAACAACAACATCAA
GATCCCGTATGAAATCAATGAATTTCTGCGCGAAATCAAGCTGGGCAACATTCTGAAATACACCGAACGCCTGAAT
ATGTTCTATCTGATTCTGAAACTGCTGAACCATAAAGAGCTGACGAATCTGAAAGGTAGCCTGGAAAAGTATCAGA
GCGCAAATAAAGAGGAAGCATTTAGCGATCAGCTGGAACTGATTAATCTGCTGAATCTGGATAATAACCGTGTGAC
CGAAGATTTCGAATTAGAAGCAGATGAGATCGGCAAATTCCTGGATTTTAATGGCAACAAAGTGAAGGACAACAAA
GAGCTTAAGAAGTTCGACACCAACAAGATCTATTTTGATGGCGAGAACATCATCAACACCGTGCCTTTTATAACA
TCAAAAAATACGGTATGCTGAACCTGCTGGAAAAGATTGCAGATAAAGCAGGCTATAAAATCAGCATTGAAGAGTT
GAAAAAATACAGCAACAAGAAAACGAGATTGAGAAAAACCACAAAATGCAAGAAATCTGCACCGCAAATATGCA
CGTCCGCGTAAAGATGAAAATTCACCGATGAAGATTATGAAAGCTACAAACAGGCCATCGAAAACATCGAAGAAT
ATACCCATCTGAAGAACAAAGTCGAATTCAACGAACTGAATCTGCTGCAGGGTCTGCTGCTGCGTATTCTGCATCG
TCTGGTGGGTTATACCAGCATTTGGGAACGTGATCTGCGTTTTCGCCTGAAAGGTGAATTTCCTGAAAACCAGTAT
ATCGAGGAAATCTTCAACTTCGAGAATAAAAAGAATGTGAAGTATAAAGGTGGCCAGATCGTCGAGAATATATCA
AATTCTACAAAGAACTGCACCAGAACGACGAGGTGAAAATCAACAAATATAGCAGCGCGAACATCAAAGTGCTGAA
ACAAGAGAAAAAAGACCTGTACATCCGCAACTATATCGCCCACTTTAACTATATTCCGCATGCAGAAATTAGTCTG
CTGGAAGTTCTGGAAAACCTGCGTAAACTGCTGTCATATGATCGTAAACTTAAAAACGCCGTGATGAAAAGCGTTG
TGGACATCCTGAAAGAGTATGGTTTTGTTGCGACCTTTAAAATCGGTGCCGATAAAAAGATTGGTATTCAGACCCT
GGAAAGCGAGAAGATTGTTCACCTGAAAAATCTTAAGAAAAAGAAACTTATGACCGATCGCAATAGCGAGGAACTG
TGTAAACTGGTGAAAATTATGTTTGAGTATAAAATGGAAGAGAAGAAATCCGAAAATGGGGATCCGAATTCGAGCT
CCGTCGACAAGCTTGCGGCCGCACTCGAGCACCACCACCACCACCACTGA

LbuCas13a CTD-His Polypeptide Sequence
SEQ ID NO: 2
MKVTKVGGISHKKYTSEGRLVKSESEENRTDERLSALLNMRLDMYIKNPSSTETKENQKRIGKLKKFFSNKMVYLK
DNTLSLKNGKKENIDREYSETDILESDVRDKKNFAVLKKIYLNENVNSEELEVERNDIKKKLNKINSLKYSFEKNK
ANYQKINENNIEKVEGKSKRNIIYDYYRESAKRDAYVSNVKEAFDKLYKEEDIAKLVLEIENLTKLEKYKIREFYH
EIIGRKNDKENFAKIIYEEIQNVNNMKELIEKVPDMSELKKSQVFYKYYLDKEELNDKNIKYAFCHFVEIEMSQLL
KNYVYKRLSNISNDKIKRIFEYQNLKKLIENKLLNKLDTYVRNCGKYNYYLQDGEIATSDFIARNRQNEAFLRNII
GVSSVAYFSLRNILETENENDITGRMRGKTVKNNKGEEKYVSGEVDKIYNENKKNEVKENLKMFYSYDENMDNKNE
IEDFFANIDEAISSIRHGIVHFNLELEGKDIFAFKNIAPSEISKKMFQNEINEKKLKLKIFRQLNSANVFRYLEKY
KILNYLKRTRFEFVNKNIPFVPSFTKLYSRIDDLKNSLGIYWKTPKTNDDNKTKEIIDAQIYLLKNIYYGEFLNYF
MSNNGNFFEISKEIIELNKNDKRNLKTGFYKLQKFEDIQEKIPKEYLANIQSLYMINAGNQDEEEKDTYIDFIQKI
FLKGFMTYLANNGRLSLIYIGSDEETNTSLAEKKQEFDKFLKKYEQNNNIKIPYEINEFLREIKLGNILKYTERLN
MFYLILKLLNHKELTNLKGSLEKYQSANKEEAFSDQLELINLLNLDNNRVTEDFELEADEIGKFLDENGNKVKDNK
ELKKFDTNKIYFDGENIIKHRAFYNIKKYGMLNLLEKIADKAGYKISIEELKKYSNKKNEIEKNHKMQENLHRKYA
RPRKDEKFTDEDYESYKQAIENIEEYTHLKNKVEFNELNLLQGLLLRILHRLVGYTSIWERDLRFRLKGEFPENQY
IEEIFNFENKKNVKYKGGQIVEKYIKFYKELHQNDEVKINKYSSANIKVLKQEKKDLYIRNYIAHFNYIPHAEISL
LEVLENLRKLLSYDRKLKNAVMKSVVDILKEYGFVATFKIGADKKIGIQTLESEKIVHLKNLKKKKLMTDRNSEEL
CKLVKIMFEYKMEEKKSENGDPNSSSVDKLAAALEHHHHHH LbuCas13a NTD-MBP Polynucleotide Sequence
SEQ ID NO: 3
ATGAAAATCGAAGAAGGTAAACTGGTAATCTGGATTAACGGCGATAAAGGCTATAACGGTCTCGCTGAAGTCGGTA
AGAAATTCGAGAAAGATACCGGAATTAAAGTCACCGTTGAGCATCCGGATAAACTGGAAGAGAAATTCCCACAGGT
TGCGGCAACTGGCGATGGCCCTGACATTATCTTCTGGGCACACGACCGCTTTGGTGGCTACGCTCAATCTGGCCTG
TTGGCTGAAATCACCCCGGACAAAGCGTTCCAGGACAAGCTGTATCCGTTTACCTGGGATGCCGTACGTTACAACG
GCAAGCTGATTGCTTACCCGATCGCTGTTGAAGCGTTATCGCTGATTTATAACAAAGATCTGCTGCCGAACCCGCC
AAAAACCTGGGAAGAGATCCCGGCGCTGGATAAAGAACTGAAAGCGAAAGGTAAGAGCGCGCTGATGTTCAACCTG
CAAGAACCGTACTTCACCTGGCCGCTGATTGCTGCTGACGGGGGTTATGCGTTCAAGTATGAAAACGGCAAGTACG
ACATTAAAGACGTGGGCGTGGATAACGCTGGCGCGAAAGCGGGTCTGACCTTCCTGGTTGACCTGATTAAAAACAA
ACACATGAATGCAGACACCGATTACTCCATCGCAGAAGCTGCCTTTAATAAAGGCGAAACAGCGATGACCATCAAC
GGCCCGTGGGCATGGTCCAACATCGACACCAGCAAAGTGAATTATGGTGTAACGGTACTGCCGACCTTCAAGGGTC
AACCATCCAAACCGTTCGTTGGCGTGCTGAGCGCAGGTATTAACGCCGCCAGTCCGAACAAAGAGCTGGCAAAAGA
GTTCCTCGAAAACTATCTGCTGACTGATGAAGGTCTGGAAGCGGTTAATAAAGACAAACCGCTGGGTGCCGTAGCG
CTGAAGTCTTACGAGGAAGAGTTGGTGAAAGATCCGCGTATTGCCGCCACTATGGAAAACGCCCAGAAAGGTGAAA
TCATGCCGAACATCCCGCAGATGTCCGCTTTCTGGTATGCCGTGCGTACTGCGGTGATCAACGCCGCCAGCGGTCG
TCAGACTGTCGATGAAGCCCTGAAAGACGCGCAGACTAATTCGAGCTCGAACAACAATAACAATAACAACAACAAC
AACCTCGGGATCGAGGGAAGGAAGGTGACCAAAGTTGGTGGTATCAGCCATAAAAAGTATACCAGCGAAGGTCGTC
TGGTTAAAGCGAAAGCGAAGAAAATCGTACCGATGAACGTCTGAGCGCACTGCTGAATATGCGTCTGGATATGTA
TATCAAAAATCCGAGCAGCACCGAAACCAAAGAAAATCAGAAACGTATCGGCAAGCTGAAAAAGTTCTTCAGCAAC
AAAATGGTGTACCTGAAAGATAACACCCTGTCCCTGAAAAACGGCAAGAAAGAAAATATCGATCGCGAGTATAGCG
AAACCGATATTCTGGAAAGTGATGTGCGTGACAAAAAAAACTTTGCCGTCCTGAAAAAGATCTATCTGAACGAAAA
TGTGAACAGCGAAGAACTGGAAGTGTTCGCAACGACATTAAAAAGAAGCTGAACAAGATCAACAGCCTGAAATAT
AGCTTCGAGAAAAACAAAGCCAACTATCAGAAGATCAACGAGAACAACATCGAAAAGTGGAAGGTAAAAGCAAGC
GCAACATCATCTATGATTATTATCGTGAAAGCGCCAAACGTGACGCTTACGTTAGCAATGTTAAAGAGGCCTTCGA
CAAGCTGTATAAAGAAGAAGATATTGCCAAACTGGTGCTGGAAATTGAAAATCTGACCAAGCTGGAAAAATACAAG
ATCCGCGAATTCTATCACGAAATCATTGGTCGCAAAAACGATAAAGAGAACTTCGCCAAAATCATCTACGAAGAAA
TTCAGAACGTGAATAACATGAAAGAACTGATCGAGAAAGTTCCGGATATGAGCGAACTGAAAAAAAGCCAGGTGTT
CTACAAATATTACCTGGACAAAGAGGAACTGAACGATAAAAACATCAAATACGCCTTTTGCCACTTCGTGGAAATC
GAAATGAGCCAGCTGCTGAAAAACTATGTGTATAAACGCCTGAGCAACATCAGCAACGATAAGATTAAACGCATCT TABLE 1-continued Polynucleotide and Polypeptide Sequences of Cas Constructs TCGAGTACCAGAACCTGAAGAAACTGATTGAAAACAAACTGCTTAACAAACTGGATACCTATGTGCGTAATTGCGG
CAAATACAACTATTATCTGCAGGATGGTGAAATTGCGACCAGCGATTTTATTGCACGTAATCGTCAGAATGAAGCC
TTTCTGCGTAACATTATTGGTGTTAGCAGCGTTGCATATTTTAGCCTGCGTAATATCCTGGAAACCGAAAACGAGA
ATGATATCACCGGTCGTATGCGTGGTAAAACCGTGAAAAACAATAAAGGCGAAGAGAAATATGTGAGCGGTGAGGT
GGATAAAATCTACAACGAAAACAAAAAGAACGAAGTGAAAGAAAACCTGAAAATGTTTTACAGCTACGACTTTAAC
ATGGACAACAAGAACGAGATCGAAGATTTTTTCGCCAACATTGATGAAGCCATTAGCAGCATTCGTCATGGCATTG
TTCACTTTAATCTGGAACTTGAGGGCAAAGACATCTTCGCGTTTAAAAACATTGCACCGAGCGAGATTAGCAAAA
GATGTTCCAGAACGAAATTAACGAGAAAAACTGAAACTGAAGATCTTTCGCCAGCTGAATAGCGCAAATGTTTTT
CGCTATCTTGAGAAATACAAAATCCTGAACTATCTGAAACGCACCCGCTTTGAATTTGTGAACAAAACATTCCGT
TTGTGCCGAGCTTTACCAAACTGTATAGCCGTATTGATGATCTGAAAAACAGCCTGGGCATTTATTGGAAAACCCC
GAAAACCAACGATGATAACAAGACGAAAGAAATCATCGATGCCCAGATTTATCTGCTTAAGAACATCTACTATGGC
GAATTTCTGAACTATTTTATGAGCAACAACGGCAACTTCTTTGAAATCAGCAAAGAGATTATCGAGCTGAATAAAA
ACGACAAACGCAATCTGAAAACCGGCTTCTATAAACTGCAGAAGTTTGAGGATATCCAAGAAAAGATCCCGAAAGA
ATATCTGGCGAATATTCAGAGCCTGTACATGATTAATGCAGGCAATCAGGATGAGGAAGAGAAAGATACCTATATC
GATTTCATCCAGAAAATCTTTCTGAAAGGCTTTATGACCTATCTGGCCAATAGGTCGTCTGAGTCTGATTTATA
TCGGTAGTGATGAAGAAACCAATACCAGCCTGGCAGAAAAAAAACAAGAGTTCGATAAGTTCCTGAAGAAGTACGA
ACAGAACAACAACATCAAGATCCCGTATGAAATCAATGAATTTCTGCGCGAAATCAAGCTGGGCAACATTCTGAAA
TACACCGAACGCCTGAATATGTTCTATCTGATTCTGAAACTGCTGAACCATAAAGAGCTGACGAATCTGAAAGGTA
GCCTGGAAAAGTATCAGAGCGCAAATAAAGAGGAAGCATTTAGCGATCAGCTGGAACTGATTAATCTGCTGAATCT
GGATAATAACCGTGTGACCGAAGATTTCGAATTAGAAGCAGATGAGATCGGCAAATTCCTGGATTTTAATGGCAAC
AAAGTGAAGGACAACAAAGAGCTTAAGAAGTTCGACACCAACAAGATCTATTTTGATGGCGAGAACATCATCAAAC
ACCGTGCCTTTTATAACATCAAAAAATACGGTATGCTGAACCTGCTGGAAAAGATTGCAGATAAAGCAGGCTATAA
AATCAGCATTGAAGAGTTGAAAAAATACGACAACAAGAAAAACGAGATTGAAAACAACCACAAAATGCAAGAAAAT
CTGCACCGCAAATATGCACGTCCGCGTAAAGATGAAAAATTCACCGATGAAGATTATGAAAGCTACAAACAGGCCA
TCGAAAACATCGAAGAATATACCCATCTGAAGAACAAGTCGAATTCAACGAACTGAATCTGCTGCAGGGTCTGCT
GCTGCGTATTCTGCATCGTCTGGTGGGTTATACCAGCATTTGGGAACGTGATCTGCGTTTTCGCCTGAAAGGTGAA
TTTCCTGAAAACCAGTATATCGAGGAAATCTTCAACTTCGAGAATAAAAATGGTGGTTTGATTAAAGTCGGTATCAAAG
TCGTCGAGAAATATATCAAATTCTACAAAGAACTGCACCAGAACGACGAGGTGAAAATCAACAAATATAGCAGCGC
GAACATCAAAGTGCTGAAACAAGAGAAAAAAGACCTGTACATCCGCAACTATATCGCCCACTTTAACTATATTCCG
CATGCAGAAATTAGTCTGCTGGAAGTTCTGGAAAACCTGCGTAAACTGCTGTCATATGATCGTAAACTTAAAAACG
CCGTGATGAAAAGCGTTGTGGACATCCTGAAAGAGTATGGTTTTGTGACCTTTAAATCGGTGCCGATAAAA
GATTGGTATTCAGACCCTGGAAAGCGAGAAGATTGTTCACCTGAAAAATCTTAAGAAAAAGAAACTTATGACCGAT
CGCAATAGCGAGGAACTGTGTAAACTGGTGAAAATTATGTTTGAGTATAAAATGGAAGAAGAAATCCGAAAATG
ATCCGAATTCGAGCTCCGTCGACAAGCTTGCGGCCGCACTCGAGCACCACCACCACCACCACTGA LbuCas13a NTD-MBP Polypeptide Sequence

SEQ ID NO: 4

MKIEEGKLVIWINGDKGYNGLAEVGKKFEKDTGIKVTVEHPDKLEEKFPQVAATGDGPDIIFWAHDRFGGYAQSGL
LAEITPDKAFQDKLYPFTWDAVRYNGKLIAYPIAVEALSLIYNKDLLPNPPKTWEEIPALDKELKAKGKSALMENL
QEPYFTWPLIAADGGYAFKYENGKYDIKDVGVDNAGAKAGLTFLVDLIKNKHMNADTDYSIAEAAFNKGETAMTIN
GPWAWSNIDTSKVNYGVTVLPTFKGQPSKPFVGVLSAGINAASPNKELAKEFLENYLLTDEGLEAVNKDKPLGAVA
LKSYEEELVKDPRIAATMENAQKGEIMPNIPQMSAFWYAVRTAVINAASGRQTVDEALKDAQTNSSSNNNNNNNNN
NLGIEGRKVTKVGGISHKKYTSEGRLVKSESEENRTDERLSALLNMRLDMYIKNPSSTETKENQKRIGKLKKFFSN
KMVYLKDNTLSLKNGKKENIDREYSETDILESDVRDKKNFAVLKKIYLNENVNSEELEVFRNDIKKKLNKINSLKY
SFEKNKANYQKINENNIEKVEGKSKRNIIYDYYRESAKRDAYVSNVKEAFDKLYKEEDIAKLVLEIENLTKLEKYK
IREFYHEIIGRKNDKENFAKIIYEEIQNVNNMKELIEKVPDMSELKKSQVFYKYYLDKEELNDKNIKYAFCHFVEI
EMSQLLKNYVYKRLSNISNDKIKRIFEYQNLKKLIENKLLNKLDTYVRNCGKYNYYLQDGEIATSDFIARNRQNEA
FLRNIIGVSSVAYFSLRNILETENENDITGRMRGKTVKNNKGEEKYVSGEKDKIYNENKKNEVKENLKMFYSYDEN
MDNKNEIEDFFANIDEAISSIRHGIVHFNLELEGKDIFAFKNIAPSEISKKMFQNEINEKKLKLKIFRQLNSANVE
RYLEKYKILNYLKRTRFEFVNKNIPFVPSFTKLYSRIDDLKNSLGIYWKTPKTNDDNKTKEIIDAQIYLLKNIYYG
EFLNYFMSNNGNFFEISKEIIELNKNDKRNLKTGFYKLQKFEDIQEKIPKEYLANIQSLYMINAGNQDEEEKDTYI
DFIQKIFLKGFMTYLANNGRLSLIYIGSDEETNTSLAEKKQEFDKFLKKYEQNNNIKIPYEINEFLREIKLGNILK
YTERLNMFYLILKLLNHKELTNLKGSLEKYQSANKEEAFSDQLELINLLNLDNNRVTEDFELEADEIGKFLDENGN
KVKDNKELKKFDTNKIYFDGENIIKHRAFYNIKKYGMLNLLEKIADKAGYKISIEELKKYSNKKNEIEKNHKMQEN
LHRKYARPRKDEKFTDEDYESYKQAIENIEEYTHLKNKVEFNELNLLQGLLLRILHRLVGYTSIWERDLRFRLKGE
FPENQYIEEIFNFENKKNVKYKGGQIVEKYIKFYKELHQNDEVKINKYSSANIKVLKQEKKDLYIRNYIAHFNYIP
HAEISLLEVLENLRKLLSYDRKLKNAVMKSVVDILKEYGFVATFKIGADKKIGIQTLESEKIVHLKNLKKKKLMTD
RNSEELCKLVKIMFEYKMEEKKSENDPNSSSVDKLAAALEHHHHHH

LshCas13a NTD-His Polynucleotide Sequence

SEQ ID NO: 5

ATGGGTAACCTGTTTGGTCATAAACGTTGGTATGAAGTGCGCGACAAAAAGACTTTAAAATCAAACGCAAGGTGA
AGTGAAACGCAACTATGATGGCAACAAATATATCCTGAACATCAACGAGAACAACAAAGAGAAGATCGATAA
TAATAAAATTCATCCGCAAATACATCAACTACAAAAAAACGATAACATCCTGAAAGAATTCACCCGCAAGTTTCAT
GCAGGCAACATTCTGTTTAAACTGAAAGGCAAAGAAGGCATCATTCGCATCGATGAAAATGATGATTTTCTGGAAA
CCGAAGAGGTGGTGCTGTATATTGAAGCATATGGCAAAGCGAAAAACTGAAGGCACTGGGCATTACCAAAAAAAA
GATTATCGATGAAGCCATTCGCCAGGGTATTACCAAAGATGACAAAAGATCGAGATCAAGCGCAAGAAACGAA
GAAGAAATCGAATTGATATCCGCGACGAGTATACCAATAAAACCCTGAATGATTGCAGCATTATTCTGCGCATTA
TCGAGAATGATGAGCTGGAACAGAAAAAGACATCTACGAGATCTTCAAAAACATCAACATGAGCCTGTACAAAAT
CATCGAGAAATTTATCGAAAACGAAACCGAGAAGGTGTTCGAGAATCGCTATTATGAAGAACATCTGCGTGAGAAA
CTGCTGAAAGATGATAAAATTGATGTGATCCTGACCAACTTCATGGAAATCCGCGAAAGATTAAAGCAACCTGG
AAATTCTGGGCTTCGTGAAATTCTATCTGAATGTTGGTGGCGACAAGAAAAAAGCAAGAACAAGAAATGCTGGT
CGAAAAATTCTGAACATTAACGTTGATCTGACCGTGGAAGATATTGCCGATTTTGTTCTGAAAAGCTGGATAAATTC
TGGAACATCACCAAACGCATTGAGAAGGTGAAAAAGTGAACAACGAGTTCCTGGAAAAACGTCGTAATCGCACCT
ATATCAAAGCTATGTTCTGCTGGATAAGCACGAGAATTCAAATTGAACGCGAGAACAAAAGGACAAATCGT
GAAGTTTTCGTGGAAAATATCAAAACAACAGCATCAAAGAAAAATCGAGAAGATCCTGGCCGAGTTCAAATC
GATGAACTGATCAAAAGCTGGAAAAAGAACTGAAAAAGGCAACTGCGATACCGAATTTTCGGCATCTTTAAGA
AACACTATAAAGTGAACTTCGATAGCAAAAAATTCAGCAAAAAGAGCGACGAAGAGAAAGAGCTGTATAAGATCAT

TABLE 1-continued

Polynucleotide and Polypeptide Sequences of Cas Constructs

```
TTACCGCTATCTGAAAGGCCGTATTGAAAAAATCCTGGTGAATGAACAGAAAGTGCGCCTGAAAAAAATGGAAAAA
ATTGAGATTGAGAAGATTCTGAACGAGAGCATCCTGAGTGAGAAATCCTGAAACAGTATACCCTGG
AACACATTATGTATCTGGGTAAACTGCGCCATAACGATATTGATATGACCACCGTTAATACCGATGATTTCAGCCG
TCTGCATGCAAAAGAAGAACTGGATCTGGAACTGATTACCTTTTTTGCAAGCACCAATATGGAACTGAACAAGATC
TTTAGCCGTGAAAACATTAACAACGACGAGAACATTGATTTCTTTGGTGGTGATCGCGAGAAAAACTATGTCCTGG
ATAAAAAGATCCTGAATAGCAAAATCAAGATCATCCGCGATCTGGATTTCATCGACAATAAGAACAACATTACCAA
CAACTTTATTCGCAAATTTACCAAAATTGGCACCAATGAACGCAACCGTATTCTGCATGCCATTAGCAAAGAACGT
GATCTGCAGGGCACCCAGGATGATTATAACAAAGTGATTAACATCATCCAGAACCTGAAAATCTCCGATGAAGAAG
TTAGCAAAGCACTGAATCTGGATGTGGTGTTCAAAGATAAGAAAAATATCATCACCAAGATCAACGATATCAAAAT
CAGCGAAGAGAACAATAACGACATCAAATATCTGCCGAGCTTTAGCAAAGTTCTGCCGGAAATTCTTAATCTGTAT
CGCAATAACCCGAAAAACGAACCGTTTGATACCATCGAAACAGAGAAAATTGTTCTGAACGCCCTGATCTATGTGA
ACAAAGAACTGTACAAGAAACTGATCCTGGAAGATGATCTGGAAGAGAACGAATCGAAAAACATCTTTCTGCAAGA
GCTGAAAAAGACCCTGGGTAACATTGATGAGATCGATGAAAACATCATCGAAATTACTACAAGAACGCACAGATT
AGCGCAAGCAAAGGTAATAACAAAGCCATCAAAAAATACCAGAAAAAGGTGATCGAATGCTACATTGGTTATCTGC
GCAAAAACTACGAAGAACTGTTCGATTTCAGCGATTTCAAAATGAACATTCAGGAAATTAAGAAGCAGATCAAGGA
CATTAACGACAACAAAACCTATGAACGCATCACCGTTAAAACCAGCGATAAAACCATTGTGATCAACGACGATTTC
GAGTACATCATTAGCATTTTTGCACTGCTGAATTCCAACGCCGTGATCAACAAAATTCGCAATCGCTTTTTTGCCA
CCAGTGTTTGGCTGAATACCAGCGAATATCAGAACATTATCGATATCCTGGATGAGATCATGCAGCTGAATACACT
GCGTAATGAATGCATTACCGAAAACTGGAATCTGAACCTTGAAGAATTTATTCAGAAAATGAAAGAGATCGAGAAA
GACTTCGACGACTTCAAAATCCAGACCAAAAAAGAAATCTTCAACAACTACTACGAGGACATCAAAAATAACATTC
TGACCGAATTCAAAGACGATATTAACGGCTGTGACGTGCTGGAAAAGAAGTTGGAAAAGATCGTTATCTTCGATGA
CGAAACCAAATTCGAAATCGACAAAAAGTCCAACATCCTTCAGGATGAACAGCGTAAACTGAGCAATATCAACAAG
AAAGACCTGAAGAAGAAGGTCGACCAGTACATCAAAGACAAGGACCAAGAAATTAAGAGCAAAATCCTGTGCCGCA
TCATCTTTAACAGCGACTTTCTGAAAAAGTATAAGAAAGAGATTGACAACCTGATCGAGGATATGGAAAGCGAGAA
CGAAAACAAGTTTCAAGAGATCTACTATCCGAAAGAACGCAAAAACGAGCTGTACATCTACAAGAAGAACCTGTTC
CTGAATATTGGCAACCCGAACTTCGACAAAATCTATGGTCTGATCAGCAACGACATTAAAATGGCCGATGCAAAAT
TCCTGTTTAATATCGATGGTAAAAACATCCGTAAAAACAAAATTAGCGAGATCGACGCGATCCTGAAAAACCTGAA
CGATAAACTGAATGGCTACAGCAAAGAATATAAAGAGAAATACATTAAAAAGCTGAAAGAAAATGACGACTTCTTC
GCCAAGAACATCCAGAATAAAAACTATAAAAGCTTCGAGAAGGACTACAATCGCGTGTCCGAATATAAGAAAATTC
GTGATCTGGTGGAATTCAACTATCTGAACAAAATCGAAGCTATCTGATCGATATCAACTGGAAACTGGCAATTCA
GATGGCACGTTTTGAGCGTGATATGCACTATATTGTTAATGGTCTGCGTGAACTGGGCATCATTAAACTGAGTGGT
TATAATACCGGCATTAGCCGTGCATATCCGAAACGTAATGGTTCCGATGGTTTTTATACCACCACCGCCTATTACA
AATTTTTCGACGAAGAAAGCTACAAGAAATTTGAGAAATTTGCTACGGCTTCGGCATTGATCTGAGCGAAAATAG
CGAAATTAACAAGCCGGAAATGAGAGCATTCGCAACTATATCTCCCACTTTTATATCGTCGTAATCCGTTTGCC
GATTATAGCATTGCAGAGCAGATTGATCGTGTTAGCAATCTGCTGAGCTATAGTACCCGTTATAACAATAGCACCT
ATGCCAGCGTGTTTGAGGTGTTTAAAAAGGATGTTAACCTGGACTATGACGAGCTGAAGAAAAAGTTCAAACTGAT
CGGCAACAATGACATCCTGGAACGTCTGATGAAACCGAAAAAAGTTAGTGTGCTGGAACTTGAGAGCTACAACAGC
GATTATATCAAGAACCTGATTATCGAGCTGCTGACCAAGATTGAAAATACCAATGATACCCTGGGGGATCCGAATT
CGAGCTCCGTCGACAAGCTTGCGGCCGCACTCGAGCACCACCACCACCACCACTGA
```

LshCas13a NTD-His Polypeptide Sequence

SEQ ID NO: 6

```
MGNLFGHKRWYEVRDKKDFKIKRKVKVKRNYDGNKYILNINENNNKEKIDNNKFIRKYINYKKNDNILKEFTRKFH
AGNILFKLKGKEGIIRIENNDDFLETEEVVLYIEAYGKSEKLKALGITKKKIIDEAIRQGITKDDKKIEIKRQENE
EEIEIDIRDEYTNKTLNDCSIILRIIENDELETKKSIYEIFKNINMSLYKIIEKIIENETEKVFENRYYEEHLREK
LLKDDKIDVILTNFMEIREKIKSNLEILGFVKFYLNVGGDKKKSKNKKMLVEKILNINVDLTVEDIADFVIKELEF
WNITKRIEKVKKVNNEFLEKRRNRTYIKSYVLLDKHEKFKIERENKKDKIVKFFVENIKNNSIKEKIEKILAEFKI
DELIKKLEKELKKGNCDTEIFGIFKKHYKVNFDSKKFSKKSDEEKELYKIIYRYLKGRIEKILVNEQKVRLKKMEK
IEIEKILNESILSEKILKRVKQYTLEHIMYLGKLRHNDIDMTTVNTDDFSRLHAKEELDLELITFFASTNMELNKI
FSRENINNDENIDFFGGDREKNYVLDKKILNSKIKIIRDLDPIDNKNNITNNFIRKFTKIGTNERNRILHAISKER
DLQGTQDDYNKVINIIQNLKISDEEVSKALNLDVVFKDKKNIITKINDIKISEENNNDIKYLPSFSKVLPEILNLY
RNNPKNEPFDTIETEKIVLNALIYVNKELYKKLILEDDLEENESKNIFLQELKTLGNIDEIDENIIENYYKNAQI
SASKGNNKAIKKYQKKVIECYIGYLRKNYEELFDFSDFKMNIQEIKKQIKDINDNKTYERITVKTSDKTIVINDDE
EYIISIFALLNSNAVINKIRNRFFATSVWLNTSEYQNIIDILDEIMQLNTLRNECITENWNLNLEEFIQKMKEIEK
DFDDDFKIQTKKEIFNNYYEDIKNNILTEFKDDINGCDVLEKKLEKIVIFDDETKFEIDKKSNILQDEQRKLSNINK
KDLKKKVDQYIKDKDQEIKSKILCRIIFNSDFLKKYKKEIDNLIEDMESENENKFQEIYYPKERKNELYIYKKNLF
LNIGNPNFDKIYGLISNDIKMADAKFLFNIDGKNIRKNKISEIDAILKNLNDKLNGYSKEYKEKYIKKLKENDDFF
AKNIQNKNYKSFEKDYNRVSEYKKIRDLVEFNYLNKIESYLIDINWKLAIQMARFERDMHYIVNGLRELGIIKLSG
YNTGISRAYPKRNGSDGFYTTAYYKFFDEESYKKFEKICYGFGIDLSENSEINKPENESIRNYISHFYIVRNPFA
DYSIAEQIDRVSNLLSYSTRYNNSTYASVFEVFKKDVNLDYDELKKKFKLIGNNDILERLMKPKKVSVLELESYNS
DYIKNLIIELLTKIENTNDTLGDPNSSSVDKLAAALEHHHHH
```

LshCas13a NTD-MBP Polynucleotide Sequence

SEQ ID NO: 7

```
ATGAAAATCGAAGAAGGTAAACTGGTAATCTGGATTAACGGCGATAAAGGCTATAACGGTCTCGCTGAAGTCGTA
AGAAATTCGAGAAAGATACCGGAATTAAAGTCACCGTTGAGCATCCGGATAAACTGGAAGAGAAATTCCCACAGGT
TGCGGCAACTGGCGATGGCCCTGACATTATCTTCTGGGCACACGACCGCTTTGGTGGCTACGCTCAATCGGCCTG
TTGGCTGAAATCACCCCGGACAAAGCGTTCCAGGACAAGCTGTATCCGTTTACCTGGGATGCCGTACGTTACAACG
GCAAGCTGATTGCTTACCCGATCGCTGTTGAAGCGTTATCGCTGATTTATAACAAAGATCTGCTGCCGAACCCGCC
AAAAACCTGGGAAGAGATCCCGGCGCTGGATAAAGAACTGAAAGCGAAAGGTAAGAGCGCGCTGATGTTCAACCTG
CAAGAACCGTACTTCACCTGGCCGCTGATTGCTGCTGACGGGGGTTATGCGTTCAAGTATGAAACGGCAAGTACG
ACATTAAAGACGTGGGCGTGGATAACGCTGGCGCGAAAGCGGGTCTGACCTTCCTGGTTGACCTGATTAAAAACAA
ACACATGAATGCAGACACCGATTACTCCATCGCAGAAGCTGCCTTTAATAAAGGCGAAACAGCGATGACCATCAAC
GGCCCGTGGGCATGGTCCAACATCGACACCAGCAAAGTGAATTATGGTGTAACGGTACTGCCGACCTTCAAGGGTC
AACCATCCAAACCGTTCGTTGGCGTGCTGAGCGCAGGTATTAACGCCGCCAGTCCGAACAAAGAGCTGGCAAAAGA
GTTCCTCGAAAACTATCTGCTGACTGATGAAGGTCTGGAAGCGGTTAATAAAGACAAACCGCTGGGTGCCGTAGCG
CTGAAGTCTTACGAGGAAGAGTTGGTGAAAGATCCGCGTATTGCCGCCACTATGGAAAACGCCCAGAAAGGTGAAA
TCATGCCGAACATCCCGCAGATGTCCGCTTTCTGGTATGCCGTGCGTACTGCGGTGATCAACGCCGCCAGCGGTCG
```

TABLE 1-continued

Polynucleotide and Polypeptide Sequences of Cas Constructs

```
TCAGACTGTCGATGAAGCCCTGAAAGACGCGCAGACTAATTCGAGCTCGAACAACAACAACAATAACAATAACAAC
AACCTCGGGATCGAGGGAAGgGGTAACCTGTTTGGTCATAAACGTTGGTATGAGGTGCGCGACAAAAAAGACTTTA
AAATCAAACGCAAGGTGAAAGTGAAACGCAACTATGATGGCAACAAATATATCCTGAACATCAACGAGAACAACAA
CAAAGAGAAGATCGATAATAATAAATTCATCCGCAAATACATCAACTACAAAAAAAACGATAACATCCTGAAAGAA
TTCACCCGCAAGTTTCATGCAGGCAACATTCTGTTTAAACTGAAAGGCAAAGAAGGCATCATTCGCATCGAAAACA
ATGATGATTTTCTGGAAACCGAAGAGGTGGTGCTGTATATTGAAGCATATGGCAAAAGCGAAAAACTGAAGGCACT
GGGCATTACCAAAAAAAAGATTATCGATGAAGCCATTCGCCAGGGTATTACCAAAGATGACAAAAAGATCGAGATC
AAGCGCCAAGAAAACGAAGAAGAAATCGAAATTGATATCCGCGACGAGTATACCAATAAAACCCTGAATGATTGCA
GCATTATTCTGCGCATTATCGAGAATGATGAGCTGGAAACGAAAAAGAGCATCTACGAGATCTTCAAAAACATCAA
CATGAGCCTGTACAAAATCATCGAGAAAATTATCGAAAACGAAACCGAGAAGGTGTTCGAGAATCGCTATTATGAA
GAACATCTGCGTGAGAAACTGCTGAAAGATGATAAAATTGATGTGATCCTGACCAACTTCATGGAAATCCGCGAAA
AGATTAAAAGCAACCTGGAAATTCTGGGCTTCGTGAAATTCTATCTGAATGTTGGTGGCGACAAGAAAAAAAGCAA
GAACAAGAAAATGCTGGTCGAAAAAATTCTGAACATTAACGTTGATCTGACCGTGGAAGATATTGCCGATTTTGTG
ATTAAAGAGCTGGAATTCTGGAACATCACCAAAGCATTGAGAAGGTGAAAAAAGTGAACAACGAGTTCCTGGAAA
AACGTCGTAATCGACACCTATATCAAAAGCTATGTTCTGCTGGATAAGCACGAGAAATTCAAAATTGAACGCGAGA
CAAAAAGGACAAAATCGTGAAGTTTTTCGTGGAAAATATCAAAAACAACAGCATCAAAGAAAAAATCGAGAAGATC
CTGGCCGAGTTCAAAATCGATGAACTGATCAAAAAGCTGGAAAAAGAACTGAAAAAAGGCAACTGCGATACCGAAA
TTTTCGGCATCTTTAAGAAACACTATAAAGTGAACTTCGATAGCAAAAAATTCAGCAAAAAGAGCGACGAAGAGAA
AGAGCTGTATAAGATCATTTACCGCTATCTGAAAGGCCGTATCGAAAAATCCTGGTGAATGAACAGAAAGTGCGC
CTGAAAAAAATGGAAAAAATTGAGATTGAGAAGATTCTGAACGAGAGCATCCTGAGTGAGAAAATCCTGAAACGTG
TTAAACAGTATACCCTGGAACACATTATGTATCTGGGTAAACTGCGCCATAACGATATTGATATGACCACCGTTAA
TACCGATGATTTCAGCCGTCTGCATGCAAAAGAAGAACTGGATCTGGAACTGATTACCTTTTTTGCAAGCACCAAT
ATGGAACTGAACAAGATCTTTAGCCGTGAAAACATTAACAACGACGAGAATCTGATTTCTTTGGCGGGATCGCG
AGAAAAAACTATGTCCTGGATAAAAAGATCCTGAATAGCAAAATCAAGATCATCCGCGATCTGGATTTCATCGACAA
TAAGAACAACATTACCAACAACTTTATTCGCAAATTTACCAAATTGGCACCAATGAACGCAACCGTATTCTGCAT
GCCATTAGCAAAGAACGTGATCTGCAGGGCACCCAGGATGATTATAACAAAGTGATTAACATCATCCAGAACCTGA
AAATCTCCGATGAAGAAGTTAGCAAAGCACTGAATCTGGATGTGGTGTTCAAAGATAAGAAAAATATCATCACCAA
GATCAACGATATCAAAATCAGCGAAGAGAACAATAACGACATCAAATATCTGCCGAGCTTTAGCAAAGTTCTGCCG
GAAATTCTTAATCTGTATCGCAATAACCCGAAAAACGAACCGTTTGATACCATCGAAACAGAGAAATTGTTCTGA
ACGCCCTGATCTATGTGAACAAGAACTGTACAAGAAACTGATCCTGGAAGATGATCTGGAAGAACGAATCGAA
AAACATCTTTCTGCAAGAGCTGAAAAAAGACCCTGGGTAACATTGATGAGATCGATGAAAACATCATCGAAAATTAC
TACAAGAACGCACAGATTAGCGCAAGCAAAGGTAATAACAAAGCCATCAAAAAATACCAGAAAAAGGTGATCGAAT
GCTACATTGGTTATCTGCGCAAAAACTACGAAGAACTGTTCGATTTCAGCGATTTCAAAATGAACATCCAAGAGAT
CAAGAAGCAGATCAAGGACATTAACGACAACAAAACCTATGAACGCATCACCGTTAAAACCAGCGATAAACCATT
GTGATCAACGACGATTTCGAGTACATCATTAGCATTTTTGCACTGCTGAATTCCAACGCCGTGATCAACAAATTC
GCAATCGCTTTTTTGCCACCAGTGTTTGGCTGAATACCAGCGAATATCAGAACATTATCGATATCCTGGATGAGAT
CATGCAGCTGAATACACTGCGTAATGAATGCATTACCGAAAACTGGAATCTGAACCTTGAAGAATTTATTCAGAAA
ATGAAAGAGATCGAGAAAGACTTCGACGACTTCAAAATCCAGACCAAAAAAGAAATCTTCAACAACTACTACGAGG
ACATCAAAAATAACATTCTGACCGAATTCAAAGACGATATTAACGGCGTGACGTGCTGGAAAAGAAGTTGGAAAA
GATCGTTATCTTCGATGACGAAACCAAATTCGAAATCGACAAAAAGTCCAACATCCTTCAGGATGAACAGCGTAAA
CTGAGCAATATCAACAAGAAAGACCTGAAGAAGAAGGTCGACCAGTACATCAAAGACAAAGACCAAGAATTAAGA
GCAAAATCCTGTGCCGCATCATCTTTAACAGCGACTTTCTGAAAAAGTATAAGAAAGAGATTGACAACCTGATCGA
GGATATGGAAAGCGAGAACGAAAACAAGTTTCAAGAGATCTACTATCCGAAAGAACGCAAAAACGAGCTGTACATC
TACAAGAAGAACCTGTTCCTGAATATTGGCAACCCGAACTTCGACAAAACTATGGTCTGATCAGCAACGACATTA
AAATGGCCGATGCAAAATTCCTGTTTAATATCGATGGTAAAAACATCCGTAAAAACAAATTAGCGAGATCGACGC
GATCCTGAAAAACCTGAACGATAAACTGAATGGCTACAGCAAGAATATAAAGAGAAATACATTAAAAAGCTGAAA
GAAAATGACGACTTCTTCGCCAAGAACATCCAGAATAAAAACTATAAAAGCTTCGAGAAGGACTACAATCGCGTGT
CCGAATATAAGAAATTCGTGATCTGGTGGAATTCAACTATCTGAACAATAAACTGAAAGCTATCTGATCGATATCAA
CTGGAAACTGGCAATTCAGATGGCACGTTTTGAGCGTGATATGCACTATATTGTTAATGGTCTGCGTGAACTGGGC
ATCATTAAACTGAGTGGTTATAATACCGGCATTAGCCGTGCATATCCGAAACGTAATGGTTCCGATGGTTTTTATA
CCACCACCGCCTATTACAAATTTTTCGACGAAGAAAGCTACAAGAAATTTGAGAAATTTGCTACGGCTTCGGCAT
TGATCTGAGCGAAAATAGCGAAATTAACAAGCCGGAAAATGAGCATTGCAACTATATCTCCCACTTTTATATC
GTGCGTAATCCGTTTGCCGATTATAGCATTGCAGAGCAGATTGATCGTGTTAGCAATCTGCTGAGCTATAGTACCC
GTTATAACAATAGCACCTATGCCAGCGTGTTTGAGGTGTTTAAAAAGGATGTTAACCTGGACATGACGAGCTGAA
GAAAAAGTTCAAACTGATCGGCAACAATGACATCCTGGAACGTCTGATGAAACCGAAAAAGTTAGTGTGCTGGAA
CTTGAGAGCTACAACAGCGATTATATCAAGAACCTGATTATCGAGCTGCTGACCAAGATTGAAAATACCAATGATA
CCCTGGATCCGAATTCGAGCTCCGTCGACAAGCTTGCGGCCGCACTCGAGCACCACCACCACCACCACTGA
```

LshCas13a NTD-MBP Polypeptide Sequence

SEQ ID NO: 8

MKIEEGKLVIWINGDKGYNGLAEVGKKFEKDTGIKVTVEHPDKLEEKFPQVAATGDGPDIIFWAHDRFGGYAQSGL
LAEITPDKAFQDKLYPFTWDAVRYNGKLIAYPIAVEALSLIYNKDLLPNPPKTWEEIPALDKELKAKGKSALMENL
QEPYFTWPLIAADGGYAFKYENGKYDIKDVGVDNAGAKAGLTFLVDLIKNKHMNADTDYSIAEAAFNKGETAMTIN
GPWAWSNIDTSKVNYGVTVLPTFKGQPSKPFVGVLSAGINAASPNKELAKEFLENYLLTDEGLEAVNKDKPLGAVA
LKSYEEELVKDPRIAATMENAQKGEIMPNIPQMSAFWYAVRTAVINAASGRQTVDEALKDAQTNSSSNNNNNNNNN
NLGIEGRGNLFGHKRWYEVRDKKDFKIKRKVKVKRNYDGNKYILNINENNNKEKIDNNKFIRKYINYKKNDNILKE
FTRKFHAGNILFKLKGKEGIIRIENNDDELETEEVVLYIEAYGKSEKLKALGITKKKIIDEAIRQGITKDDKKIEI
KRQENEEEIEIDIRDEYTNKTLNDCSIILRIIENDELETKKSIYEIFKNINMSLYKIIEKIIENETEKVFENRYYE
EHLREKLLKDKDKIDVILTNFMEIREKISNLEILGFVKFYLNVGGDKKKSKNKKMLVEKILNINVDLTVEDIADFV
IKELEFWNITKRIEKVKKVNNEFLEKRRNRTYIKSYVLLDKHEKFKIERENKKDKIVKFFVENIKNNSIKEKIEKI
LAEFKIDELIKKLEKELKKGNCDTEIFGIFKKHYKVNFDSKKESKKSDEEKELYKIIYRYLKGRIEKILVNEQKVR
LKKMEKIEIEKILNESILSEKILKRVKQYTLEHIMYLGKLRHNDIDMTTVNTDDFSRLHAKEELDLELITFFASTN
MELNKIFSRENINNDENIDFFGGDREKNYVLDKKILNSKIKIIRDLDFIDNKNNITNNFIRKFTKIGTNERNRILH
AISKERDLQGTQDDYNKVINIIQNLKISDEEVSKALNLDVVFKDKKNIITKINDIKISEENNNDIKYLPSFSKVLP
EILNLYRNNPKNEPFDTIETEKIVLNALIYVNKELYKKLILEDDLEENESKNIFLQELKKTLGNIDEIDENIIENY
YKNAQISASKGNNKAIKKYQKKVIECYIGYLRKNYEELFDESDFKMNIQEIKKQIKDINDNKTYERITVKTSDKTI
VINDDFEYIISIFALLNSNAVINKIRNRFFATSVWLNTSEYQNIIDILDEIMQLNTLRNECITENWNLNLEEFIQK
MKEIEKDFDDFKIQTKKEIFNNYYEDIKNNILTEFKDDINGCDVLEKKLEKIVIFDDETKFEIDKKSNILQDEQRK
```

TABLE 1-continued

Polynucleotide and Polypeptide Sequences of Cas Constructs

LSNINKKDLKKKVDQYIKDKDQEIKSKILCRIIFNSDFLKKYKKEIDNLIEDMESENENKFQEIYYPKERKNELYI
YKKNLFLNIGNPNFDKIYGLISNDIKMADAKFLFNIDGKNIRKNKISEIDAILKNLNDKLNGYSKEYKEKYIKKLK
ENDDFFAKNIQNKNYKSFEKDYNRVSEYKKIRDLVEFNYLNKIESYLIDINWKLAIQMARFERDMHYIVNGLRELG
IIKLSGYNTGISRAYPKRNGSDGFYTTTAYYKFFDEESYKKFEKICYGFGIDLSENSEINKPENESIRNYISHFYI
VRNPFADYSIAEQIDRVSNLLSYSTRYNNSTYASVFEVFKKDVNLDYDELKKKFKLIGNNDILERLMKPKKVSVLE
LESYNSDYIKNLIIELLTKIENTNDTLDPNSSSVDKLAAALEHHHHH

LwaCas13a CTD-His Polynucleotide Sequence

SEQ ID NO: 9

ATGAAAGTGACCAAAGTGGATGGCATCAGCCACAAAAAATACATCGAAGAAGGCAAACTGGTTAAAAGCACCAGCG
AAGAAAATCGTACCAGCGAACGTCTGAGCGAACTGCTGAGCATTCGTCTGGATATCTATATCAAAAATCCGGATAA
TGCCAGCGAGGAAGAAAACCGTATTCGTCGTGAAAACCTGAAAAAGTTCTTCAGCAATAAAGTGCTGCACCTGAAA
GATAGCGTTCTGTATCTGAAAAACCGCAAAGAAAAAAATGCCGTGCAGGACAAAAACTATAGCGAAGAGGATATCA
GCGAGTATGACCTGAAGAACAAAAATAGCTTTAGCGTGCTGAAAAAAATCCTGCTGAATGAAGATGTGAATAGCGA
GGAACTGGAAATCTTTCGTAAAGATGTTGAAGCCAAGCTGACAAAATCAACAGCCTGAAATATAGCTTTGAAGAA
AACAAGGCCAACTATCAGAAAATCAACGAGAACAACGTGGAAAAAGTTGGTGGTAAAAGCAAACGCAACATCATCT
ATGATTATTATCGCGAAAGCGCGAAACGCAACGATTATATCAATAATGTGCAAGAGGCCTTCGACAAACTGTACAA
AAAAGAGGACATCGAAAAACTGTTTTTTCTGATCGAGAACAGCAAGAAGCACGAGAAATACAAAATCCGCGAGTAC
TACCATAAAATCATCGGTCGCAAAAACGATAAAGAGAACTTCGCCAAAATCATCTACGAAGAAATTCAGAACGTGA
ACAACATCAAAGAACTGATCGAAAAAATTCCGGACATGAGCGAGCTGAAGAAAGCCAGGTGTTCTATAAATACTA
CCTGGACAAAGAGGAACTGAACGACAAAAACATCAAATATGCCTTTTGCCACTTCGTCGAAATTGAAATGAGCCAG
CTGCTTAAAAACTACGTGTATAAACGCCTGAGCAACATCAGCAACGATAAAATCAAACGTATCTTTGAATATCAGA
ATCTGAAGAAACTGATTGAAAACAAACTGCTGAACAAGCTGGATACCTATGTTCGTAATTGCGGCAAATACAACTA
CTATCTGCAGGTTGGTGAAATTGCAACCAGCGATTTTATTGCACGTAATCGTCAGAATGAAGCCTTTCTGCGTAAC
ATTATTGGTGTTAGCAGCGTTGCATATTTTAGCCTGCGTAATATTCTGGAAACCGAAAACGAAATGGCATTACCG
GTCCGTATGCGTGGTAAAACCGTTAAAAACAATAAAGGCGAAGAGAAGTATGTGAGCGGTGAAGTGGATAAAATCTA
TAACGAAAACAAGCAGAACGAAGTGAAAGAAAATCTGAAAATGTTTTACAGCTACGACTTCAACATGGACAACAAA
AACGAGATCGAAGATTTCTTCGCCAACATTGATGAAGCCATTAGCAGTATTCGTCATGGCATTGTGCACTTTAATC
TGGAACTTGAAGGCAAAGACATCTTCGCGTTTAAAAACATTGCACCGAGCGAGATCAGCAAAAAAATGTTTCAGAA
CGAGATTAACGAAAAAAACTGAAACTGAAATCTTCAAACAGCTGAATAGCGCCAACGTGTTCAACTATTATGAG
AAAGACGTGATCATCAAATACCTTAAAAACACCAAATTCAACTTCGTGAATAAAAACATCCCGTTTGTTCCGAGCT
TCACCAAACTGTATAACAAAATTGAAGATCTGCGCAATACCCTGAAGTTTTTTTGGAGCGTTCCGAAAGACAAAGA
AGAAAAAGACGCACAGATCTACCTGCTTAAGAACATCTATTATGGCGAATTTCTGAACAAATTCGTGAAAAATAGC
AAAGTGTTCTTCAAATCACCAACGAGGTGATCAAGATTAACAAACAGCGTAATCAGAAAACCGGTCACTACAAAT
ACCAGAAGTTTGAGAACATTGAAAAAACCGTGCCGGTTGAATATCTGGCAATTATTCAGAGCCGTGAGATGATTAA
CAACCAGGATAAAGAAGAGAAAAACACCTACATCGATTTCATCCAGCAGATCTTTCTGAAAGGCTTTATCGATTAC
CTGAACAAGAACAACCTGAAGTATATCGAGTCGAACAACAATAACGACAACAACGACATCTTTAGCAAAATCAAAA
TCAAGAAAGATAATAAAGAAAAATACGAACAAGATTCCTGAAAAACTATGAGAAGCACAACCGCAACAAAGAAATTCC
GCATGAGATCAATGAATTTGTGCGCGAAATTAAACTGGGCAAATCCTGAAATACACCGAGAACCTGAATATGTTC
TATCTGATTCTGAAGCTGCTGAACCATAAAGAGCTGACCAATCTGAAAGGTAGCCTGGAAAAATATCAGAGCGCAA
ACAAGAAGAGACATTTTCTGACGAACTGGAACTGATTAATCTGCTGAATCTGGATAATAACCGTGTGACCGAAGA
TTTTGAACTGGAAGCAAATGAAATCGGCAAATTCCTGGATTTCAATGAGAACAAAATTAAGGACCGGAAAGAGCTT
AAAAAGTTTGATACCAACAAAATCTACTTCGACGGCGAGAACATTATCAAACATCGTGCCTTTTATAACATCAAAA
AGTATGGCATGCTGAACCTGCTGGAAAAAATTGCAGATAAAGCCAAGTACAAAATTAGCCTGAAAGAACTTAAAGA
GTACAGCAACAAAAAGAACGAAATCGAGAAGAACTATACCATGCAGCAGAATCTGCATCGTAAATATGCACGTCCG
AAAAAAGACGAGAAATTCAACGATGAGGACTATAAAGAATACGAGAAAGCCATTGGCAACATCCAGAAATATACCC
ACTTGAAAAACAAAGTGGAATTTAACGAGCTGAATTTACTGCAGGGTCTGCTGCTGAAAATTCTGCACCGTCTGGT
TGGTTATACCAGCATTTGGGAACGTGATCTGCGTTTTCGCCTGAAAGGTGAATTTCCTGAAAACCACTATATCGAG
GAAATTTTCAACTTTGACAACAGCAAAAACGTGAAATATAAGAGCGGTCAGATCGTCGAAAAGTACATCAACTTTT
ACAAAGAACTTTACAAGGATAATGTGGAAAAACGCAGCATCTACAGCGACAAGAAAGTGAAAAAGCTGAAGCAAGA
AAAGAAAGACCTGTACATCCGTAATTATATCGCCCACTTTAACTATATCCCGCATGCAGAAATTAGTCTGCTGGAA
GTTCTGGAAAATCTGCGTAAACTGCTGTCATATGATCGCAAACTGAAGAACGCAATCATGAAAGCATTGTGGATA
TCCTGAAAGAGTATGGTTTTGTCGCCACCTTTAAAATCGGTGCCGATAAGAAAATTGAGATTCAGACCCTGGAAAG
CGAGAAAATTGTGCATCTTAAGAACCTTAAAAAGAAAAAACTGATGACCGATCGCAACAGCGAAGAGTTATGTGAA
CTGGTGAAAGTGATGTTCGAATACAAAGCACTGGAAGGGGATCCGAATTCGAGCTCCGTCGACAAGCTTGCGGCCG
CACTCGAGCACCACCACCACCACCACTGA

LwaCas13a CTD-His Polypeptide Sequence

SEQ ID NO: 10

MKVTKVDGISHKKYIEEGKLVKSTSEENRTSERLSELLSIRLDIYIKNPDNASEEENRIRRENLKKFFSNKVLHLK
DSVLYLKNRKEKNAVQDKNYSEEDISEYDLKNKNSFSVLKKILLNEDVNSEELEIFRKDVEAKLNKINSLKYSFEE
NKANYQKINENNVEKVGGKSKRNIIYDYYRESAKRNDYINNVQEAFDKLYKKEDIEKLFFLIENSKKHEKYKIREY
YHKIIGRKNDKENFAKIIYEEIQNVNNIKELIEKIPDMSELKKSQVFYKYYLDKEELNDKNIKYAFCHFVEIEMSQ
LLKNYVYKRLSNISNDKIKRIFEYQNLKKLIENKLLNKLDTYVRNCGKYNYYLQVGEIATSDFIARNRQNEAFLRN
IIGVSSVAYFSLRNILETENENGITGRMRGKTVKNNKGEEKYVSGEVDKIYNENKQNEVKENLKMFYSYDENMDNK
NEIEDFFANIDEAISSIRHGIVHFNLELEGKDIFAFKNIAPSEISKKMFQNEINEKKLKLKIFKQLNSANVENYYE
KDVIIKYLKNTKFNFVNKNIPFVPSFTKLYNKIEDLRNTLKFFWSVPKDKEEKDAQIYLLKNIYYGEFLNKFVKNS
KVFFKITNEVIKINKQRNQKTGHYKYQKFENIEKTVPVEYLAIIQSREMINNQDKEEKNTYIDFIQQIFLKGFIDY
LNKNNLKYIESNNNNDNNDIFSKIKIKKDNKEKYDKILKNYEKHNRNKEIPHEINEFVREIKLGKILKYTENLNMF
YLILKLLNHKELTNLKGSLEKYQSANKEETFSDELELINLLNLDNNRVTEDFELEANEIGKELDENENKIKDRKEL
KKFDTNKIYFDGENIIKHRAFYNIKKYGMLNLLEKIADKAKYKISLKELKEYSNKKNEIEKNYTMQQNLHRKYARP
KKDEKFNDEDYKEYEKAIGNIQKYTHLKNKVEFNELNLLQGLLLKILHRLVGYTSIWERDLRFRLKGEFPENHYIE
EIFNFDNSKNVKYKSGQIVEKYINFYKELYKDNVEKRSIYSDKKVKKLKQEKKDLYIRNYIAHFNYIPHAEISLLE
VLENLRKLLSYDRKLKNAIMKSIVDILKEYGFVATFKIGADKKIEIQTLESEKIVHLKNLKKKKLMTDRNSEELCE
LVKVMFEYKALEGDPNSSSVDKLAAALEHHHHHH

TABLE 1-continued

Polynucleotide and Polypeptide Sequences of Cas Constructs

LwaCas13a NTD-MBP Polynucleotide Sequence

SEQ ID NO: 11

```
ATGAAAATCGAAGAAGGTAAACTGGTAATCTGGATTAACGGCGATAAAGGCTATAACGGTCTCGCTGAAGTCGGTA
AGAAATTCGAGAAAGATACCGGAATTAAAGTCACCGTTGAGCATCCGGATAAACTGGAAGAGAAATTCCCACAGGT
TGCGGCAACTGGCGATGGCCCTGACATTATCTTCTGGGCACACGACCGCTTTGGTGGCTACGCTCAATCTGGCCTG
TTGGCTGAAATCACCCCGGACAAAGCGTTCCAGGACAAGCTGTATCCGTTTACCTGGGATGCCGTACGTTACAACG
GCAAGCTGATTGCTTACCCGATCGCTGTTGAAGCGTTATCGCTGATTTATAACAAAGATCTGCTGCCGAACCCGCC
AAAAACCTGGGAAGAGATCCCGGCGCTGGATAAAGAACTGAAAGCGAAAGGTAAGAGCGCGCTGATGTTCAACCTG
CAAGAACCGTACTTCACCTGGCCGCTGATTGCTGCTGACGGGGGTTATGCGTTCAAGTATGAAAACGGCAAGTACG
ACATTAAAGACGTGGGCGTGGATAACGCTGGCGCGAAAGCGGGTCTGACCTTCCTGGTTGACCTGATTAAAAACAA
ACACATGAATGCAGACACCGATTACTCCATCGCAGAAGCTGCCTTTAATAAAGGCGAAACAGCGATGACCATCAAC
GGCCCGTGGGCATGGTCCAACATCGACACCAGCAAAGTGAATTATGGTGTAACGGTACTGCCGACCTTCAAGGGTC
AACCATCCAAACCGTTCGTTGGCGTGCTGAGCGCAGGTATTAACGCCGCCAGTCCGAACAAAGAGCTGGCAAAAGA
GTTCCTCGAAAACTATCTGCTGACTGATGAAGGTCTGGAAGCGGTTAATAAAGACAAACCGCTGGGTGCCGTAGCG
CTGAAGTCTTACGAGGAAGAGTTGGTGAAAGATCCGCGTATTGCCGCCACTATGGAAAACGCCCAGAAAGGTGAAA
TCATGCCGAACATCCCGCAGATGTCCGCTTTCTGGTATGCCGTGCGTACTGCGGTGATCAACGCCGCCAGCGGTCG
TCAGACTGTCGATGAAGCCCTGAAAGACGCGCAGACTAATTCGAGCTCGAACAACAACAACAATAACAATAACAAC
AACCTCGGGATCGAGGGAAGgAAAGTGACCAAAGTGGATGGCATCAGCCACAAAAATACATCGAAGAAGGCAAAC
TGGTTAAAAGCACCAGCGAAGAAAATCGTACCAGCGAACGTCTGAGCGAACTGCTGAGCATTCGTCTGGATATCTA
TATCAAAAATCCGGATAATGCCAGCGAGGAAGAAAACCGTATTCGTCGTGAAAACCTGAAAAAGTTCTTCAGCAAT
AAAGTGCTGCACCTGAAAGATAGCGTTCTGTATCTGAAAAACCGCAAAGAAAAAAATGCCGTGCAGGACAAAAACT
ATAGCGAAGAGGATATCAGCGAGTATGACCTGAAGAACAAAAATAGCTTTAGCGTGCTGAAAAAAATCCTGCTGAA
TGAAGATGTGAATAGCGAGGAACTGGAAATCTTTCGTAAAGATGTTGAAGCCAAGCTGAACAAAATCAACAGCCTG
AAATATAGCTTTGAAGAAAACAAGGCCAACTATCAGAAAATCAACGAGAACAACGTGGAAAAAGTTGGTGGTAAAA
GCAAACGCAACATCATCTATGATTATTATCGCGAAAGCGCGAAACGCAACGATTATATCAATAATGTGCAAGAGGC
CTTCGACAAACTGTACAAAAAAGAGGACATCGAAAAAATCGTTTTTTCTGATCGAACAGCAAGAAGCACGAGAAA
TACAAAATCCGCGAGTACTACCATAAAAATCATCGGTCGCAAAAACGTAAAAGAGAACTTCGCCAAAATCATCTACG
AAGAAATTCAGAACGTGAACAACATCAAAGAACTGATCGAAAAAATTCCGGACATGAGCGAGCTGAAGAAAAGCCA
GGTGTTCTATAAATACTACCTGGACAAAGAGGAACTGAACGACAAAAACATCAAATATGCCTTTTGCCACTTCGTC
GAAATTGAAATGAGCCAGCTGCTTAAAAACTACGTGTATAAACGCCTGAGCAACATCAGCAACGATAAAATCAAAC
GTATCTTTGAATATCAGAATCTGAAGAAACTGATTGAAAACAAACTGCTGAACAAGCTGGATACCTATGTTCGTAA
TTGCGGCAAATACAACTACTATCTGCAGGTTGGTGAAATTGCAACCAGCGATTTTATTGCACGTAATCGTCAGAAT
GAAGCCTTTCTGCGTAACATTATTGGTGTTAGCAGCGTTGCATATTTTAGCCTGCGTAATATTCTGGAAACCGAAA
ACGAAAATGGTATTACCGGTCGTATGCGTGGTAAAACCGTTAAAAACAATAAAGGCGAAGAGAAGTATGTGAGCGG
TGAAGTGGATAAAATCTATAACGAAAACAAGCAGAACGAAGTGAAAAGAATCTGAAAATGTTTTACAGCTACGAC
TTCAACATGGACAACAAAAACGAGATCGAAGATTTCTTCGCCAACATTGATGAAGCCATTAGCAGTATTCGTCATG
GCATTGTGCACTTTAATCTGGAACTTGAAGGCAAAGACATCTTCGCGTTTAAAAACATTGCACCGAGCGAGATCAG
CAAAAAAATGTTTCAGAACGAGATTAACGAAAAAAACTGAAACTGAAAATCTTCAAACAGCTGAATAGCGCCAAC
GTGTTCAACTATTATGAGAAAGACGTGATCATCAAATACCTTAAAAACACCAAATTCAACTTCGTGAATAAAAACA
TCCCGTTTGTTCCGAGCTTCACCAAACTGTATAACAAAATTGAAGATCTGCGCAATACCCTGAAGTTTTTTTGGAG
CGTTCCGAAAGACAAAGAAGAAAAGACGCACAGATCTACCTGCTTAAGAACATCTATTATGGCGAATTTCTGAAC
AAATTCGTGAAAAATAGCAAAGTGTTCTTCAAAATCACCAACGAGGTGATCAAGATTAACAAACAGCGTAATCAGA
AAACCGGTCACTACAAATACCAGAAGTTTGAGAACATTGAAAAAACCGTGCCGGTTGAATATCTGGCAATTATTCA
GAGCCGTGAGATGATTAACAACCAGGATAAAGAAGAGAAAAACACCTACATCGATTTCATCCAGCAGATCTTTCTG
AAAGGCTTTATCGATTACCTGAACAAGAACAACCTGAAGTATATCGAGTCGAACAACAATAACGACAACAACGACA
TCTTTAGCAAAATCAAAATCAAGAAAGATAATAAAGAAAAATACGACAAGATCCTGAAAAACTATGAGAAGCACAA
CCGCACAAAGAAATTCCGCATGAGATCAATGAATTTGTGCGCGAAATTAAACTGGGCAAAATCCTGAAATACACC
GAGAACCTGAATATGTTCTATCTGATTCTGAAGCTGCTGAACCATAAAGAGCTGACCAATCTGAAAGGTAGCCTGG
AAAAATATCAGAGCGCAAACAAGAAGAGACATTTTCTGACGAACTGGAACTGATTAATCTGCTGAATCTGGATAA
TAACCGTGTGACCGAAGATTTTGAACTGGAAGCAAATGAAATCGGCAAATTCCTGGATTTCAATGAGAACAAAATT
AAGGACCGGAAAGAGCTTAAAAAGTTTGATACCAACAAAATCTACTTCGACGCGGAGAACATTATCAAACATCGTG
CCTTTTATAACATCAAAAAGTATGGCATGCTGAACCTGCTGGAAAAAATTGCAGATAAAGCCAAGTACAAAATTAG
CCTGAAAGAACTTAAAGAGTACAGCAACAAAAGAACGAAATCGAGAAGAACTATACCATGCAGCAGAATCTGCAT
CGTAAATATGCACGTCCGAAAAAAGACGAGAAATTCAACGATGAGGACTATAAAGAATACGAGAAAGCCATTGGCA
ACATCCAGAAATATACCCACTTGAAAAACAAAGTGGAATTTAACGGTGAATTTTACTGCAGGGTCTGCTGCTGAA
AATTCTGCACCGTCTGGTTGGTTATACCAGCATTTGGGAACGTGATCTGCGTTTTCGCCTGAAAGGTGAATTTCCT
GAAAACCACTATATCGAGGAAATTTTCAACTTTGACAACAGCAAAAACGTGAAATATAAGAGCGGTCAGATCGTCG
AAAAGTACATCAACTTTTACAAAGAACTTTACAAGGATAATGTGGAAAAACGCAGCATCTACAGCGACAAGAAAGT
GAAAAAGCTGAAGCAAGAAAAAGAAGACCTGTACATCCGTAATTATATCGCCCACTTTAACTATATCCCGCATGCA
GAAATTAGTCTGCTGGAAGTTCTGGAAAATCTGCGTAAACTGCTGTCTATATGATCGAAACTGAAGAACGCAATCA
TGAAAAGCATTGTGGATATCCTGAAAGAGTATGGTTTTGTCGCCACCTTTAAATCGGTGCCGATAAGAAATTGA
GATTCAGACCCTGGAAAGCGAGAAATTGTGCATCTTAAGAACCTTAAAAAGAAAAACTGATGACCGATCGCAAC
AGCGAAGAGTTATGTGAACTGGTGAAAGTGATGTTCGAATACAAAGCACTGGAAGATCCGAATTCGAGCTCCGTCG
ACAAGCTTGCGGCCGCACTCGAGCACCACCACCACCACCACTGA
```

LwaCas13a NTD-MBP Polypeptide Sequence

SEQ ID NO: 12

```
MKIEEGKLVIWINGDKGYNGLAEVGKKFEKDTGIKVTVEHPDKLEEKFPQVAATGDGPDIIFWAHDRFGGYAQSGL
LAEITPDKAFQDKLYPFTWDAVRYNGKLIAYPIAVEALSLIYNKDLLPNPPKTWEEIPALDKELKAKGKSALMENL
QEPYFTWPLIAADGGYAFKYENGKYDIKDVGVDNAGAKAGLTFLVDLIKNKHMNADTDYSIAEAAFNKGETAMTIN
GPWAWSNIDTSKVNYGVTVLPTFKGQPSKPFVGVLSAGINAASPNKELAKEFLENYLLTDEGLEAVNKDPLGAVA
LKSYEEELVKDPRIAATMENAQKGEIMPNIPQMSAFWYAVRTAVINAASGRQTVDEALKDAQTNSSSNNNNNNNN
NLGIEGRKVTKVDGISHKKYIEEGKLVKSTSEENRTSERLSELLSIRLDIYIKNPDNASEEENRIRRENLKKFFSN
KVLHLKDSVLYLKNRKEKNAVQDKNYSEEDISEYDLKNKNSFSVLKKILLNEDVNSEELEIFRKDVEAKLNKINSL
KYSFEENKANYQKINENNVEKVGGKSKRNIIYDYYRESAKRNDYINNVQEAFDKLYKKEDIEKLFFLIENSKKHEK
YKIREYYHKIIGRKNDKENFAKIIYEEIQNVNNIKELIEKIPDMSELKKSQVFYKYYLDKEELNDKNIKYAFCHFV
EIEMSQLLKNYVYKRLSNISNDKIKRIFEYQNLKKLIENKLLNKLDTYVRNCGKYNYYLQVGEIATSDFIARNRQN
```

TABLE 1-continued

Polynucleotide and Polypeptide Sequences of Cas Constructs

EAFLRNIIGVSSVAYFSLRNILETENENGITGRMRGKTVKNNKGEEKYVSGEVDKIYNENKQNEVKENLKMFYSYD
FNMDNKNEIEDFFANIDEAISSIRHGIVHENLELEGKDIFAFKNIAPSEISKKMFQNEINEKKLKLKIFKQLNSAN
VFNYYEKDVIIKYLKNTKFNFVNKNIPFVPSFTKLYNKIEDLRNTLKFFWSVPKDKEEKDAQIYLLKNIYYGEFLN
KFVKNSKVFFKITNEVIKINKQRNQKTGHYKYQKFENIEKTVPVEYLAIIQSREMINNQDKEEKNTYIDFIQQIFL
KGFIDYLNKNNLKYIESNNNNDNNDIFSKIKIKKDNKEKYDKILKNYEKHNRNKEIPHEINEFVREIKLGKILKYT
ENLNMFYLILKLLNHKELTNLKGSLEKYQSANKEETFSDELELINLLNLDNNRVTEDFELEANEIGKELDENENKI
KDRKELKKFDTNKIYFDGENIIKHRAFYNIKKYGMLNLLEKIADKAKYKISLKELKEYSNKKNEIEKNYTMQQNLH
RKYARPKKDEKENDEDYKEYEKAIGNIQKYTHLKNKVEFNELNLLQGLLLKILHRLVGYTSIWERDLRFRLKGEFP
ENHYIEEIFNFDNSKNVKYKSGQIVEKYINFYKELYKDNVEKRSIYSDKKVKKLKQEKKDLYIRNYIAHFNYIPHA
EISLLEVLENLRKLLSYDRKLKNAIMKSIVDILKEYGFVATFKIGADKKIEIQTLESEKIVHLKNLKKKKLMTDRN
SEELCELVKVMFEYKALEDPNSSSVDKLAAALEHHHHHH

LwaCas13a G403D CTD-His Polynucleotide Sequence
SEQ ID NO: 13

ATGAAAGTGACCAAAGTGGATGGCATCAGCCACAAAAAATACATCGAAGAAGGCAAACTGGTTAAAAGCACCAGCG
AAGAAAATCGTACCAGCGAACGTCTGAGCGAACTGCTGAGCATTCGTCTGGATATCTATATCAAAAATCCGGATAA
TGCCAGCGAGGAAGAAAACCGTATTCGTCGTGAAAACCTGAAAAAGTTCTTCAGCAATAAAGTGCTGCACCTGAAA
GATAGCGTTCTGTATCTGAAAAACCGCAAAGAAAAAAATGCCGTGCAGGACAAAAACTATAGCGAAGAGGATATCA
GCGAGTATGACCTGAAGAACAAAAATAGCTTTAGCGTGCTGAAAAAAATCCTGCTGAATGAAGATGTGAATAGCGA
GGAACTGGAAATCTTTCGTAAAGATGTTGAAGCCAAGCTGAACAAAATCAACAGCCTGAAATATAGCTTTGAAGAA
AACAAGGCCAACTATCAGAAAATCAACGAGAACAACGTGGAAAAAGTTGGTGGTAAAAGCAAACGCAACATCATCT
ATGATTATTATCGCGAAAGCGCGAAACGCAACGATTATATCAATAATGTGCAAGAGGCCTTCGACAAACTGTACAA
AAAAGAGGACATCGAAAAACTGTTTTTTCTGATCGAGAACGACCAAGAAGCACGAAGAAAATCGAGTAC
TACCATAAAATCATCGGTCGCAAAAACGATAAAGAGAACTTCGCCAAAATCATCTACGAAGAAATTCAGAACGTGA
ACAACATCAAAGAACTGATCGAAAAAATTCCGGACATGAGCGAGCTGAAGAAAAGCCAGGTGTTCTATAAATACTA
CCTGGACAAAGAGGAACTGAACGACAAAAACATCAAATATGCCTTTTGCCACTTCGTCGAAATTGAAATGAGCCAG
CTGCTTAAAAACTACGTGTATAAACGCCTGAGCAACATCAGCAACGATAAAATCAACGTATCTTTGAATATCAGA
ATCTGAAGAAACTGATTGAAAACAAACTGCTGAACAAGCTGGATACCTATGTTCGTAATTGCGGCAAATACAACTA
CTATCTGCAGGTTGGTGAAATTGCAACCAGCGATTTTATTGCACGTAATCGTCAGAATGAAGCCTTTCTGCGTAAC
ATTATTGGTGTTAGCAGCGTTGCATATTTTAGCCTGCGTAATATTCTGGAAACCGAAAACGAAAATGATATTACCG
GTCGTATGCGTGGTAAAACCGTTAAAAACAATAAAGGCGAAGAGAAGTATGTGAGCGGTGAAGTGGATAAAATCTA
TAACGAAAACAAGCAGAACGAAGTGAAAGAAAATCTGAAAATGTTTTACAGCTACGACTTCAACATGGACAACAAA
AACGAGATCGAAGATTTCTTCGCCAACATTGATGAAGCCATTAGCAGTATTCGTCATGGCATTGTGCACTTTAATC
TGGAACTTGAAGGCAAAGACATCTTCGCGTTTAAAAACATTGCACCGAGCGAGATCAGCAAAAAATGTTTCAGAA
CGAGATTAACGAAAAAAACTGAAACTGAAATCTTCAAACAGCTGAATAGCGCCAACGTGTTCAACTATTATGAG
AAAGACGTGATCATCAAATACCTTAAAAACACCAAATTCAACTTCGTGAATAAAAACATCCCGTTTGTTCCGAGCT
TCACCAAACTGTATAACAAAATTGAAGATCTGCGCAATACCCTGAAGTTTTTTGGAGCGTTCCGAAAGACAAAGA
AGAAAAAGACGCACAGATCTACCTGCTTAAGAACATCTATTATGGCGAATTTCTGAACAAATTCGTGAAAAATAGC
AAAGTGTTCTTCAAAATCACCAACGAGGTGATCAAGATTAACAAACAGCGTAATCAGAAAACCGGTCACTACAAAT
ACCAGAGTTTGAGAACATTGAAAAAACCGTGCCGGTTGAATATCTGGCAATTATTCAGAGCCGTGAGATGATTAA
CAACCAGGATAAAGAAGAGAAAAACACCTACATCGATTTCATCCAGCAGATCTTTCTGAAAGGCTTTATCGATTAC
CTGAACAAGAACAACCTGAAGTATATCGAGTCGAACAACAATAACGACAACAACGACATCTTTAGCAAAATCAAAA
TCAAGAAAGATAATAAAGAAAAATACGACAAGATCCTGAAAAACTATGAGAAGCACAACCGCAACAAAGAAATTCC
GCATGAGATCAATGAATTTGTGCGCGAAATTAAACTGGGCAAAATCCTGAAATACACCCAGAACCTGAATATGTTC
TATCTGATTCTGAAGCTGCTGAACCATAAAGAGCTGACCAATCTGAAAGGTAGCCTGGAAAAATATCAGAGCGCAA
ACAAAGAAGAGACATTTCTGACGAACTGGAACTGATTAATCTGCTGAATCTGGATAATAACCGTGTGACCGAAGA
TTTTGAACTGGAAGCAAATGAAATCGGCAAATTCCTGGATTTCAATGAGAACAAAATTAAGGACCGGAAAGAGCTT
AAAAAGTTTGATACCAACAAAATCTACTTCGACGGCGAGAACATTATCAAACATCGTGCCTTTTATAACATCAAAA
AGTATGGCATGCTGAACCTGCTGGAAAAAATTGCAGATAAAGCCAAGTACAAAATTAGCCTGAAAGAACTTAAAGA
GTACAGCAACAAAAAGAACGAAATCGAGAAGAACTATACCATGCAGCAGAATCTGCATCGTAAATATGCACGTCCG
AAAAAAGACGAGAAATTCAACGATGAGGACTATAAAGAATACGAGAAAGCCATTGGCAACATCCAGAAATATACCC
ACTTGAAAAACAAAGTGGAATTTAACGAGCTGAATTTACTGCAGGGTCTGCTGCTGAAAATTCTGCACCGTCTGGT
TGGTTATACCAGCATTTGGGAACGTGATCTGCGCTTTCGCCTGAAAGGTGAATTTCCTGAAAACCACTATATCGAG
GAAATTTTCAACTTTGACAACAGCAAAAACGTGAAATATAAGAGCGGTCAGATCGTCGAAAAGTACATCAACTTTT
ACAAAGAACTTTACAAGGATAATGTGGAAAAACGCAGCATCTACAGCGACAAGAAGTGAAAAAGCTGAAGCAAGA
AAAGAAAGACCTGTACATCCGTAATTATATCGCCCACTTTAACTATATCCCGCATGCAGAAATTAGTCTGCTGGAA
GTTCTGGAAAATCTGCGTAAACTGCTGTCATATGATCGCAAACTGAAGAACGCAATCATGAAAAGCATTGTGGATA
TCCTGAAAGAGTATGGTTTTGTCGCCACCTTTAAAATCGGTGCCGATAAGAAAATTGAGATTCAGACCCTGGAAAG
CGAGAAAATTGTGCATCTTAAGAACCTTAAAAAGAAAAAACTGATGACCGATCGCAACAGCGAAGAGTTATGTGAA
CTGGTGAAAGTGATGTTCGAATACAAAGCACTGGAAGGGGATCCGAATTCGAGCTCCGTCGACAAGCTTGCGGCCG
CACTCGAGCACCACCACCACCACCACTGA

LwaCas13a G403D CTD-His Polypeptide Sequence
SEQ ID NO: 14

MKVTKVDGISHKKYIEEGKLVKSTSEENRTSERLSELLSIRLDIYIKNPDNASEEENRIRRENLKFFSNKVLHLK
DSVLYLKNRKEKNAVQDKNYSEEDISEYDLKNKNSFSVLKKILLNEDVNSEELEIFRKDVEAKLNKINSLKYSFEE
NKANYQKINENNVEKVGGKSKRNIIYDYYRESAKRNDYINNVQEAFDKLYKKEDIEKLFFLIENSKKHEKYKIREY
YHKIIGRKNDKENFAKIIYEEIQNVNNIKELIEKIPDMSELKKSQVFYKYYLDKEELNDKNIKYAFCHFVEIEMSQ
LLKNYVVKRLSNISNDKIKRIFEYQNLKKLIENKLLNKLDTYVRNCGKYNYYLQVGEIATSDFIARNRQNEAFLRN
IIGVSSVAYFSLRNILETENENDITGRMRGKTVKNNKGEEKYVSGEVDKIYNENKQNEVKENLKMFYSYDENMDNK
NEIEDFFANIDEAISSIRHGIVHENLELEGKDIFAFKNIAPSEISKKMFQNEINEKKLKLKIFKQLNSANVENYYE
KDVIIKYLKNTKFNFVNKNIPFVPSFTKLYNKIEDLRNTLKFFWSVPKDKEEKDAQIYLLKNIYYGEFLNKFVKNS
KVFFKITNEVIKINKQRNQKTGHYKYQKFENIEKTVPVEYLAIIQSREMINNQDKEEKNTYIDFIQQIFLKGFIDY
LNKNNLKYIESNNNNDNNDIFSKIKIKKDNKEKYDKILKNYEKHNRNKEIPHEINEFVREIKLGKILKYTENLNMF
YLILKLLNHKELTNLKGSLEKYQSANKEETFSDELELINLLNLDNNRVTEDFELEANEIGKFLDENENKIKDRKEL
KKFDTNKIYFDGENIIKHRAFYNIKKYGMLNLLEKIADKAKYKISLKELKEYSNKKNEIEKNYTMQQNLHRKYARP
KKDEKFNDEDYKEYEKAIGNIQKYTHLKNKVEFNELNLLQGLLLKILHRLVGYTSIWERDLRFRLKGEFPENHYIE
EIFNFDNSKNVKYKSGQIVEKYINFYKELYKDNVEKRSIYSDKKVKKLKQEKKDLYIRNYIAHFNYIPHAEISLLE

TABLE 1-continued

Polynucleotide and Polypeptide Sequences of Cas Constructs

VLENLRKLLSYDRKLKNAIMKSIVDILKEYGFVATFKIGADKKIEIQTLESEKIVHLKNLKKKKLMTDRNSEELCE
LVKVMFEYKALEGDPNSSSVDKLAAALEHHHHHH

| | |
|---|---|
| LbuCas13a-CTD-His Vector (pET28b) | SEQ ID NO: 36 |
| LbuCas13a-NTD-MBP Vector (pET28b-MBP-TEV) | SEQ ID NO: 37 |
| LshCas13a-NTD-His Vector (pET28b) | SEQ ID NO: 38 |
| LshCas13a-NTD-MBP Vector (pET28b-MBP-TEV) | SEQ ID NO: 39 |
| LwaCas13a-CTD-His Vector (pET28b) | SEQ ID NO: 40 |
| LwaCas13a-NTD-MBP Vector (pET28b-MBP-TEV) | SEQ ID NO: 41 |
| LwaCas13a G403D-CTD-His Vector (pET28b) | SEQ ID NO: 42 |
| pET28b | SEQ ID NO: 43 |
| pET28-MBP-TEV | SEQ ID NO: 44 |

TABLE 2

Sequences of primers used for isothermal assembly (ISO).

| Primer Name | Sequence (5'→3') | SEQ ID NO |
|---|---|---|
| Lbu 5' for pET28 ISO | GAAATAATTTTGTTTAACTTTAAGAAGGAGATATACC ATGAAGGTGACCAAAGTTGGTGG | SEQ ID NO: 15 |
| Lbu 3' for pET28 ISO | CGGCCGCAAGCTTGTCGACGGAGCTCGAATTCGGATC CCCATTTTCGGATTTCTTCTCTTCCATTTTATACTC | SEQ ID NO: 16 |
| Lbu 5' for pMAL ISO | AATAACAATAACAACAACCTCGGGATCGAGGGAAGGA AGGTGACCAAAGTTGGTGGTATC | SEQ ID NO: 17 |
| Lbu 3' for pMAL ISO | GTGCGGCCGCAAGCTTGTCGACGGAGCTCGAATTCGG ATCATTTTCGGATTTCTTCTCTTCCATTTTATACTC | SEQ ID NO: 18 |
| Lsh 5' for pET28 ISO | ATAATTTTGTTTAACTTTAAGAAGGAGATATACCATG GGTAACCTGTTTGGTCATAAACG | SEQ ID NO: 19 |
| Lsh 3' for pET28 ISO | CGGCCGCAAGCTTGTCGACGGAGCTCGAATTCGGATC CCCCAGGGTATCATTGGTATTTTCAATCTTGG | SEQ ID NO: 20 |
| Lsh 5' for pMAL ISO | TAACAATAACAACAACCTCGGGATCGAGGGAAGGGGT AACCTGTTTGGTCATAAACGTTG | SEQ ID NO: 21 |
| Lsh 3' for pMAL ISO | GTGCGGCCGCAAGCTTGTCGACGGAGCTCGAATTCGG ATCCAGGGTATCATTGGTATTTTCAATCTTGG | SEQ ID NO: 22 |
| Lwa 5' for pET28 ISO | AAATAATTTTGTTTAACTTTAAGAAGGAGATATACCA TGAAAGTGACCAAAGTGGATGG | SEQ ID NO: 23 |
| Lwa 3' for pET28 ISO | GCAAGCTTGTCGACGGAGCTCGAATTCGGATCCCCTT CCAGTGCTTTGTATTCGAACATC | SEQ ID NO: 24 |
| Lwa 5' for pMAL ISO | ACAATAACAATAACAACAACCTCGGGATCGAGGGAAG GAAAGTGACCAAAGTGGATGGCA | SEQ ID NO: 25 |
| Lwa 3' for pMAL ISO | CAAGCTTGTCGACGGAGCTCGAATTCGGATCCCCTTC CAGTGCTTTGTATTCGAACATCA | SEQ ID NO: 26 |
| pET28 3' Fwd for ISO | GGGGATCCGAATTCGAGCTC | SEQ ID NO: 27 |
| pET28 5' Rev for ISO | GGTATATCTCCTTCTTAAAGTTAAACAAAATTATTTC | SEQ ID NO: 28 |

TABLE 2-continued

Sequences of primers used for isothermal assembly (ISO).

| Primer Name | Sequence (5'→3') | SEQ ID NO |
|---|---|---|
| pMAL 3' Fwd for ISO | GATCCGAATTCGAGCTCCGT | SEQ ID NO: 29 |
| pMAL 5' Rev for ISO | CCTTCCCTCGATCCCGAGG | SEQ ID NO: 30 |
| LwaCas13a G403D Fwd | GTAATATTCTGGAAACCGAAAACGAAAATGATATTACCGGTCGTATGCGTGGT | SEQ ID NO: 31 |
| LwaCas13a G403D Rev | ACCACGCATACGACCGGTAATATCATTTTCGTTTTCGGTTTCCAGAATATTAC | SEQ ID NO: 32 |

After transformation into *E. coli* cells, plasmid DNA was isolated and sequenced to verify the desired sequence. The resulting plasmids were transformed into *E. coli* BL21(DE3) cells for protein expression.

A colony with the appropriate strain was used to inoculate TB media (1 L) with kanamycin (0.05 mg/mL) and grown at 37° C. until an $OD_{600}$ of approximately 0.6 was reached, then the flask was cooled to 18° C. for 30 minutes. The addition of 1 M IPTG (500 μL) was used to induce protein expression, followed by growth at 18° C. for 19 hours. Cells were harvested at 4700×g for 10 minutes at 4° C.

The cell pellet was re-suspended in a lysis buffer containing the following: 20 mM $NaPO_4$ pH 6.8, 0.5 M NaCl, 10 mM imidazole, 5% glycerol, DNase 1, 10 mM $CaCl_2$, lysozyme (1 mg/mL), protease inhibitor and 1% CHAPS. The cells were lysed using an Avestin Emulsiflex C3 homogenizer pre-chilled to 4° C. at 15-20 kpsi with three passes. The lysate was centrifuged at 16,000×g for 20 minutes at 4° C. to remove cell debris.

The cleared lysate for 6× histidine tagged Cas13 proteins was loaded on a HisTrap™ HP column (Cytiva). The procedure consisted of equilibrating the resin with His-Bind® buffer (20 mM $NaPO_4$ pH 6.8, 0.5 M NaCl, 10 mM imidazole, 5% glycerol), followed by sample loading. The column was washed with His·Bind® buffer, followed by a 0.5% Triton-X114 wash, followed by an additional standard wash and a 10% wash consisting of 10% His-Elution buffer (10 mM $NaPO_4$ pH 6.8, 500 mM NaCl, 150 mM imidazole, 5% glycerol). Finally, the sample was eluted using His-Elution buffer.

Alternatively, Cas13a variants from the pET28-MBP-TEV expression plasmid were loaded on MBPTrap™ HP column (Cytiva). The procedure consisted of equilibrating the resin with MBP-Bind buffer (20 mM Tris-HCl pH 7.4, 500 mM NaCl, 1 mM EDTA, 10% glycerol), followed by sample loading. The sample was then washed with MBP-Bind buffer. The sample was eluted using MBP-Elution buffer (20 mM Tris-HCl pH 7.4, 500 mM NaCl, 1 mM EDTA, 10 mM maltose, 10% glycerol).

The partially purified Cas13a variants were then loaded on a HiTrap™ SP strong cation exchange column (Cytiva). The procedure consisted of equilibrating the resin with SP-Bind buffer (20 mM Tris-HCl pH 8.0, 130 mM NaCl, 1 mM DTT, 5% glycerol), followed by sample loading. The sample was then washed with SP-Bind buffer. The sample was eluted using a linear gradient to 50% SP-Elution buffer (20 mM Tris-HCl pH 8.0, 2 M NaCl, 1 mM DTT, 5% glycerol). The Cas13a variants eluted from the column at a NaCl concentration between 0.4-0.5 M.

The purified Cas13a variants were concentrated to approximately 10 mg/mL using an Amicon® Ultra-15 (Sigma Aldrich) with a 10 K MWCO filter by centrifuging at 4000×g. The concentrated protein was placed in a hydrated Slide-A-Lyzer™ dialysis cassette (Thermo Fisher) with a 10K MWCO and dialyzed against three rounds of dialysis buffer (50 mM Tris-HCl pH 7.5, 0.6 M NaCl, 2 mM DTT, 50% glycerol). The final concentration was determined by a Nano Drop 8000 (Thermo Scientific) and stored at −20° C. (see FIG. 1 for SDS-PAGE).

Example 2

The activity of Cas13a proteins were assayed by observing the non-specific RNase activity in the degradation of fluorescent-labeled RNA. The nucleic acid target (FIG. 2A) was first ordered as two Ultramer® DNA Oligos (Integrated DNA Technologies) and annealed together by heating at 95° C. for 5 min in duplex buffer with a slow cool to room temperature. The dsDNA target was transcribed to RNA by the HiScribe™ T7 High Yield RNA Synthesis Kit (New England Biolabs), followed by a clean-up with the MEGA-clear™ Purification Kit (Applied Biosystems). The RNP complex (FIG. 2B) was formed by combining purified Cas13a protein and the corresponding crRNA (Table 3) and incubating at room temperature for 10 minutes.

TABLE 3

Sequences of crRNA for each Cas13a protein variant

| Cas13a variant | Ribonucleotide Sequences (5'→3') | SEQ ID NO |
|---|---|---|
| LwaCas13a | GGGGAUUUAGACUACCCCAAAAACGAAGGGGACUAAAACUAGAUUGCUGUUCUACCAAGUAAUCCAU | 33 |
| LbuCas13a | GACCACCCCAAAAAUGAAGGGGACUAAAACAUAGAUUGCUGUUCUACCAAGUAAUCCAU | 34 |
| LshCas13a | CCACCCCAAUAUCGAAGGGGACUAAAACUAGAUUGCUGUUCUACCAAGUAAUCCAU | 35 |

All nucleotides are ribonucleotides; spacer sequences are underlined.

The Cas13a RNP complex (1 µM) was titrated down with nuclease reaction buffer (40 mM Tris-HCl pH 7.4, 60 mM NaCl, 6 mM MgCl$_2$) in two-fold dilutions to 1 nM RNP to afford a wide range of Cas13a nuclease reactions. The activity of the Cas13a RNP complex was measured by the addition of RNA reporter (degradation reporter probe) (200 nM, RNaseAlert™ Substrate), RNase inhibitor (1 µL, SUPERase-In™), total human RNA (25 ng, purified from HEK-293 cells), RNA target (20 ng) in nuclease reaction buffer (total volume of 100 µL). Reactions were allowed to proceed for 10 min at 37° C., followed by detection on a fluorescent plate reader (TECAN) using the fluorescein channel (490 nm excitation, 520 nm emission).

These results show a rapid visualization of nucleic acid degradation with LbuCas13a using only 4 nM RNP (Table 4). These proteins were purified using a C-terminal 6× histidine tag.

TABLE 4

Cas13a RNP activity assay data after 10 min at 37° C.

| Lbu | | Lsh | | Lwa | | Lwa G403D | |
|---|---|---|---|---|---|---|---|
| RNP (nM) | Emission | RNP (nM) | Emission | RNP (nM) | Emission | RNP (nM) | Emission |
| 1000 | 17182 | 1000 | 1165 | 1000 | 2948 | 1000 | 8989 |
| 500 | 31575 | 500 | 880 | 500 | 2387 | 500 | 12706 |
| 250 | 41002 | 250 | 739 | 250 | 2113 | 250 | 19003 |
| 125 | 39324 | 125 | 629 | 125 | 1740 | 125 | 22328 |
| 63 | 38526 | 63 | 581 | 63 | 1418 | 63 | 18684 |
| 31 | 50516 | 31 | 568 | 31 | 1158 | 31 | 6429 |
| 16 | 51035 | 16 | 560 | 16 | 1081 | 16 | 1058 |
| 8 | 49605 | 8 | 535 | 8 | 872 | 8 | 738 |
| 4 | 50376 | 4 | 550 | 4 | 752 | 4 | 693 |
| 2 | 25572 | 2 | 552 | 2 | 612 | 2 | 678 |
| 1 | 22674 | 1 | 528 | 1 | 581 | 1 | 676 |
| 0 | 1371 | 0 | 901 | 0 | 1886 | 0 | 5039 |

Figure 3A:
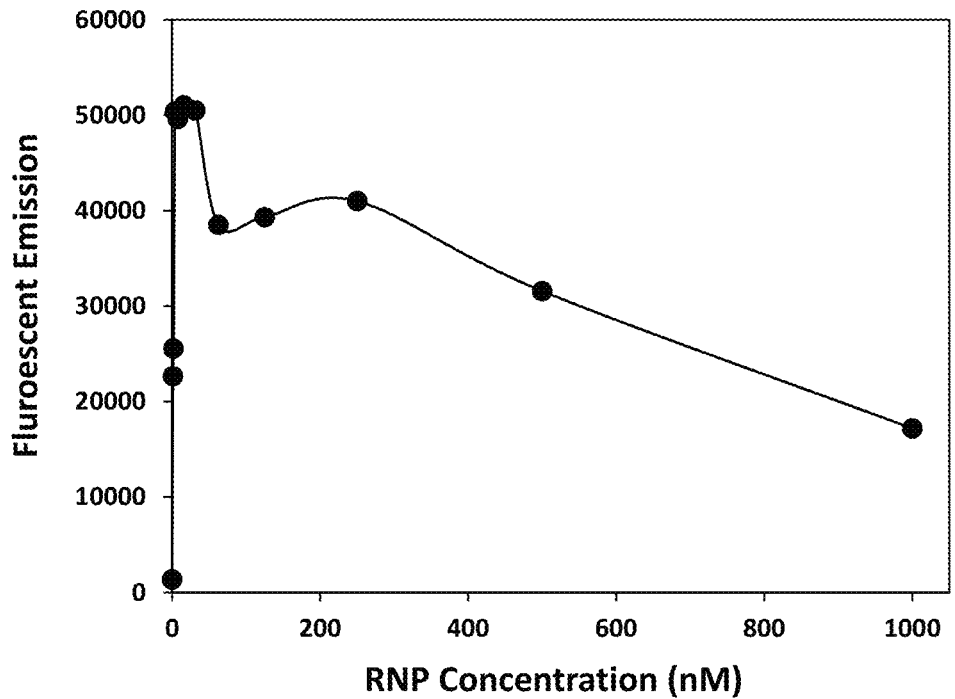
FIG. 3A shows a fluorescent emission of titrated LbuCas13a ribonucleoprotein complex (RNP).
Figure 3B:
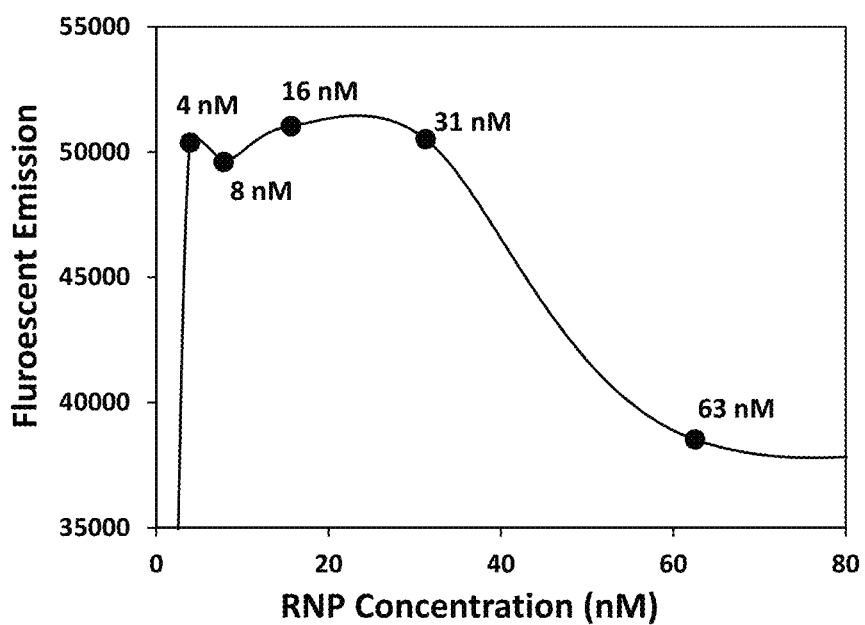
FIG. 3B shows a closeup of the same data in FIG. 3A illustrating a bell-like curve with an optimum RNP concentration range between 4 and 31 nM.

While Lwa and Lsh Cas13a were described in the literature as potentially useful Cas13 variants, RNase activity of these variants was not observed at the concentration ranges for RNP complex used in this study (Table 4). For LbuCas13a, there was a clear bell-like curve representation of the data (FIG. 3A-B). As the concentration of RNP soared from 31 nM to 1 µM, the RNase activity decreased and as the concentration of RNP was reduced from 4 nm, RNase activity also declined.

The N-terminal maltose binding protein (MBP) fusions of each of these variants were also prepared and tested for their non-specific RNase activity; however, activity substantially decreased and required more than 3 hours and a 15-fold increase in LbuCas13a RNP concentration to detect nucleic acid degradation by this assay (Table 5). These proteins were purified with a CTD-6× histidine tag or NTD-MBP.

TABLE 5

MBP-Cas13a RNP activity assay data after 3 hr at 37° C.

| Lbu | | Lsh | | Lwa | |
|---|---|---|---|---|---|
| RNP (nM) | Emission | RNP (nM) | Emission | RNP (nM) | Emission |
| 1000 | 550 | 1000 | 415 | 1000 | 362 |
| 500 | 135 | 500 | 319 | 500 | 2589 |
| 250 | 446 | 250 | 239 | 250 | 2173 |
| 125 | 777 | 125 | 196 | 125 | 2058 |
| 63 | 841 | 63 | 174 | 63 | 1874 |
| 31 | 179 | 31 | 168 | 31 | 1747 |
| 16 | 681 | 16 | 166 | 16 | 163 |
| 8 | 354 | 8 | 160 | 8 | 164 |
| 4 | 254 | 4 | 160 | 4 | 166 |
| 2 | 203 | 2 | 161 | 2 | 166 |
| 1 | 177 | 1 | 160 | 1 | 159 |
| 0 | 541 | 0 | 400 | 0 | 368 |

Using the Basic Local Alignment Search Tool (BLAST) on NCBI, the LwaCas13a protein sequence found in the literature [2] had a mutation at position 403; therefore, LwaCas13a G403D was cloned, overexpressed and purified (SEQ ID NO: 13-14). These results (Table 3) reveal RNase activity for this variant using an RNP concentration range between 62.5-500 nM. Although this single mutation uncovered the non-specific RNase activity of this enzyme, LbuCas13a is still the better alternative in terms of the desired activity per molecule of protein.

Example 3

The ribonucleoprotein (RNP) complex was formed by combining purified Cas13a protein and the corresponding crRNA and incubating at room temperature for 10 minutes.

The Cas13a RNP complex (1 µM) was added to 25 ng of total human RNA (purified from HEK 293), 1 µL RNase Inhibitor, 20 ng of nucleic acid target, 0.2 µM of RNA degradation reporter probe (FAM-IBFQ labeled) in a final volume of 100 µL in nuclease assay buffer (40 mM Tris-HCl, 60 mM NaCl, 6 mM MgCl$_2$, ph 7.4). The mixture was incubated at 37° C. for 10 min. Following incubation, the reaction mixture was visualized by a fluorescent plate reader (490 nm excitation, 520 nm emission).

Figure 4:
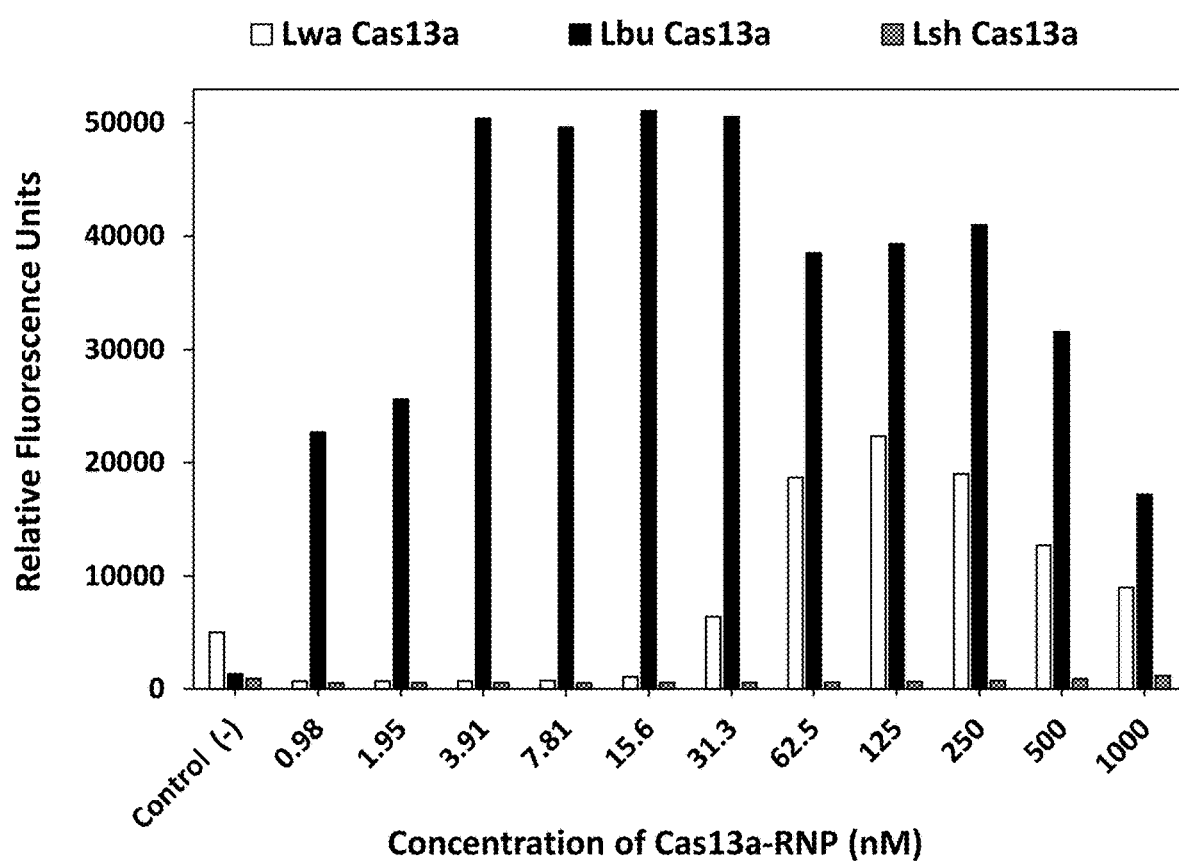
FIG. 4 shows the fluorescent emission of a cleaved RNA reporter by Cas13a variants at different enzyme concentrations.

FIG. 4 shows the activity of Lwa Cas13a, Lbu Cas13a, and Lsh Cas13a variants. Lbu Cas13a is active across a broad range of concentrations with peak activity from about 3.91 nM to 31.3 nM. Lwa Cas13a shows activity across a range of concentrations with peak activity from about 62.5 nM to 250 nM.

SEQUENCE LISTING

<160> NUMBER OF SEQ ID NOS: 44

<210> SEQ ID NO 1
<211> LENGTH: 3546
<212> TYPE: DNA
<213> ORGANISM: Artificial Sequence
<220> FEATURE:
<223> OTHER INFORMATION: Synthetic

<400> SEQUENCE: 1
atgaaggtga ccaaagttgg tggtatcagc cataaaaagt ataccagcga aggtcgtctg      60

```
gttaaaagcg aaagcgaaga aaatcgtacc gatgaacgtc tgagcgcact gctgaatatg    120
cgtctggata tgtatatcaa aaatccgagc agcaccgaaa ccaaagaaaa tcagaaacgt    180
atcggcaagc tgaaaaagtt cttcagcaac aaaatggtgt acctgaaaga taacaccctg    240
agcctgaaaa acggcaagaa agaaaatatc gatcgcgagt atagcgaaac cgatattctg    300
gaaagtgatg tgcgtgacaa aaaaaacttt gccgtcctga aaagatcta tctgaacgaa    360 aatgtgaaca gcgaagaact ggaagtgttt cgcaacgaca ttaaaaagaa gctgaacaag    420
atcaacagcc tgaaatatag cttcgagaaa acaaagcca actatcagaa gatcaacgag    480
aacaacatcg aaaagtggaa aggtaaaagc aagcgcaaca tcatctatga ttattatcgt    540
gaaagcgcca acgtgatgc ctatgttagc aatgttaaag aggccttcga caagctgtat    600
aaagaagaag atattgccaa actggtgctg gaaattgaaa atctgaccaa gctggaaaaa    660
tacaagatcc gcgaattcta tcacgaaatc attggtcgca aaaacgataa agagaacttc    720
gccaaaatca tctacgaaga aattcagaac gtgaataaca tgaaagaact gatcgagaaa    780
gttccggata tgagcgaact gaaaaaaagc caggtgttct acaaatatta cctggacaaa    840
gaggaactga cgataaaaa catcaaatac gccttttgcc acttcgtgga aatcgaaatg    900
agccagctgc tgaaaaacta tgtgtataaa cgcctgagca catcagcaa cgataagatt    960 aaacgcatct tcgagtacca gaacctgaag aaactgattg aaaacaaact gcttaacaaa    1020
ctggatacct atgtgcgtaa ttgcggcaaa tacaactatt atctgcagga tggtgaaatt    1080
gcgaccagcg atttattgc acgtaatcgt cagaatgaag cctttctgcg taacattatt    1140
ggtgttagca gcgttgcata ttttagcctg cgtaatatcc tggaaaccga aacgagaat    1200 gatatcaccg gtcgtatgcg tggtaaaacc gtgaaaaaca ataaaggcga agagaaatat    1260
gtgagcggtg aggtggataa aatctacaac gaaaacaaaa agaacgaagt gaaagaaaac    1320
ctgaaaatgt tttacagcta cgactttaac atggacaaca agaacgagat cgaagatttt    1380
ttcgccaaca ttgatgaagc cattagcagc attcgtcatg gcattgttca ctttaatctg    1440
gaacttgagg gcaaagacat cttcgcgttt aaaaacattg caccgagcga gattagcaaa    1500
aagatgttcc agaacgaaat taacgagaaa aaactgaaac tgaagatctt cgccagctg    1560 aatagcgcaa atgttttcg ctatcttgag aaatacaaaa tcctgaacta tctgaaacgc    1620
acccgctttg aatttgtgaa caaaaacatt ccgtttgtgc cgagctttac caaactgtat    1680
agccgtattg atgatctgaa aaacagcctg ggcatttatt ggaaaacccc gaaaccaac    1740 gatgataaca gacgaaaga aatcatcgat gcccagattt atctgcttaa gaacatctac    1800
tatggcgaat tctgaacta ttttatgagc aacaacggca acttctttga aatcagcaaa    1860
gagattatcg agctgaataa aaacgacaaa cgcaatctga aaaccggctt ctataaactg    1920
cagaagtttg aggatatcca agaaaagatc ccgaaagaat atctggcgaa tattcagagc    1980
ctgtacatga ttaatgcagg caatcaggat gaggaagaga agataccta tatcgatttc    2040 atccagaaaa tctttctgaa aggctttatg acctatctgg ccaataatgg tcgtctgagt    2100
ctgatttata tcggtagtga tgaagaaacc aataccagcc tggcagaaaa aaaacaagag    2160
ttcgataagt tcctgaagaa gtacgaacag aacaacaaca tcaagatccc gtatgaaatc    2220
aatgaatttc tgcgcgaaat caagctgggc aacattctga aatacaccga acgcctgaat    2280
atgttctatc tgattctgaa actgctgaac cataaagagc tgacgaatct gaaaggtagc    2340
ctggaaaagt atcagagcgc aaataaagag gaagcattta gcgatcagct ggaactgatt    2400
```

```
aatctgctga atctggataa taaccgtgtg accgaagatt tcgaattaga agcagatgag   2460
atcggcaaat tcctggattt taatggcaac aaagtgaagg acaacaaaga gcttaagaag   2520
ttcgacacca acaagatcta ttttgatggc gagaacatca tcaaacaccg tgcctttat    2580 aacatcaaaa aatacggtat gctgaacctg ctggaaaaga ttgcagataa agcaggctat   2640
aaaatcagca ttgaagagtt gaaaaaatac agcaacaaga aaacgagat tgagaaaaac    2700 cacaaaatgc aagaaaatct gcaccgcaaa tatgcacgtc cgcgtaaaga tgaaaaattc   2760
accgatgaag attatgaaag ctacaaacag gccatcgaaa acatcgaaga atatacccat   2820
ctgaagaaca aagtcgaatt caacgaactg aatctgctgc agggtctgct gctgcgtatt   2880
ctgcatcgtc tggtgggtta taccagcatt tgggaacgtg atctgcgttt tcgcctgaaa   2940
ggtgaatttc ctgaaaacca gtatatcgag gaaatcttca acttcgagaa taaaaagaat   3000
gtgaagtata aggtggcca gatcgtcgag aaatatatca aattctacaa agaactgcac    3060
cagaacgacg aggtgaaaat caacaaatat agcagcgcga acatcaaagt gctgaaacaa   3120
gagaaaaaag acctgtacat ccgcaactat atcgcccact ttaactatat tccgcatgca   3180
gaaattagtc tgctggaagt tctgaaaaac ctgcgtaaac tgctgtcata tgatcgtaaa   3240
cttaaaaacg ccgtgatgaa aagcgttgtg acatcctga aagagtatgg ttttgttgcg    3300
acctttaaaa tcggtgccga taaaaagatt ggtattcaga ccctggaaag cgagaagatt   3360
gttcacctga aaatcttaa gaaaagaaa cttatgaccg atcgcaatag cgaggaactg     3420
tgtaaactgg tgaaaattat gtttgagtat aaaatggaag agaagaaatc gaaaatggg    3480 gatccgaatt cgagctccgt cgacaagctt gcggccgcac tcgagcacca ccaccaccac   3540
cactga                                                              3546
```

<210> SEQ ID NO 2
<211> LENGTH: 1181
<212> TYPE: PRT
<213> ORGANISM: Artificial Sequence
<220> FEATURE:
<223> OTHER INFORMATION: Synthetic

<400> SEQUENCE: 2

```
Met Lys Val Thr Lys Val Gly Gly Ile Ser His Lys Lys Tyr Thr Ser
1               5                   10                  15

Glu Gly Arg Leu Val Lys Ser Glu Ser Glu Glu Asn Arg Thr Asp Glu
            20                  25                  30

Arg Leu Ser Ala Leu Leu Asn Met Arg Leu Asp Met Tyr Ile Lys Asn
        35                  40                  45

Pro Ser Ser Thr Glu Thr Lys Glu Asn Gln Lys Arg Ile Gly Lys Leu
    50                  55                  60

Lys Lys Phe Phe Ser Asn Lys Met Val Tyr Leu Lys Asp Asn Thr Leu
65                  70                  75                  80

Ser Leu Lys Asn Gly Lys Lys Glu Asn Ile Asp Arg Glu Tyr Ser Glu
                85                  90                  95

Thr Asp Ile Leu Glu Ser Asp Val Arg Asp Lys Lys Asn Phe Ala Val
            100                 105                 110

Leu Lys Lys Ile Tyr Leu Asn Glu Asn Val Asn Ser Glu Glu Leu Glu
        115                 120                 125

Val Phe Arg Asn Asp Ile Lys Lys Lys Leu Asn Lys Ile Asn Ser Leu
    130                 135                 140

Lys Tyr Ser Phe Glu Lys Asn Lys Ala Asn Tyr Gln Lys Ile Asn Glu
145                 150                 155                 160
```

```
Asn Asn Ile Glu Lys Val Gly Lys Ser Lys Arg Asn Ile Ile Tyr
                165                 170                 175

Asp Tyr Tyr Arg Glu Ser Ala Lys Arg Asp Ala Tyr Val Ser Asn Val
            180                 185                 190

Lys Glu Ala Phe Asp Lys Leu Tyr Lys Glu Asp Ile Ala Lys Leu
        195                 200                 205

Val Leu Glu Ile Glu Asn Leu Thr Lys Leu Lys Tyr Lys Ile Arg
    210                 215                 220

Glu Phe Tyr His Glu Ile Ile Gly Arg Lys Asn Asp Lys Glu Asn Phe
225                 230                 235                 240

Ala Lys Ile Ile Tyr Glu Glu Ile Gln Asn Val Asn Asn Met Lys Glu
                245                 250                 255

Leu Ile Glu Lys Val Pro Asp Met Ser Glu Leu Lys Lys Ser Gln Val
            260                 265                 270

Phe Tyr Lys Tyr Tyr Leu Asp Lys Glu Glu Leu Asn Asp Lys Asn Ile
        275                 280                 285

Lys Tyr Ala Phe Cys His Phe Val Glu Ile Glu Met Ser Gln Leu Leu
    290                 295                 300

Lys Asn Tyr Val Tyr Lys Arg Leu Ser Asn Ile Ser Asn Asp Lys Ile
305                 310                 315                 320

Lys Arg Ile Phe Glu Tyr Gln Asn Leu Lys Lys Leu Ile Glu Asn Lys
                325                 330                 335

Leu Leu Asn Lys Leu Asp Thr Tyr Val Arg Asn Cys Gly Lys Tyr Asn
            340                 345                 350

Tyr Tyr Leu Gln Asp Gly Glu Ile Ala Thr Ser Asp Phe Ile Ala Arg
        355                 360                 365

Asn Arg Gln Asn Glu Ala Phe Leu Arg Asn Ile Ile Gly Val Ser Ser
    370                 375                 380

Val Ala Tyr Phe Ser Leu Arg Asn Ile Leu Glu Thr Glu Asn Glu Asn
385                 390                 395                 400

Asp Ile Thr Gly Arg Met Arg Gly Lys Thr Val Lys Asn Asn Lys Gly
                405                 410                 415

Glu Glu Lys Tyr Val Ser Gly Glu Val Asp Lys Ile Tyr Asn Glu Asn
            420                 425                 430

Lys Lys Asn Glu Val Lys Glu Asn Leu Lys Met Phe Tyr Ser Tyr Asp
        435                 440                 445

Phe Asn Met Asp Asn Lys Asn Glu Ile Glu Asp Phe Phe Ala Asn Ile
    450                 455                 460

Asp Glu Ala Ile Ser Ser Ile Arg His Gly Ile Val His Phe Asn Leu
465                 470                 475                 480

Glu Leu Glu Gly Lys Asp Ile Phe Ala Phe Lys Asn Ile Ala Pro Ser
                485                 490                 495

Glu Ile Ser Lys Lys Met Phe Gln Asn Glu Ile Asn Glu Lys Lys Leu
            500                 505                 510

Lys Leu Lys Ile Phe Arg Gln Leu Asn Ser Ala Asn Val Phe Arg Tyr
        515                 520                 525

Leu Glu Lys Tyr Lys Ile Leu Asn Tyr Leu Lys Arg Thr Arg Phe Glu
    530                 535                 540

Phe Val Asn Lys Asn Ile Pro Phe Val Pro Ser Phe Thr Lys Leu Tyr
545                 550                 555                 560

Ser Arg Ile Asp Asp Leu Lys Asn Ser Leu Gly Ile Tyr Trp Lys Thr
                565                 570                 575
```

```
Pro Lys Thr Asn Asp Asp Asn Lys Thr Lys Glu Ile Ile Asp Ala Gln
            580                 585                 590
Ile Tyr Leu Leu Lys Asn Ile Tyr Tyr Gly Glu Phe Leu Asn Tyr Phe
        595                 600                 605
Met Ser Asn Asn Gly Asn Phe Phe Glu Ile Ser Lys Glu Ile Ile Glu
    610                 615                 620
Leu Asn Lys Asn Asp Lys Arg Asn Leu Lys Thr Gly Phe Tyr Lys Leu
625                 630                 635                 640
Gln Lys Phe Glu Asp Ile Gln Glu Lys Ile Pro Lys Glu Tyr Leu Ala
                645                 650                 655
Asn Ile Gln Ser Leu Tyr Met Ile Asn Ala Gly Asn Gln Asp Glu Glu
            660                 665                 670
Glu Lys Asp Thr Tyr Ile Asp Phe Ile Gln Lys Ile Phe Leu Lys Gly
        675                 680                 685
Phe Met Thr Tyr Leu Ala Asn Asn Gly Arg Leu Ser Leu Ile Tyr Ile
    690                 695                 700
Gly Ser Asp Glu Glu Thr Asn Thr Ser Leu Ala Glu Lys Lys Gln Glu
705                 710                 715                 720
Phe Asp Lys Phe Leu Lys Lys Tyr Glu Gln Asn Asn Asn Ile Lys Ile
                725                 730                 735
Pro Tyr Glu Ile Asn Glu Phe Leu Arg Glu Ile Lys Leu Gly Asn Ile
            740                 745                 750
Leu Lys Tyr Thr Glu Arg Leu Asn Met Phe Tyr Leu Ile Leu Lys Leu
        755                 760                 765
Leu Asn His Lys Glu Leu Thr Asn Leu Lys Gly Ser Leu Glu Lys Tyr
    770                 775                 780
Gln Ser Ala Asn Lys Glu Glu Ala Phe Ser Asp Gln Leu Glu Leu Ile
785                 790                 795                 800
Asn Leu Leu Asn Leu Asp Asn Asn Arg Val Thr Glu Asp Phe Glu Leu
                805                 810                 815
Glu Ala Asp Glu Ile Gly Lys Phe Leu Asp Phe Asn Gly Asn Lys Val
            820                 825                 830
Lys Asp Asn Lys Glu Leu Lys Lys Phe Asp Thr Asn Lys Ile Tyr Phe
        835                 840                 845
Asp Gly Glu Asn Ile Ile Lys His Arg Ala Phe Tyr Asn Ile Lys Lys
    850                 855                 860
Tyr Gly Met Leu Asn Leu Leu Glu Lys Ile Ala Asp Lys Ala Gly Tyr
865                 870                 875                 880
Lys Ile Ser Ile Glu Glu Leu Lys Lys Tyr Ser Asn Lys Lys Asn Glu
                885                 890                 895
Ile Glu Lys Asn His Lys Met Gln Glu Asn Leu His Arg Lys Tyr Ala
            900                 905                 910
Arg Pro Arg Lys Asp Glu Lys Phe Thr Asp Glu Asp Tyr Glu Ser Tyr
        915                 920                 925
Lys Gln Ala Ile Glu Asn Ile Glu Glu Tyr Thr His Leu Lys Asn Lys
    930                 935                 940
Val Glu Phe Asn Glu Leu Asn Leu Leu Gln Gly Leu Leu Leu Arg Ile
945                 950                 955                 960
Leu His Arg Leu Val Gly Tyr Thr Ser Ile Trp Glu Arg Asp Leu Arg
                965                 970                 975
Phe Arg Leu Lys Gly Glu Phe Pro Glu Asn Gln Tyr Ile Glu Glu Ile
            980                 985                 990
Phe Asn Phe Glu Asn Lys Lys Asn  Val Lys Tyr Lys Gly  Gly Gln Ile
```

| | | | | | | | | | | |
|---|---|---|---|---|---|---|---|---|---|---|
| | | 995 | | | 1000 | | | 1005 | | |
| Val | Glu | Lys | Tyr | Ile | Lys | Phe | Tyr | Lys | Glu | Leu | His | Gln | Asn | Asp |
| 1010 | | | | 1015 | | | | | 1020 | | |

Val Glu Lys Tyr Ile Lys Phe Tyr Lys Glu Leu His Gln Asn Asp
    1010                1015                    1020

Glu Val Lys Ile Asn Lys Tyr Ser Ser Ala Asn Ile Lys Val Leu
    1025                1030                    1035

Lys Gln Glu Lys Lys Asp Leu Tyr Ile Arg Asn Tyr Ile Ala His
    1040                1045                    1050

Phe Asn Tyr Ile Pro His Ala Glu Ile Ser Leu Leu Glu Val Leu
    1055                1060                    1065

Glu Asn Leu Arg Lys Leu Leu Ser Tyr Asp Arg Lys Leu Lys Asn
    1070                1075                    1080

Ala Val Met Lys Ser Val Val Asp Ile Leu Lys Glu Tyr Gly Phe
    1085                1090                    1095

Val Ala Thr Phe Lys Ile Gly Ala Asp Lys Lys Ile Gly Ile Gln
    1100                1105                    1110

Thr Leu Glu Ser Glu Lys Ile Val His Leu Lys Asn Leu Lys Lys
    1115                1120                    1125

Lys Lys Leu Met Thr Asp Arg Asn Ser Glu Glu Leu Cys Lys Leu
    1130                1135                    1140

Val Lys Ile Met Phe Glu Tyr Lys Met Glu Lys Lys Ser Glu
    1145                1150                    1155

Asn Gly Asp Pro Asn Ser Ser Val Asp Lys Leu Ala Ala Ala
    1160                1165                    1170

Leu Glu His His His His His His
    1175                1180

<210> SEQ ID NO 3
<211> LENGTH: 4701
<212> TYPE: DNA
<213> ORGANISM: Artificial Sequence
<220> FEATURE:
<223> OTHER INFORMATION: Synthetic

<400> SEQUENCE: 3

```
atgaaaatcg aagaaggtaa actggtaatc tggattaacg cgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca agcgttcca ggacaagctg tatccgttta ctgggatgc cgtacgttac      300
aacggcaagc tgattgctta cccgatcgct gttgaagcgt atcgctgat ttataacaaa      360
gatctgctgc cgaaccccgcc aaaaacctgg gaagagatcc cggcgctgga taagaactg     420
aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc aaaagagttc     840
ctcgaaaact atctgctgac tgatgaaggt ctggaagcgg ttaataaaga caaaccgctg     900
ggtgccgtag cgctgaagtc ttacgaggaa gagttggtga agatccgcg tattgccgcc     960
```

```
actatggaaa acgcccagaa aggtgaaatc atgccgaaca tcccgcagat gtccgctttc   1020
tggtatgccg tgcgtactgc ggtgatcaac gccgccagcg tcgtcagac tgtcgatgaa    1080 gccctgaaag acgcgcagac taattcgagc tcgaacaaca acaacaataa caataacaac   1140
aacctcggga tcgagggaag gaaggtgacc aaagttggtg gtatcagcca taaaaagtat   1200
accagcgaag gtcgtctggt taaaagcgaa agcgaagaaa atcgtaccga tgaacgtctg   1260
agcgcactgc tgaatatgcg tctggatatg tatatcaaaa atccgagcag caccgaaacc   1320
aaagaaaatc agaaacgtat cggcaagctg aaaaagttct tcagcaacaa aatggtgtac   1380
ctgaaagata cacccctgag cctgaaaaac ggcaagaaag aaaatatcga tcgcgagtat   1440
agcgaaaccg atattctgga aagtgatgtg cgtgacaaaa aaaactttgc cgtcctgaaa   1500
aagatctatc tgaacgaaaa tgtgaacagc gaagaactgg aagtgtttcg caacgacatt   1560
aaaaagaagc tgaacaagat caacagcctg aaatatagct tcgagaaaaa caaagccaac   1620
tatcagaaga tcaacgagaa caacatcgaa aaagtggaag gtaaaagcaa gcgcaacatc   1680
atctatgatt attatcgtga aagcgccaaa cgtgatgcct atgttagcaa tgttaaagag   1740
gccttcgaca gctgtataaa agaagaagat attgccaaac tggtgctgga aattgaaaat   1800
ctgaccaagc tggaaaaata caagatccgc gaattctatc acgaaatcat tggtcgcaaa   1860
aacgataaag agaacttcgc caaaatcatc tacgaagaaa ttcagaacgt gaataacatg   1920
aaagaactga tcgagaaagt tccggatatg agcgaactga aaaaagcca ggtgttctac    1980 aaatattacc tggacaaaga ggaactgaac gataaaaaca tcaaatacgc cttttgccac   2040
ttcgtggaaa tcgaaatgag ccagctgctg aaaaactatg tgtataaacg cctgagcaac   2100
atcagcaacg ataagattaa acgcatcttc gagtaccaga acctgaagaa actgattgaa   2160
aacaaactgc ttaacaaact ggatacctat gtgcgtaatt gcggcaaata caactattat   2220
ctgcaggatg gtgaaattgc gaccagcgat tttattgcac gtaatcgtca gaatgaagcc   2280
tttctgcgta acattattgg tgttagcagc gttgcatatt ttagcctgcg taatatcctg   2340
gaaaccgaaa acgagaatga tatcaccggt cgtatgcgtg gtaaaaccgt gaaaaacaat   2400
aaaggcgaag agaaatatgt gagcggtgag gtggataaaa tctacaacga aaacaaaaag   2460
aacgaagtga agaaaaacct gaaaatgttt tacagctacg actttaacat ggacaacaag   2520
aacgagatcg aagattttttt cgccaacatt gatgaagcca ttagcagcat tcgtcatggc   2580
attgttcact ttaatctgga acttgagggc aaagacatct tcgcgtttaa aacattgca    2640 ccgagcgaga ttagcaaaaa gatgttccag aacgaaatta cgagaaaaa actgaaactg   2700 aagatctttc gccagctgaa tagcgcaaat gttttttcgct atcttgagaa atacaaaatc   2760
ctgaactatc tgaaacgcac ccgctttgaa tttgtgaaca aaaacattcc gtttgtgccg   2820
agctttacca aactgtatag ccgtattgat gatctgaaaa acagcctggg catttattgg   2880
aaaaccccga aaaccaacga tgataacaag acgaaagaaa tcatcgatgc ccagatttat   2940
ctgcttaaga acatctacta tggcgaattt ctgaactatt ttatgagcaa caacggcaac   3000
ttctttgaaa tcagcaaaga gattatcgag ctgaataaaa acgacaaacg caatctgaaa   3060
accggcttct ataaactgca gaagtttgag gatatccaag aaaagatccc gaaagaatat   3120
ctggcgaata ttcagagcct gtacatgatt aatgcaggca atcaggatga ggaagagaaa   3180
gatacccata tcgatttcat ccagaaaatc tttctgaaag ctttatgac ctatctggcc    3240 aataatggtc gtctgagtct gatttatatc ggtagtgatg aagaaccaa taccagcctg   3300
```

```
gcagaaaaaa aacaagagtt cgataagttc ctgaagaagt acgaacagaa caacaacatc    3360
aagatcccgt atgaaatcaa tgaatttctg cgcgaaatca agctgggcaa cattctgaaa    3420
tacaccgaac gcctgaatat gttctatctg attctgaaac tgctgaacca taaagagctg    3480
acgaatctga aggtagcct  ggaaaagtat cagagcgcaa ataaagagga agcatttagc    3540
gatcagctgg aactgattaa tctgctgaat ctggataata ccgtgtgac  cgaagatttc    3600 gaattagaag cagatgagat cggcaaattc ctggatttta atggcaacaa agtgaaggac    3660
aacaaagagc ttaagaagtt cgacaccaac aagatctatt ttgatggcga acatcatc     3720 aaacaccgtg cctttt ataa catcaaaaaa tacggtatgc tgaacctgct ggaaaagatt    3780
gcagataaag caggctataa aatcagcatt gaagagttga aaaatacag  caacaagaaa    3840 aacgagattg agaaaaacca caaaatgcaa gaaaatctgc accgcaaata tgcacgtccg    3900
cgtaaagatg aaaaattcac cgatgaagat tatgaaagct acaaacaggc catcgaaaac    3960
atcgaagaat atacccatct gaagaacaaa gtcgaattca cgaactgaa  tctgctgcag    4020 ggtctgctgc tgcgtattct gcatcgtctg gtgggttata ccagcatttg gaacgtgat     4080 ctgcgttttc gcctgaaagg tgaatttcct gaaaaccagt atatcgagga aatcttcaac    4140
ttcgagaata aaagaatgt  gaagtataaa ggtggccaga tcgtcgagaa atatatcaaa    4200
ttctacaaag aactgcacca gaacgacgag gtgaaaatca acaaatatag cagcgcgaac    4260
atcaaagtgc tgaaacaaga gaaaaaagac ctgtacatcc gcaactatat cgcccacttt    4320
aactatattc gcatgcaga  aattagtctg ctggaagttc tggaaaacct gcgtaaactg    4380
ctgtcatatg atcgtaaact taaaaacgcc gtgatgaaaa gcgttgtgga catcctgaaa    4440
gagtatggtt ttgttgcgac ctttaaaatc ggtgccgata aaagattgg  tattcagacc    4500 ctggaaagcg agaagattgt tcacctgaaa aatcttaaga aaaagaaact tatgaccgat    4560
cgcaatagcg aggaactgtg taaactggtg aaaattatgt ttgagtataa aatggaagag    4620
aagaaatccg aaaatgatcc gaattcgagc tccgtcgaca gcttgcggc  cgcactcgag    4680 caccaccacc accaccactg a                                              4701
```

<210> SEQ ID NO 4
<211> LENGTH: 1566
<212> TYPE: PRT
<213> ORGANISM: Artificial Sequence
<220> FEATURE:
<223> OTHER INFORMATION: Synthetic

<400> SEQUENCE: 4

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110
```

```
Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Lys Val Thr Lys Val Gly Gly Ile Ser His Lys Lys Tyr
385                 390                 395                 400

Thr Ser Glu Gly Arg Leu Val Lys Ser Glu Ser Glu Asn Arg Thr
                405                 410                 415

Asp Glu Arg Leu Ser Ala Leu Leu Asn Met Arg Leu Asp Met Tyr Ile
            420                 425                 430

Lys Asn Pro Ser Ser Thr Glu Thr Lys Glu Asn Gln Lys Arg Ile Gly
        435                 440                 445

Lys Leu Lys Lys Phe Phe Ser Asn Lys Met Val Tyr Leu Lys Asp Asn
    450                 455                 460

Thr Leu Ser Leu Lys Asn Gly Lys Lys Glu Asn Ile Asp Arg Glu Tyr
465                 470                 475                 480

Ser Glu Thr Asp Ile Leu Glu Ser Asp Val Arg Asp Lys Lys Asn Phe
                485                 490                 495

Ala Val Leu Lys Lys Ile Tyr Leu Glu Asn Val Asn Ser Glu Glu
            500                 505                 510

Leu Glu Val Phe Arg Asn Asp Ile Lys Lys Lys Leu Asn Lys Ile Asn
        515                 520                 525

Ser Leu Lys Tyr Ser Phe Glu Lys Asn Lys Ala Asn Tyr Gln Lys Ile
```

```
                530             535             540
Asn Glu Asn Asn Ile Glu Lys Val Glu Gly Lys Ser Lys Arg Asn Ile
545                 550                 555                 560

Ile Tyr Asp Tyr Tyr Arg Glu Ser Ala Lys Arg Asp Ala Tyr Val Ser
                565                 570                 575

Asn Val Lys Glu Ala Phe Asp Lys Leu Tyr Lys Glu Glu Asp Ile Ala
                580                 585                 590

Lys Leu Val Leu Glu Ile Glu Asn Leu Thr Lys Leu Glu Lys Tyr Lys
                595                 600                 605

Ile Arg Glu Phe Tyr His Glu Ile Ile Gly Arg Lys Asn Asp Lys Glu
610                 615                 620

Asn Phe Ala Lys Ile Ile Tyr Glu Glu Ile Gln Asn Val Asn Asn Met
625                 630                 635                 640

Lys Glu Leu Ile Glu Lys Val Pro Asp Met Ser Glu Leu Lys Lys Ser
                645                 650                 655

Gln Val Phe Tyr Lys Tyr Tyr Leu Asp Lys Glu Glu Leu Asn Asp Lys
                660                 665                 670

Asn Ile Lys Tyr Ala Phe Cys His Phe Val Glu Ile Glu Met Ser Gln
                675                 680                 685

Leu Leu Lys Asn Tyr Val Tyr Lys Arg Leu Ser Asn Ile Ser Asn Asp
                690                 695                 700

Lys Ile Lys Arg Ile Phe Glu Tyr Gln Asn Leu Lys Lys Leu Ile Glu
705                 710                 715                 720

Asn Lys Leu Leu Asn Lys Leu Asp Thr Tyr Val Arg Asn Cys Gly Lys
                725                 730                 735

Tyr Asn Tyr Tyr Leu Gln Asp Gly Glu Ile Ala Thr Ser Asp Phe Ile
                740                 745                 750

Ala Arg Asn Arg Gln Asn Glu Ala Phe Leu Arg Asn Ile Ile Gly Val
                755                 760                 765

Ser Ser Val Ala Tyr Phe Ser Leu Arg Asn Ile Leu Glu Thr Glu Asn
770                 775                 780

Glu Asn Asp Ile Thr Gly Arg Met Arg Gly Lys Thr Val Lys Asn Asn
785                 790                 795                 800

Lys Gly Glu Glu Lys Tyr Val Ser Gly Glu Val Asp Lys Ile Tyr Asn
                805                 810                 815

Glu Asn Lys Lys Asn Glu Val Lys Glu Asn Leu Lys Met Phe Tyr Ser
                820                 825                 830

Tyr Asp Phe Asn Met Asp Asn Lys Asn Glu Ile Glu Asp Phe Phe Ala
                835                 840                 845

Asn Ile Asp Glu Ala Ile Ser Ser Ile Arg His Gly Ile Val His Phe
850                 855                 860

Asn Leu Glu Leu Glu Gly Lys Asp Ile Phe Ala Phe Lys Asn Ile Ala
865                 870                 875                 880

Pro Ser Glu Ile Ser Lys Lys Met Phe Gln Asn Glu Ile Asn Glu Lys
                885                 890                 895

Lys Leu Lys Leu Lys Ile Phe Arg Gln Leu Asn Ser Ala Asn Val Phe
                900                 905                 910

Arg Tyr Leu Glu Lys Tyr Lys Ile Leu Asn Tyr Leu Lys Arg Thr Arg
                915                 920                 925

Phe Glu Phe Val Asn Lys Asn Ile Pro Phe Val Pro Ser Phe Thr Lys
                930                 935                 940

Leu Tyr Ser Arg Ile Asp Asp Leu Lys Asn Ser Leu Gly Ile Tyr Trp
945                 950                 955                 960
```

```
Lys Thr Pro Lys Thr Asn Asp Asp Asn Lys Thr Lys Glu Ile Ile Asp
                965                 970                 975

Ala Gln Ile Tyr Leu Leu Lys Asn Ile Tyr Tyr Gly Glu Phe Leu Asn
                980                 985                 990

Tyr Phe Met Ser Asn Asn Gly Asn Phe Phe Glu Ile Ser Lys Glu Ile
            995                 1000                1005

Ile Glu Leu Asn Lys Asn Asp Lys Arg Asn Leu Lys Thr Gly Phe
        1010                1015                1020

Tyr Lys Leu Gln Lys Phe Glu Asp Ile Gln Glu Lys Ile Pro Lys
        1025                1030                1035

Glu Tyr Leu Ala Asn Ile Gln Ser Leu Tyr Met Ile Asn Ala Gly
        1040                1045                1050

Asn Gln Asp Glu Glu Glu Lys Asp Thr Tyr Ile Asp Phe Ile Gln
        1055                1060                1065

Lys Ile Phe Leu Lys Gly Phe Met Thr Tyr Leu Ala Asn Asn Gly
        1070                1075                1080

Arg Leu Ser Leu Ile Tyr Ile Gly Ser Asp Glu Glu Thr Asn Thr
        1085                1090                1095

Ser Leu Ala Glu Lys Lys Gln Glu Phe Asp Lys Phe Leu Lys Lys
        1100                1105                1110

Tyr Glu Gln Asn Asn Asn Ile Lys Ile Pro Tyr Glu Ile Asn Glu
        1115                1120                1125

Phe Leu Arg Glu Ile Lys Leu Gly Asn Ile Leu Lys Tyr Thr Glu
        1130                1135                1140

Arg Leu Asn Met Phe Tyr Leu Ile Leu Lys Leu Leu Asn His Lys
        1145                1150                1155

Glu Leu Thr Asn Leu Lys Gly Ser Leu Glu Lys Tyr Gln Ser Ala
        1160                1165                1170

Asn Lys Glu Glu Ala Phe Ser Asp Gln Leu Glu Leu Ile Asn Leu
        1175                1180                1185

Leu Asn Leu Asp Asn Asn Arg Val Thr Glu Asp Phe Glu Leu Glu
        1190                1195                1200

Ala Asp Glu Ile Gly Lys Phe Leu Asp Phe Asn Gly Asn Lys Val
        1205                1210                1215

Lys Asp Asn Lys Glu Leu Lys Lys Phe Asp Thr Asn Lys Ile Tyr
        1220                1225                1230

Phe Asp Gly Glu Asn Ile Ile Lys His Arg Ala Phe Tyr Asn Ile
        1235                1240                1245

Lys Lys Tyr Gly Met Leu Asn Leu Leu Glu Lys Ile Ala Asp Lys
        1250                1255                1260

Ala Gly Tyr Lys Ile Ser Ile Glu Glu Leu Lys Lys Tyr Ser Asn
        1265                1270                1275

Lys Lys Asn Glu Ile Glu Lys Asn His Lys Met Gln Glu Asn Leu
        1280                1285                1290

His Arg Lys Tyr Ala Arg Pro Arg Lys Asp Glu Lys Phe Thr Asp
        1295                1300                1305

Glu Asp Tyr Glu Ser Tyr Lys Gln Ala Ile Glu Asn Ile Glu Glu
        1310                1315                1320

Tyr Thr His Leu Lys Asn Lys Val Glu Phe Asn Glu Leu Asn Leu
        1325                1330                1335

Leu Gln Gly Leu Leu Leu Arg Ile Leu His Arg Leu Val Gly Tyr
        1340                1345                1350
```

| | | | | | | | | | | | |
|---|---|---|---|---|---|---|---|---|---|---|---|
| Thr | Ser | Ile | Trp | Glu | Arg | Asp | Leu | Arg | Phe | Arg | Leu | Lys | Gly | Glu |
| | 1355 | | | | 1360 | | | | | 1365 | | | | |

Thr Ser Ile Trp Glu Arg Asp Leu Arg Phe Arg Leu Lys Gly Glu
    1355                1360                1365

Phe Pro Glu Asn Gln Tyr Ile Glu Glu Ile Phe Asn Phe Glu Asn
    1370                1375                1380

Lys Lys Asn Val Lys Tyr Lys Gly Gly Gln Ile Val Glu Lys Tyr
    1385                1390                1395

Ile Lys Phe Tyr Lys Glu Leu His Gln Asn Asp Glu Val Lys Ile
    1400                1405                1410

Asn Lys Tyr Ser Ser Ala Asn Ile Lys Val Leu Lys Gln Glu Lys
    1415                1420                1425

Lys Asp Leu Tyr Ile Arg Asn Tyr Ile Ala His Phe Asn Tyr Ile
    1430                1435                1440

Pro His Ala Glu Ile Ser Leu Leu Glu Val Leu Glu Asn Leu Arg
    1445                1450                1455

Lys Leu Leu Ser Tyr Asp Arg Lys Leu Lys Asn Ala Val Met Lys
    1460                1465                1470

Ser Val Val Asp Ile Leu Lys Glu Tyr Gly Phe Val Ala Thr Phe
    1475                1480                1485

Lys Ile Gly Ala Asp Lys Lys Ile Gly Ile Gln Thr Leu Glu Ser
    1490                1495                1500

Glu Lys Ile Val His Leu Lys Asn Leu Lys Lys Lys Leu Met
    1505                1510                1515

Thr Asp Arg Asn Ser Glu Glu Leu Cys Lys Leu Val Lys Ile Met
    1520                1525                1530

Phe Glu Tyr Lys Met Glu Glu Lys Lys Ser Glu Asn Asp Pro Asn
    1535                1540                1545

Ser Ser Ser Val Asp Lys Leu Ala Ala Ala Leu Glu His His His
    1550                1555                1560

His His His
    1565

<210> SEQ ID NO 5
<211> LENGTH: 4236
<212> TYPE: DNA
<213> ORGANISM: Artificial Sequence
<220> FEATURE:
<223> OTHER INFORMATION: Synthetic

<400> SEQUENCE: 5

```
atgggtaacc tgtttggtca taaacgttgg tatgaagtgc gcgacaaaaa agactttaaa      60
atcaaacgca aggtgaaagt gaaacgcaac tatgatggca acaaatatat cctgaacatc     120
aacgagaaca caacaaaga gaagatcgat aataataaat tcatccgcaa atacatcaac     180
tacaaaaaaa acgataacat cctgaaagaa ttcacccgca gtttcatgc aggcaacatt     240
ctgtttaaac tgaaaggcaa agaaggcatc attcgcatcg aaaacaatga tgattttctg     300
gaaaccgaag aggtggtgct gtatattgaa gcatatggca aaagcgaaaa actgaaggca     360
ctgggcatta ccaaaaaaaa gattatcgat gaagccattc gccagggtat taccaaagat     420
gacaaaaaga tcgagatcaa gcgccaagaa acgaagaag aaatcgaaat tgatatccgc     480
gacgagtata ccaataaaac cctgaatgat tgcagcatta ttctgcgcat tatcgagaat     540
gatgagctgg aaacgaaaaa gagcatctac gagatcttca aaaacatcaa catgagcctg     600
tacaaaatca tcgagaaaat tatcgaaaac gaaaccgaga aggtgttcga gaatcgctat     660
tatgaagaac atctgcgtga aaactgctg aaagatgata aaattgatgt gatcctgacc     720
```

-continued

```
aacttcatgg aaatccgcga aaagattaaa agcaacctgg aaattctggg cttcgtgaaa        780
ttctatctga atgttggtgg cgacaagaaa aaaagcaaga acaagaaaat gctggtcgaa        840
aaaattctga acattaacgt tgatctgacc gtggaagata ttgccgattt tgtgattaaa        900
gagctggaat tctggaacat caccaaacgc attgagaagg tgaaaaaagt gaacaacgag        960
ttcctggaaa aacgtcgtaa tcgcacctat atcaaaagct atgttctgct ggataagcac       1020
gagaaattca aaattgaacg cgagaacaaa aaggacaaaa tcgtgaagtt tttcgtggaa       1080
aatatcaaaa acaacagcat caaagaaaaa atcgagaaga tcctggccga gttcaaaatc       1140
gatgaactga tcaaaaagct ggaaaaagaa ctgaaaaaag gcaactgcga taccgaaatt       1200
ttcggcatct ttaagaaaca ctataaagtg aacttcgata gcaaaaaatt cagcaaaaag       1260
agcgacgaag agaaagagct gtataagatc atttaccgct atctgaaagg ccgtattgaa       1320
aaaatcctgg tgaatgaaca gaaagtgcgc ctgaaaaaaa tggaaaaaat tgagattgag       1380
aagattctga acgagagcat cctgagtgag aaaatcctga acgtgttaa acagtatacc        1440 ctggaacaca ttatgtatct gggtaaactg cgccataacg atattgatat gaccaccgtt       1500
aataccgatg atttcagccg tctgcatgca aaagaagaac tggatctgga actgattacc       1560 tttttttgcaa gcaccaatat ggaactgaac aagatctttta gccgtgaaaa cattaacaac      1620
gacgagaaca ttgatttctt tggtggtgat cgcgagaaaa actatgtcct ggataaaaag       1680
atcctgaata gcaaaatcaa gatcatccgc gatctggatt tcatcgacaa taagaacaac       1740
attaccaaca actttattcg caaatttacc aaaattggca ccaatgaacg caaccgtatt       1800
ctgcatgcca ttagcaaaga acgtgatctg cagggcaccc aggatgatta taacaaagtg       1860
attaacatca tccagaacct gaaaatctcc gatgaagaag ttagcaaagc actgaatctg       1920
gatgtggtgt tcaaagataa gaaaaatatc atcaccaaga tcaacgatat caaaatcagc       1980
gaagagaaca ataacgacat caaatatctg ccgagcttta gcaaagttct gccggaaatt       2040
cttaatctgt atcgcaataa cccgaaaaac gaaccgtttg ataccatcga aacagagaaa       2100
attgttctga acgccctgat ctatgtgaac aaagaactgt acaagaaact gatcctggaa       2160
gatgatctgg aagagaacga atcgaaaaac atctttctgc aagagctgaa aaagaccctg       2220
ggtaacattg atgagatcga tgaaaacatc atcgaaaatt actacaagaa cgcacagatt       2280
agcgcaagca aagtaataa caaagccatc aaaaaatacc agaaaaaggt gatcgaatgc       2340
tacattggtt atctgcgcaa aaactacgaa gaactgttcg atttcagcga tttcaaaatg       2400
aacatccaag agatcaagaa gcagatcaag gacattaacg acaacaaaac ctatgaacgc       2460
atcaccgtta aaaccagcga taaaaccatt gtgatcaacg acgatttcga gtacatcatt       2520
agcatttttg cactgctgaa ttccaacgcc gtgatcaaca aaattcgcaa tcgcttttt        2580 gccaccagtg tttggctgaa taccagcgaa tatcagaaca ttatcgatat cctggatgag       2640
atcatgcagc tgaatacact gcgtaatgaa tgcattaccg aaaactgaa tctgaacctt       2700 gaagaattta ttcagaaaat gaaagagatc gagaaagact cgacgactt caaaatccag        2760 accaaaaaag aaatcttcaa caactactac gaggacatca aaaataacat tctgaccgaa       2820
ttcaaagacg atattaacgg ctgtgacgtg ctggaaagaa gttggaaaa gatcgttatc       2880 ttcgatgacg aaaccaaatt cgaaatcgac aaaaagtcca acatccttca ggatgaacag       2940
cgtaaactga gcaatatcaa caagaaagac ctgaagaaga aggtcgacca gtacatcaaa       3000
gacaaagacc aagaaattaa gagcaaaatc ctgtgccgca tcatctttaa cagcgacttt       3060
ctgaaaaagt ataagaaaga gattgacaac ctgatcgagg atatggaaag cgagaacgaa       3120
```

```
aacaagtttc aagagatcta ctatccgaaa gaacgcaaaa acgagctgta catctacaag   3180
aagaacctgt tcctgaatat tggcaacccg aacttcgaca aatctatgg tctgatcagc   3240 aacgacatta aaatggccga tgcaaaattc ctgtttaata tcgatggtaa aaacatccgt   3300
aaaaacaaaa ttagcgagat cgacgcgatc ctgaaaaacc tgaacgataa actgaatggc   3360
tacagcaaag aatataaaga gaaatacatt aaaaagctga agaaaatga cgacttcttc   3420 gccaagaaca tccagaataa aaactataaa agcttcgaga aggactacaa tcgcgtgtcc   3480
gaatataaga aaattcgtga tctggtggaa ttcaactatc tgaacaaaat cgaaagctat   3540
ctgatcgata tcaactggaa actggcaatt cagatggcac gttttgagcg tgatatgcac   3600
tatattgtta atggtctgcg tgaactgggc atcattaaac tgagtggtta ataccggc    3660 attagccgtg catatccgaa acgtaatggt tccgatggtt tttataccac caccgcctat   3720
tacaaatttt tcgacgaaga aagctacaag aaatttgaga aaatttgcta cggcttcggc   3780
attgatctga gcgaaaatag cgaaattaac aagccggaaa atgagagcat tcgcaactat   3840
atctcccact tttatatcgt gcgtaatccg tttgccgatt atagcattgc agagcagatt   3900
gatcgtgtta gcaatctgct gagctatagt acccgttata acaatagcac ctatgccagc   3960
gtgtttgagg tgtttaaaaa ggatgttaac ctggactatg acgagctgaa gaaaaagttc   4020
aaactgatcg gcaacaatga catcctggaa cgtctgatga accgaaaaa agttagtgtg   4080 ctggaacttg agagctacaa cagcgattat atcaagaacc tgattatcga gctgctgacc   4140
aagattgaaa ataccaatga taccctgggg gatccgaatt cgagctccgt cgacaagctt   4200
gcggccgcac tcgagcacca ccaccaccac cactga                            4236
```

<210> SEQ ID NO 6
<211> LENGTH: 1411
<212> TYPE: PRT
<213> ORGANISM: Artificial Sequence
<220> FEATURE:
<223> OTHER INFORMATION: Synthetic

<400> SEQUENCE: 6

```
Met Gly Asn Leu Phe Gly His Lys Arg Trp Tyr Glu Val Arg Asp Lys
1               5                   10                  15

Lys Asp Phe Lys Ile Lys Arg Lys Val Lys Val Lys Arg Asn Tyr Asp
            20                  25                  30

Gly Asn Lys Tyr Ile Leu Asn Ile Asn Glu Asn Asn Lys Glu Lys
        35                  40                  45

Ile Asp Asn Asn Lys Phe Ile Arg Lys Tyr Ile Asn Tyr Lys Lys Asn
50                  55                  60

Asp Asn Ile Leu Lys Glu Phe Thr Arg Lys Phe His Ala Gly Asn Ile
65                  70                  75                  80

Leu Phe Lys Leu Lys Gly Lys Glu Gly Ile Ile Arg Ile Glu Asn Asn
                85                  90                  95

Asp Asp Phe Leu Glu Thr Glu Glu Val Val Leu Tyr Ile Glu Ala Tyr
            100                 105                 110

Gly Lys Ser Glu Lys Leu Lys Ala Leu Gly Ile Thr Lys Lys Lys Ile
        115                 120                 125

Ile Asp Glu Ala Ile Arg Gln Gly Ile Thr Lys Asp Lys Lys Ile
    130                 135                 140

Glu Ile Lys Arg Gln Glu Asn Glu Glu Ile Glu Ile Asp Ile Arg
145                 150                 155                 160
```

```
Asp Glu Tyr Thr Asn Lys Thr Leu Asn Asp Cys Ser Ile Ile Leu Arg
            165                 170                 175

Ile Ile Glu Asn Asp Glu Leu Glu Thr Lys Lys Ser Ile Tyr Glu Ile
            180                 185                 190

Phe Lys Asn Ile Asn Met Ser Leu Tyr Lys Ile Ile Glu Lys Ile Ile
            195                 200                 205

Glu Asn Glu Thr Glu Lys Val Phe Glu Asn Arg Tyr Tyr Glu Glu His
            210                 215                 220

Leu Arg Glu Lys Leu Leu Lys Asp Asp Lys Ile Asp Val Ile Leu Thr
225                 230                 235                 240

Asn Phe Met Glu Ile Arg Glu Lys Ile Lys Ser Asn Leu Glu Ile Leu
            245                 250                 255

Gly Phe Val Lys Phe Tyr Leu Asn Val Gly Gly Asp Lys Lys Lys Ser
            260                 265                 270

Lys Asn Lys Lys Met Leu Val Glu Lys Ile Leu Asn Ile Asn Val Asp
            275                 280                 285

Leu Thr Val Glu Asp Ile Ala Asp Phe Val Ile Lys Glu Leu Glu Phe
            290                 295                 300

Trp Asn Ile Thr Lys Arg Ile Glu Lys Val Lys Lys Val Asn Asn Glu
305                 310                 315                 320

Phe Leu Glu Lys Arg Arg Asn Arg Thr Tyr Ile Lys Ser Tyr Val Leu
            325                 330                 335

Leu Asp Lys His Glu Lys Phe Lys Ile Glu Arg Glu Asn Lys Lys Asp
            340                 345                 350

Lys Ile Val Lys Phe Phe Val Asn Ile Lys Asn Asn Ser Ile Lys
            355                 360                 365

Glu Lys Ile Glu Lys Ile Leu Ala Glu Phe Lys Ile Asp Glu Leu Ile
            370                 375                 380

Lys Lys Leu Glu Lys Glu Leu Lys Lys Gly Asn Cys Asp Thr Glu Ile
385                 390                 395                 400

Phe Gly Ile Phe Lys Lys His Tyr Lys Val Asn Phe Asp Ser Lys Lys
            405                 410                 415

Phe Ser Lys Lys Ser Asp Glu Glu Lys Glu Leu Tyr Lys Ile Ile Tyr
            420                 425                 430

Arg Tyr Leu Lys Gly Arg Ile Glu Lys Ile Leu Val Asn Glu Gln Lys
            435                 440                 445

Val Arg Leu Lys Lys Met Glu Lys Ile Glu Ile Glu Lys Ile Leu Asn
            450                 455                 460

Glu Ser Ile Leu Ser Glu Lys Ile Leu Lys Arg Val Lys Gln Tyr Thr
465                 470                 475                 480

Leu Glu His Ile Met Tyr Leu Gly Lys Leu Arg His Asn Asp Ile Asp
            485                 490                 495

Met Thr Thr Val Asn Thr Asp Asp Phe Ser Arg Leu His Ala Lys Glu
            500                 505                 510

Glu Leu Asp Leu Glu Leu Ile Thr Phe Ala Ser Thr Asn Met Glu
            515                 520                 525

Leu Asn Lys Ile Phe Ser Arg Glu Asn Ile Asn Asn Asp Glu Asn Ile
            530                 535                 540

Asp Phe Phe Gly Gly Asp Arg Glu Lys Asn Tyr Val Leu Asp Lys Lys
545                 550                 555                 560

Ile Leu Asn Ser Lys Ile Lys Ile Ile Arg Asp Leu Asp Phe Ile Asp
            565                 570                 575

Asn Lys Asn Asn Ile Thr Asn Asn Phe Ile Arg Lys Phe Thr Lys Ile
```

-continued

```
            580                 585                 590
Gly Thr Asn Glu Arg Asn Arg Ile Leu His Ala Ile Ser Lys Glu Arg
            595                 600                 605
Asp Leu Gln Gly Thr Gln Asp Tyr Asn Lys Val Ile Asn Ile Ile
            610                 615                 620
Gln Asn Leu Lys Ile Ser Asp Glu Glu Val Ser Lys Ala Leu Asn Leu
625                 630                 635                 640
Asp Val Val Phe Lys Asp Lys Asn Ile Ile Thr Lys Ile Asn Asp
            645                 650                 655
Ile Lys Ile Ser Glu Glu Asn Asn Asp Ile Lys Tyr Leu Pro Ser
            660                 665                 670
Phe Ser Lys Val Leu Pro Glu Ile Leu Asn Leu Tyr Arg Asn Asn Pro
            675                 680                 685
Lys Asn Glu Pro Phe Asp Thr Ile Glu Thr Lys Ile Val Leu Asn
            690                 695                 700
Ala Leu Ile Tyr Val Asn Lys Glu Leu Tyr Lys Lys Leu Ile Leu Glu
705                 710                 715                 720
Asp Asp Leu Glu Glu Asn Glu Ser Lys Asn Ile Phe Leu Gln Glu Leu
            725                 730                 735
Lys Lys Thr Leu Gly Asn Ile Asp Glu Ile Asp Glu Asn Ile Ile Glu
            740                 745                 750
Asn Tyr Tyr Lys Asn Ala Gln Ile Ser Ala Ser Lys Gly Asn Asn Lys
            755                 760                 765
Ala Ile Lys Lys Tyr Gln Lys Lys Val Ile Glu Cys Tyr Ile Gly Tyr
            770                 775                 780
Leu Arg Lys Asn Tyr Glu Glu Leu Phe Asp Phe Ser Asp Phe Lys Met
785                 790                 795                 800
Asn Ile Gln Glu Ile Lys Lys Gln Ile Lys Asp Ile Asn Asp Asn Lys
            805                 810                 815
Thr Tyr Glu Arg Ile Thr Val Lys Thr Ser Asp Lys Thr Ile Val Ile
            820                 825                 830
Asn Asp Asp Phe Glu Tyr Ile Ile Ser Ile Phe Ala Leu Leu Asn Ser
            835                 840                 845
Asn Ala Val Ile Asn Lys Ile Arg Asn Arg Phe Phe Ala Thr Ser Val
850                 855                 860
Trp Leu Asn Thr Ser Glu Tyr Gln Asn Ile Ile Asp Ile Leu Asp Glu
865                 870                 875                 880
Ile Met Gln Leu Asn Thr Leu Arg Asn Glu Cys Ile Thr Glu Asn Trp
            885                 890                 895
Asn Leu Asn Leu Glu Glu Phe Ile Gln Lys Met Lys Glu Ile Glu Lys
            900                 905                 910
Asp Phe Asp Asp Phe Lys Ile Gln Thr Lys Lys Glu Ile Phe Asn Asn
            915                 920                 925
Tyr Tyr Glu Asp Ile Lys Asn Asn Ile Leu Thr Glu Phe Lys Asp Asp
            930                 935                 940
Ile Asn Gly Cys Asp Val Leu Glu Lys Lys Leu Glu Lys Ile Val Ile
945                 950                 955                 960
Phe Asp Asp Glu Thr Lys Phe Glu Ile Asp Lys Lys Ser Asn Ile Leu
            965                 970                 975
Gln Asp Glu Gln Arg Lys Leu Ser Asn Ile Lys Lys Asp Leu Lys
            980                 985                 990
Lys Lys Val Asp Gln Tyr Ile Lys Asp Lys Asp Gln Glu Ile Lys Ser
            995                 1000                1005
```

```
Lys Ile Leu Cys Arg Ile Ile Phe Asn Ser Asp Phe Leu Lys Lys
    1010            1015                1020

Tyr Lys Lys Glu Ile Asp Asn Leu Ile Glu Asp Met Glu Ser Glu
    1025            1030                1035

Asn Glu Asn Lys Phe Gln Glu Ile Tyr Tyr Pro Lys Glu Arg Lys
    1040            1045                1050

Asn Glu Leu Tyr Ile Tyr Lys Lys Asn Leu Phe Leu Asn Ile Gly
    1055            1060                1065

Asn Pro Asn Phe Asp Lys Ile Tyr Gly Leu Ile Ser Asn Asp Ile
    1070            1075                1080

Lys Met Ala Asp Ala Lys Phe Leu Phe Asn Ile Asp Gly Lys Asn
    1085            1090                1095

Ile Arg Lys Asn Lys Ile Ser Glu Ile Asp Ala Ile Leu Lys Asn
    1100            1105                1110

Leu Asn Asp Lys Leu Asn Gly Tyr Ser Lys Glu Tyr Lys Glu Lys
    1115            1120                1125

Tyr Ile Lys Lys Leu Lys Glu Asn Asp Asp Phe Phe Ala Lys Asn
    1130            1135                1140

Ile Gln Asn Lys Asn Tyr Lys Ser Phe Glu Lys Asp Tyr Asn Arg
    1145            1150                1155

Val Ser Glu Tyr Lys Lys Ile Arg Asp Leu Val Glu Phe Asn Tyr
    1160            1165                1170

Leu Asn Lys Ile Glu Ser Tyr Leu Ile Asp Ile Asn Trp Lys Leu
    1175            1180                1185

Ala Ile Gln Met Ala Arg Phe Glu Arg Asp Met His Tyr Ile Val
    1190            1195                1200

Asn Gly Leu Arg Glu Leu Gly Ile Ile Lys Leu Ser Gly Tyr Asn
    1205            1210                1215

Thr Gly Ile Ser Arg Ala Tyr Pro Lys Arg Asn Gly Ser Asp Gly
    1220            1225                1230

Phe Tyr Thr Thr Thr Ala Tyr Tyr Lys Phe Phe Asp Glu Glu Ser
    1235            1240                1245

Tyr Lys Lys Phe Glu Lys Ile Cys Tyr Gly Phe Gly Ile Asp Leu
    1250            1255                1260

Ser Glu Asn Ser Glu Ile Asn Lys Pro Glu Asn Glu Ser Ile Arg
    1265            1270                1275

Asn Tyr Ile Ser His Phe Tyr Ile Val Arg Asn Pro Phe Ala Asp
    1280            1285                1290

Tyr Ser Ile Ala Glu Gln Ile Asp Arg Val Ser Asn Leu Leu Ser
    1295            1300                1305

Tyr Ser Thr Arg Tyr Asn Asn Ser Thr Tyr Ala Ser Val Phe Glu
    1310            1315                1320

Val Phe Lys Lys Asp Val Asn Leu Asp Tyr Asp Glu Leu Lys Lys
    1325            1330                1335

Lys Phe Lys Leu Ile Gly Asn Asn Asp Ile Leu Glu Arg Leu Met
    1340            1345                1350

Lys Pro Lys Lys Val Ser Val Leu Glu Leu Glu Ser Tyr Asn Ser
    1355            1360                1365

Asp Tyr Ile Lys Asn Leu Ile Ile Glu Leu Leu Thr Lys Ile Glu
    1370            1375                1380

Asn Thr Asn Asp Thr Leu Gly Asp Pro Asn Ser Ser Ser Val Asp
    1385            1390                1395
```

| Lys | Leu | Ala | Ala | Ala | Leu | Glu | His | His | His | His | His | His |
|---|---|---|---|---|---|---|---|---|---|---|---|---|
| 1400 | | | | | 1405 | | | | | 1410 | | |

<210> SEQ ID NO 7
<211> LENGTH: 5391
<212> TYPE: DNA
<213> ORGANISM: Artificial Sequence
<220> FEATURE:
<223> OTHER INFORMATION: Synthetic

<400> SEQUENCE: 7

```
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca agcgttcca ggacaagctg tatccgttta cctgggatgc cgtacgttac      300
aacggcaagc tgattgctta cccgatcgct gttgaagcgt tatcgctgat ttataacaaa     360
gatctgctgc cgaacccgcc aaaaacctgg gaagagatcc cggcgctgga taagaactg      420
aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat aacgccgcc agtccgaaca agagctggc aaaagagttc       840
ctcgaaaact atctgctgac tgatgaaggt ctggaagcgg ttaataaaga caaaccgctg     900
ggtgccgtag cgctgaagtc ttacgaggaa gagttggtga agatccgcg tattgccgcc      960
actatggaaa acgcccagaa aggtgaaatc atgccgaaca tcccgcagat gtccgctttc    1020
tggtatgccg tgcgtactgc ggtgatcaac gccgccagcg tcgtcagac tgtcgatgaa      1080
gccctgaaag acgcgcagac taattcgagc tcgaacaaca caacaataa caataacaac     1140
aacctcggga tcgagggaag gggtaacctg tttggtcata acgttggta tgaagtgcgc      1200
gacaaaaaag actttaaaat caaacgcaag gtgaaagtga acgcaacta tgatggcaac     1260
aaatatatcc tgaacatcaa cgagaacaac aacaaagaga agatcgataa taataaattc    1320
atccgcaaat acatcaacta caaaaaaaac gataacatcc tgaaagaatt cacccgcaag    1380
tttcatgcag gcaacattct gtttaaactg aaaggcaaag aaggcatcat tcgcatcgaa    1440
aacaatgatg attttctgga aaccgaagag gtggtgctgt atattgaagc atatggcaaa    1500
agcgaaaaac tgaaggcact gggcattacc aaaaaaaaga ttatcgatga agccattcgc    1560
cagggtatta ccaaagatga caaaagatc gagatcaagc gccaagaaaa cgaagaagaa     1620
atcgaaattg atatccgcga cgagtatacc aataaaaccc tgaatgattg cagcattatt    1680
ctgcgcatta tcgagaatga tgagctggaa acgaaaaaga gcatctacga gatcttcaaa    1740
aacatcaaca tgagcctgta caaatcatc gagaaaatta tcgaaaacga accgagaag     1800
gtgttcgaga atcgctatta tgaagaacat ctgcgtgaga actgctgaa agatgataaa     1860
attgatgtga tcctgaccaa cttcatggaa atccgcgaaa agattaaaag caacctggaa    1920
attctgggct tcgtgaaatt ctatctgaat gttggtggcg acaagaaaaa aagcaagaac    1980
```

```
aagaaaatgc tggtcgaaaa aattctgaac attaacgttg atctgaccgt ggaagatatt    2040
gccgattttg tgattaaaga gctggaattc tggaacatca ccaaacgcat tgagaaggtg    2100
aaaaaagtga acaacgagtt cctggaaaaa cgtcgtaatc gcacctatat caaaagctat    2160
gttctgctgg ataagcacga gaaattcaaa attgaacgcg agaacaaaaa ggacaaaatc    2220
gtgaagtttt tcgtggaaaa tatcaaaaac aacagcatca agaaaaaat cgagaagatc     2280 ctggccgagt tcaaaatcga tgaactgatc aaaaagctgg aaaaagaact gaaaaaaggc    2340
aactgcgata ccgaattttt cggcatcttt aagaaacact ataaagtgaa cttcgatagc    2400
aaaaaattca gcaaaagag cgacgaagag aaagagctgt ataagatcat ttaccgctat     2460
ctgaaaggcc gtattgaaaa aatcctggtg aatgaacaga agtgcgcct gaaaaaaatg     2520 gaaaaaattg agattgagaa gattctgaac gagagcatcc tgagtgagaa atcctgaaa     2580 cgtgttaaac agtatacct ggaacacatt atgtatctgg gtaaactgcg ccataacgat     2640
attgatatga ccaccgttaa taccgatgat ttcagccgtc tgcatgcaaa agaagaactg    2700
gatctggaac tgattacctt ttttgcaagc accaatatgg aactgaacaa gatctttagc    2760
cgtgaaaaca ttaacaacga cgagaacatt gatttctttg gtggtgatcg cgagaaaaac    2820
tatgtcctgg ataaaaagat cctgaatagc aaaatcaaga tcatccgcga tctggatttc    2880
atcgacaata gaacaacat taccaacaac tttattcgca aatttaccaa aattggcacc     2940
aatgaacgca accgtattct gcatgccatt agcaaagaac gtgatctgca gggcacccag    3000
gatgattata caaagtgat taacatcatc cagaacctga aaatctccga tgaagaagtt     3060
agcaaagcac tgaatctgga tgtggtgttc aaagataaga aaaatatcat caccaagatc    3120
aacgatatca aaatcagcga agagaacaat aacgacatca atatctgcc gagctttagc     3180 aaagttctgc cggaaattct taatctgtat cgcaataacc cgaaaaacga accgtttgat    3240
accatcgaaa cagagaaaat tgttctgaac gccctgatct atgtgaacaa agaactgtac    3300
aagaaactga tcctggaaga tgatctggaa gagaacgaat cgaaaaacat ctttctgcaa    3360
gagctgaaaa agaccctggg taacattgat gagatcgatg aaaacatcat cgaaaattac    3420
tacaagaacg cacagattag cgcaagcaaa ggtaataaca aagccatcaa aaaataccag    3480
aaaaaggtga tcgaatgcta cattggttat ctgcgcaaaa actacgaaga actgttcgat    3540
ttcagcgatt tcaaaatgaa catccaagag atcaagaagc agatcaagga cattaacgac    3600
aacaaaacct atgaacgcat caccgttaaa accagcgata aaaccattgt gatcaacgac    3660
gatttcgagt acatcattag cattttttgca ctgctgaatt ccaacgccgt gatcaacaaa    3720
attcgcaatc gcttttttgc caccagtgtt tggctgaata ccagcgaata tcagaacatt    3780
atcgatatcc tggatgagat catgcagctg aatacactgc gtaatgaatg cattaccgaa    3840
aactggaatc tgaaccttga agaatttatt cagaaaatga aagagatcga aaagacttc     3900 gacgacttca aaatccagac caaaaaagaa atcttcaaca actactacga ggacatcaaa    3960
aataacattc tgaccgaatt caagacgat attaacggct gtgacgtgct ggaaaagaag     4020
ttggaaaaga tcgttatctt cgatgacgaa accaaattcg aaatcgacaa aaagtccaac    4080
atccttcagg atgaacagcg taaactgagc aatatcaaca agaaagacct gaagaagaag    4140
gtcgaccagt acatcaaaga caaagaccaa gaaattaaga gcaaaatcct gtgccgcatc    4200
atctttaaca gcgactttct gaaaaagtat aagaaagaga ttgacaacct gatcgaggat    4260
atggaaagcg agaacgaaaa caagtttcaa gagatctact atccgaaaga acgcaaaaac    4320
gagctgtaca tctacaagaa gaacctgttc ctgaatattg caacccgaa cttcgacaaa     4380
```

```
atctatggtc tgatcagcaa cgacattaaa atggccgatg caaaattcct gtttaatatc   4440
gatggtaaaa acatccgtaa aaacaaaatt agcgagatcg acgcgatcct gaaaaacctg   4500
aacgataaac tgaatggcta cagcaaagaa tataaagaga atacattaa aaagctgaaa    4560 gaaaatgacg acttcttcgc caagaacatc cagaataaaa actataaaag cttcgagaag   4620
gactacaatc gcgtgtccga atataagaaa attcgtgatc tggtggaatt caactatctg   4680
aacaaaatcg aaagctatct gatcgatatc aactggaaac tggcaattca gatggcacgt   4740
tttgagcgtg atatgcacta tattgttaat ggtctgcgtg aactgggcat cattaaactg   4800
agtggttata ataccggcat tagccgtgca tatccgaaac gtaatggttc cgatggtttt   4860
tataccacca ccgcctatta caaattttc gacgaagaaa gctacaagaa atttgagaaa    4920
atttgctacg gcttcggcat tgatctgagc gaaaatagcg aaattaacaa gccggaaaat   4980
gagagcattc gcaactatat ctcccacttt tatatcgtgc gtaatccgtt tgccgattat   5040
agcattgcag agcagattga tcgtgttagc aatctgctga gctatagtac ccgttataac   5100
aatagcacct atgccagcgt gtttgaggtg tttaaaaagg atgttaacct ggactatgac   5160
gagctgaaga aaaagttcaa actgatcggc aacaatgaca tcctggaacg tctgatgaaa   5220
ccgaaaaaag ttagtgtgct ggaacttgag agctacaaca gcgattatat caagaacctg   5280
attatcgagc tgctgaccaa gattgaaaat accaatgata ccctggatcc gaattcgagc   5340
tccgtcgaca gcttgcggc cgcactcgag caccaccacc accaccactg a             5391
```

<210> SEQ ID NO 8
<211> LENGTH: 1796
<212> TYPE: PRT
<213> ORGANISM: Artificial Sequence
<220> FEATURE:
<223> OTHER INFORMATION: Synthetic

<400> SEQUENCE: 8

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
```

```
              180             185             190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
        210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
                260                 265                 270
Asn Lys Glu Leu Ala Lys Glu Phe Leu Glu Asn Tyr Leu Leu Thr Asp
            275                 280                 285
Glu Gly Leu Glu Ala Val Asn Lys Asp Lys Pro Leu Gly Ala Val Ala
            290                 295                 300
Leu Lys Ser Tyr Glu Glu Leu Val Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Asn
            355                 360                 365
Ser Ser Ser Asn Asn Asn Asn Asn Asn Asn Asn Asn Leu Gly Ile
            370                 375                 380
Glu Gly Arg Gly Asn Leu Phe Gly His Lys Arg Trp Tyr Glu Val Arg
385                 390                 395                 400
Asp Lys Lys Asp Phe Lys Ile Lys Arg Lys Val Lys Val Lys Arg Asn
                405                 410                 415
Tyr Asp Gly Asn Lys Tyr Ile Leu Asn Ile Asn Glu Asn Asn Asn Lys
                420                 425                 430
Glu Lys Ile Asp Asn Asn Lys Phe Ile Arg Lys Tyr Ile Asn Tyr Lys
            435                 440                 445
Lys Asn Asp Asn Ile Leu Lys Glu Phe Thr Arg Lys Phe His Ala Gly
            450                 455                 460
Asn Ile Leu Phe Lys Leu Lys Gly Lys Glu Gly Ile Ile Arg Ile Glu
465                 470                 475                 480
Asn Asn Asp Asp Phe Leu Glu Thr Glu Glu Val Val Leu Tyr Ile Glu
                485                 490                 495
Ala Tyr Gly Lys Ser Glu Lys Leu Lys Ala Leu Gly Ile Thr Lys Lys
                500                 505                 510
Lys Ile Ile Asp Glu Ala Ile Arg Gln Gly Ile Thr Lys Asp Asp Lys
            515                 520                 525
Lys Ile Glu Ile Lys Arg Gln Glu Asn Glu Glu Ile Glu Ile Asp
            530                 535                 540
Ile Arg Asp Glu Tyr Thr Asn Lys Thr Leu Asn Asp Cys Ser Ile Ile
545                 550                 555                 560
Leu Arg Ile Ile Glu Asn Asp Glu Leu Glu Thr Lys Lys Ser Ile Tyr
                565                 570                 575
Glu Ile Phe Lys Asn Ile Asn Met Ser Leu Tyr Lys Ile Ile Glu Lys
                580                 585                 590
Ile Ile Glu Asn Glu Thr Glu Lys Val Phe Glu Asn Arg Tyr Tyr Glu
            595                 600                 605
```

-continued

Glu His Leu Arg Glu Lys Leu Leu Lys Asp Asp Lys Ile Asp Val Ile
610             615             620

Leu Thr Asn Phe Met Glu Ile Arg Glu Lys Ile Lys Ser Asn Leu Glu
625             630             635             640

Ile Leu Gly Phe Val Lys Phe Tyr Leu Asn Val Gly Gly Asp Lys Lys
                645             650             655

Lys Ser Lys Asn Lys Lys Met Leu Val Glu Lys Ile Leu Asn Ile Asn
                660             665             670

Val Asp Leu Thr Val Glu Asp Ile Ala Asp Phe Val Ile Lys Glu Leu
            675             680             685

Glu Phe Trp Asn Ile Thr Lys Arg Ile Glu Lys Val Lys Lys Val Asn
690             695             700

Asn Glu Phe Leu Glu Lys Arg Arg Asn Arg Thr Tyr Ile Lys Ser Tyr
705             710             715             720

Val Leu Leu Asp Lys His Glu Lys Phe Lys Ile Glu Arg Glu Asn Lys
                725             730             735

Lys Asp Lys Ile Val Lys Phe Phe Val Glu Asn Ile Lys Asn Asn Ser
                740             745             750

Ile Lys Glu Lys Ile Glu Lys Ile Leu Ala Glu Phe Lys Ile Asp Glu
            755             760             765

Leu Ile Lys Lys Leu Glu Lys Glu Leu Lys Lys Gly Asn Cys Asp Thr
770             775             780

Glu Ile Phe Gly Ile Phe Lys Lys His Tyr Lys Val Asn Phe Asp Ser
785             790             795             800

Lys Lys Phe Ser Lys Lys Ser Asp Glu Glu Lys Glu Leu Tyr Lys Ile
                805             810             815

Ile Tyr Arg Tyr Leu Lys Gly Arg Ile Glu Lys Ile Leu Val Asn Glu
                820             825             830

Gln Lys Val Arg Leu Lys Lys Met Glu Lys Ile Glu Ile Glu Lys Ile
            835             840             845

Leu Asn Glu Ser Ile Leu Ser Glu Lys Ile Leu Lys Arg Val Lys Gln
850             855             860

Tyr Thr Leu Glu His Ile Met Tyr Leu Gly Lys Leu Arg His Asn Asp
865             870             875             880

Ile Asp Met Thr Thr Val Asn Thr Asp Asp Phe Ser Arg Leu His Ala
                885             890             895

Lys Glu Glu Leu Asp Leu Glu Leu Ile Thr Phe Phe Ala Ser Thr Asn
                900             905             910

Met Glu Leu Asn Lys Ile Phe Ser Arg Glu Asn Ile Asn Asn Asp Glu
            915             920             925

Asn Ile Asp Phe Phe Gly Gly Asp Arg Glu Lys Asn Tyr Val Leu Asp
930             935             940

Lys Lys Ile Leu Asn Ser Lys Ile Lys Ile Ile Arg Asp Leu Asp Phe
945             950             955             960

Ile Asp Asn Lys Asn Asn Ile Thr Asn Asn Phe Ile Arg Lys Phe Thr
                965             970             975

Lys Ile Gly Thr Asn Glu Arg Asn Arg Ile Leu His Ala Ile Ser Lys
            980             985             990

Glu Arg Asp Leu Gln Gly Thr Gln Asp Asp Tyr Asn Lys Val Ile Asn
            995             1000            1005

Ile Ile Gln Asn Leu Lys Ile Ser Asp Glu Glu Val Ser Lys Ala
        1010            1015            1020

```
Leu Asn Leu Asp Val Val Phe Lys Asp Lys Lys Asn Ile Ile Thr
1025                1030                1035

Lys Ile Asn Asp Ile Lys Ile Ser Glu Glu Asn Asn Asn Asp Ile
1040                1045                1050

Lys Tyr Leu Pro Ser Phe Ser Lys Val Leu Pro Glu Ile Leu Asn
1055                1060                1065

Leu Tyr Arg Asn Asn Pro Lys Asn Glu Pro Phe Asp Thr Ile Glu
1070                1075                1080

Thr Glu Lys Ile Val Leu Asn Ala Leu Ile Tyr Val Asn Lys Glu
1085                1090                1095

Leu Tyr Lys Lys Leu Ile Leu Glu Asp Asp Leu Glu Glu Asn Glu
1100                1105                1110

Ser Lys Asn Ile Phe Leu Gln Glu Leu Lys Lys Thr Leu Gly Asn
1115                1120                1125

Ile Asp Glu Ile Asp Glu Asn Ile Ile Glu Asn Tyr Tyr Lys Asn
1130                1135                1140

Ala Gln Ile Ser Ala Ser Lys Gly Asn Asn Lys Ala Ile Lys Lys
1145                1150                1155

Tyr Gln Lys Lys Val Ile Glu Cys Tyr Ile Gly Tyr Leu Arg Lys
1160                1165                1170

Asn Tyr Glu Glu Leu Phe Asp Phe Ser Asp Phe Lys Met Asn Ile
1175                1180                1185

Gln Glu Ile Lys Lys Gln Ile Lys Asp Ile Asn Asp Asn Lys Thr
1190                1195                1200

Tyr Glu Arg Ile Thr Val Lys Thr Ser Asp Lys Thr Ile Val Ile
1205                1210                1215

Asn Asp Asp Phe Glu Tyr Ile Ile Ser Ile Phe Ala Leu Leu Asn
1220                1225                1230

Ser Asn Ala Val Ile Asn Lys Ile Arg Asn Arg Phe Phe Ala Thr
1235                1240                1245

Ser Val Trp Leu Asn Thr Ser Glu Tyr Gln Asn Ile Ile Asp Ile
1250                1255                1260

Leu Asp Glu Ile Met Gln Leu Asn Thr Leu Arg Asn Glu Cys Ile
1265                1270                1275

Thr Glu Asn Trp Asn Leu Asn Leu Glu Glu Phe Ile Gln Lys Met
1280                1285                1290

Lys Glu Ile Glu Lys Asp Phe Asp Asp Phe Lys Ile Gln Thr Lys
1295                1300                1305

Lys Glu Ile Phe Asn Asn Tyr Tyr Glu Asp Ile Lys Asn Asn Ile
1310                1315                1320

Leu Thr Glu Phe Lys Asp Asp Ile Asn Gly Cys Asp Val Leu Glu
1325                1330                1335

Lys Lys Leu Glu Lys Ile Val Ile Phe Asp Asp Glu Thr Lys Phe
1340                1345                1350

Glu Ile Asp Lys Lys Ser Asn Ile Leu Gln Asp Glu Gln Arg Lys
1355                1360                1365

Leu Ser Asn Ile Asn Lys Lys Asp Leu Lys Lys Val Asp Gln
1370                1375                1380

Tyr Ile Lys Asp Lys Asp Gln Glu Ile Lys Ser Lys Ile Leu Cys
1385                1390                1395

Arg Ile Ile Phe Asn Ser Asp Phe Leu Lys Lys Tyr Lys Lys Glu
1400                1405                1410

Ile Asp Asn Leu Ile Glu Asp Met Glu Ser Glu Asn Glu Asn Lys
```

```
                1415                1420                1425

Phe Gln Glu Ile Tyr Tyr Pro Lys Glu Arg Lys Asn Glu Leu Tyr
            1430                1435                1440

Ile Tyr Lys Lys Asn Leu Phe Leu Asn Ile Gly Asn Pro Asn Phe
            1445                1450                1455

Asp Lys Ile Tyr Gly Leu Ile Ser Asn Asp Ile Lys Met Ala Asp
            1460                1465                1470

Ala Lys Phe Leu Phe Asn Ile Asp Gly Lys Asn Ile Arg Lys Asn
            1475                1480                1485

Lys Ile Ser Glu Ile Asp Ala Ile Leu Lys Asn Leu Asn Asp Lys
            1490                1495                1500

Leu Asn Gly Tyr Ser Lys Glu Tyr Lys Glu Lys Tyr Ile Lys Lys
            1505                1510                1515

Leu Lys Glu Asn Asp Asp Phe Phe Ala Lys Asn Ile Gln Asn Lys
            1520                1525                1530

Asn Tyr Lys Ser Phe Glu Lys Asp Tyr Asn Arg Val Ser Glu Tyr
            1535                1540                1545

Lys Lys Ile Arg Asp Leu Val Glu Phe Asn Tyr Leu Asn Lys Ile
            1550                1555                1560

Glu Ser Tyr Leu Ile Asp Ile Asn Trp Lys Leu Ala Ile Gln Met
            1565                1570                1575

Ala Arg Phe Glu Arg Asp Met His Tyr Ile Val Asn Gly Leu Arg
            1580                1585                1590

Glu Leu Gly Ile Ile Lys Leu Ser Gly Tyr Asn Thr Gly Ile Ser
            1595                1600                1605

Arg Ala Tyr Pro Lys Arg Asn Gly Ser Asp Gly Phe Tyr Thr Thr
            1610                1615                1620

Thr Ala Tyr Tyr Lys Phe Phe Asp Glu Glu Ser Tyr Lys Lys Phe
            1625                1630                1635

Glu Lys Ile Cys Tyr Gly Phe Gly Ile Asp Leu Ser Glu Asn Ser
            1640                1645                1650

Glu Ile Asn Lys Pro Glu Asn Glu Ser Ile Arg Asn Tyr Ile Ser
            1655                1660                1665

His Phe Tyr Ile Val Arg Asn Pro Phe Ala Asp Tyr Ser Ile Ala
            1670                1675                1680

Glu Gln Ile Asp Arg Val Ser Asn Leu Leu Ser Tyr Ser Thr Arg
            1685                1690                1695

Tyr Asn Asn Ser Thr Tyr Ala Ser Val Phe Glu Val Phe Lys Lys
            1700                1705                1710

Asp Val Asn Leu Asp Tyr Asp Glu Leu Lys Lys Lys Phe Lys Leu
            1715                1720                1725

Ile Gly Asn Asn Asp Ile Leu Glu Arg Leu Met Lys Pro Lys Lys
            1730                1735                1740

Val Ser Val Leu Glu Leu Glu Ser Tyr Asn Ser Asp Tyr Ile Lys
            1745                1750                1755

Asn Leu Ile Ile Glu Leu Leu Thr Lys Ile Glu Asn Thr Asn Asp
            1760                1765                1770

Thr Leu Asp Pro Asn Ser Ser Ser Val Asp Lys Leu Ala Ala Ala
            1775                1780                1785

Leu Glu His His His His His
            1790                1795

<210> SEQ ID NO 9
```

<211> LENGTH: 3525
<212> TYPE: DNA
<213> ORGANISM: Artificial Sequence
<220> FEATURE:
<223> OTHER INFORMATION: Synthetic

<400> SEQUENCE: 9

| | |
|---|---|
| atgaaagtga ccaaagtgga tggcatcagc cacaaaaaat acatcgaaga aggcaaactg | 60 |
| gttaaaagca ccagcgaaga aaatcgtacc agcgaacgtc tgagcgaact gctgagcatt | 120 |
| cgtctggata tctatatcaa aaatccggat aatgccagcg aggaagaaaa ccgtattcgt | 180 |
| cgtgaaaacc tgaaaaagtt cttcagcaat aaagtgctgc acctgaaaga tagcgttctg | 240 |
| tatctgaaaa accgcaaaga aaaaaatgcc gtgcaggaca aaaactatag cgaagaggat | 300 |
| atcagcgagt atgacctgaa gaacaaaaat agctttagcg tgctgaaaaa aatcctgctg | 360 |
| aatgaagatg tgaatagcga ggaactggaa atctttcgta agatgttgga agccaagctg | 420 |
| aacaaaatca cagcctgaa atatagcttt gaagaaaaca aggccaacta tcagaaaatc | 480 |
| aacgagaaca acgtggaaaa agttggtggt aaaagcaaac gcaacatcat ctatgattat | 540 |
| tatcgcgaaa gcgcgaaacg caacgattat atcaataatg tgcaagaggc cttcgacaaa | 600 |
| ctgtacaaaa agaggacat cgaaaaactg ttttttctga tcgagaacag caagaagcac | 660 |
| gagaaataca aaatccgcga gtactaccat aaaatcatcg gtcgcaaaaa cgataaagag | 720 |
| aacttcgcca aatcatcta cgaagaaatt cagaacgtga caacatcaa agaactgatc | 780 |
| gaaaaaattc cggacatgag cgagctgaag aaaagccagg tgttctataa atactacctg | 840 |
| gacaagagg aactgaacga caaaaacatc aaatatgcct tttgccactt cgtcgaaatt | 900 |
| gaaatgagcc agctgcttaa aaactacgtg tataaacgcc tgagcaacat cagcaacgat | 960 |
| aaaatcaaac gtatctttga atatcagaat ctgaagaaac tgattgaaaa caaactgctg | 1020 |
| aacaagctgg ataccctatgt tcgtaattgc ggcaaataca actactatct gcaggttggt | 1080 |
| gaaattgcaa ccagcgattt tattgcacgt aatcgtcaga tgaagccctt ctgcgtaac | 1140 |
| attattggtg ttagcagcgt tgcatatttt agcctgcgta atattctgga aaccgaaaac | 1200 |
| gaaaatggca ttaccggtcg tatgcgtggt aaaaccgtta aaacaataa aggcgaagag | 1260 |
| aagtatgtga gcggtgaagt ggataaaatc tataacgaaa acaagcagaa cgaagtgaaa | 1320 |
| gaaaatctga aaatgtttta cagctacgac ttcaacatgg acaacaaaaa cgagatcgaa | 1380 |
| gatttcttcg ccaacattga tgaagccatt agcagtattc gtcatggcat tgtgcacttt | 1440 |
| aatctggaac ttgaaggcaa agacatcttc gcgtttaaaa acattgcacc gagcgagatc | 1500 |
| agcaaaaaaa tgtttcagaa cgagattaac gaaaaaaaac tgaaactgaa atcttcaaa | 1560 |
| cagctgaata cgccaacgt gttcaactat tatgagaaag acgtgatcat caaatacctt | 1620 |
| aaaaacacca attcaacttt cgtgaataaa acatcccgtt tgttccgag cttcaccaaa | 1680 |
| ctgtataaca aaattgaaga tctgcgcaat accctgaagt ttttttggag cgttccgaaa | 1740 |
| gacaaagaag aaaagacgc acagatctac ctgcttaaga acatctatta tggcgaattt | 1800 |
| ctgaacaaat tcgtgaaaaa tagcaaagtg ttcttcaaaa tcaccaacga ggtgatcaag | 1860 |
| attaacaaac agcgtaatca gaaaccggt cactacaaat accagaagtt tgagaacatt | 1920 |
| gaaaaaaccg tgccggttga atatctggca attattcaga gccgtgagat gattaacaac | 1980 |
| caggataaag aagagaaaaa cacctacatc gatttcatcc agcagatctt tctgaaaggc | 2040 |
| tttatcgatt acctgaacaa gaacaacctg aagtatatcg agtcgaacaa caataacgac | 2100 |
| aacaacgaca tctttagcaa aatcaaaatc aagaaagata taaagaaaa atacgacaag | 2160 |

-continued

```
atcctgaaaa actatgagaa gcacaaccgc aacaaagaaa ttccgcatga gatcaatgaa      2220
tttgtgcgcg aaattaaact gggcaaaatc ctgaaataca ccgagaacct gaatatgttc      2280
tatctgattc tgaagctgct gaaccataaa gagctgacca atctgaaagg tagcctggaa      2340
aaatatcaga gcgcaaacaa agaagagaca ttttctgacg aactggaact gattaatctg      2400
ctgaatctgg ataataaccg tgtgaccgaa gatttttgaac tggaagcaaa tgaaatcggc      2460
aaattcctgg atttcaatga gaacaaaatt aaggaccgga aagagcttaa aaagtttgat      2520
accaacaaaa tctacttcga cggcgagaac attatcaaac atcgtgcctt ttataacatc      2580
aaaaagtatg gcatgctgaa cctgctggaa aaaattgcag ataaagccaa gtacaaaatt      2640
agcctgaaag aacttaaaga gtacagcaac aaaaagaacg aaatcgagaa gaactatacc      2700
atgcagcaga atctgcatcg taaatatgca cgtccgaaaa aagacgagaa attcaacgat      2760
gaggactata agaatacgga aaagccattg gcaacatcc agaaatatac ccacttgaaa       2820
aacaaagtgg aatttaacga gctgaattta ctgcagggtc tgctgctgaa aattctgcac      2880
cgtctggttg gttataccag catttgggaa cgtgatctgc gttttcgcct gaaaggtgaa      2940
tttcctgaaa accactatat cgaggaaatt ttcaactttg acaacagcaa aaacgtgaaa      3000
tataagagcg gtcagatcgt cgaaaagtac atcaactttt acaagaaact ttacaaggat      3060
aatgtggaaa aacgcagcat ctacagcgac aagaaagtga aaagctgaa gcaagaaaag        3120 aaagacctgt acatccgtaa ttatatcgcc cactttaact atatcccgca tgcagaaatt      3180
agtctgctgg aagttctgga aaatctgcgt aaactgctgt catatgatcg caaactgaag      3240
aacgcaatca tgaaaagcat tgtggatatc ctgaaagagt atggttttgt cgccaccttt      3300
aaaatcggtg ccgataagaa aattgagatt cagaccctgg aaagcgagaa aattgtgcat      3360
cttaagaacc ttaaaaagaa aaaactgatg accgatcgca acagcgaaga gttatgtgaa      3420
ctggtgaaag tgatgttcga atacaaagca ctggaagggg atccgaattc gagctccgtc      3480
gacaagcttg cggccgcact cgagcaccac caccaccacc actga                      3525
```

<210> SEQ ID NO 10  
<211> LENGTH: 1174  
<212> TYPE: PRT  
<213> ORGANISM: Artificial Sequence  
<220> FEATURE:  
<223> OTHER INFORMATION: Synthetic

<400> SEQUENCE: 10

```
Met Lys Val Thr Lys Val Asp Gly Ile Ser His Lys Lys Tyr Ile Glu
1               5                   10                  15

Glu Gly Lys Leu Val Lys Ser Thr Ser Glu Glu Asn Arg Thr Ser Glu
            20                  25                  30

Arg Leu Ser Glu Leu Leu Ser Ile Arg Leu Asp Ile Tyr Ile Lys Asn
        35                  40                  45

Pro Asp Asn Ala Ser Glu Glu Asn Arg Ile Arg Arg Glu Asn Leu
    50                  55                  60

Lys Lys Phe Phe Ser Asn Lys Val Leu His Leu Lys Asp Ser Val Leu
65                  70                  75                  80

Tyr Leu Lys Asn Arg Lys Glu Lys Asn Ala Val Gln Asp Lys Asn Tyr
                85                  90                  95

Ser Glu Glu Asp Ile Ser Glu Tyr Asp Leu Lys Asn Lys Asn Ser Phe
            100                 105                 110

Ser Val Leu Lys Lys Ile Leu Leu Asn Glu Asp Val Asn Ser Glu Glu
```

-continued

```
            115                 120                 125
Leu Glu Ile Phe Arg Lys Asp Val Glu Ala Lys Leu Asn Lys Ile Asn
    130                 135                 140
Ser Leu Lys Tyr Ser Phe Glu Glu Asn Lys Ala Asn Tyr Gln Lys Ile
145                 150                 155                 160
Asn Glu Asn Asn Val Glu Lys Val Gly Gly Lys Ser Lys Arg Asn Ile
                165                 170                 175
Ile Tyr Asp Tyr Arg Glu Ser Ala Lys Arg Asn Asp Tyr Ile Asn
            180                 185                 190
Asn Val Gln Glu Ala Phe Asp Lys Leu Tyr Lys Lys Glu Asp Ile Glu
            195                 200                 205
Lys Leu Phe Phe Leu Ile Glu Asn Ser Lys Lys His Glu Lys Tyr Lys
    210                 215                 220
Ile Arg Glu Tyr Tyr His Lys Ile Ile Gly Arg Lys Asn Asp Lys Glu
225                 230                 235                 240
Asn Phe Ala Lys Ile Ile Tyr Glu Glu Ile Gln Asn Val Asn Asn Ile
                245                 250                 255
Lys Glu Leu Ile Glu Lys Ile Pro Asp Met Ser Glu Leu Lys Lys Ser
            260                 265                 270
Gln Val Phe Tyr Lys Tyr Tyr Leu Asp Lys Glu Leu Asn Asp Lys
    275                 280                 285
Asn Ile Lys Tyr Ala Phe Cys His Phe Val Glu Ile Glu Met Ser Gln
    290                 295                 300
Leu Leu Lys Asn Tyr Val Tyr Lys Arg Leu Ser Asn Ile Ser Asn Asp
305                 310                 315                 320
Lys Ile Lys Arg Ile Phe Glu Tyr Gln Asn Leu Lys Lys Leu Ile Glu
                325                 330                 335
Asn Lys Leu Leu Asn Lys Leu Asp Thr Tyr Val Arg Asn Cys Gly Lys
            340                 345                 350
Tyr Asn Tyr Tyr Leu Gln Val Gly Glu Ile Ala Thr Ser Asp Phe Ile
            355                 360                 365
Ala Arg Asn Arg Gln Asn Glu Ala Phe Leu Arg Asn Ile Ile Gly Val
    370                 375                 380
Ser Ser Val Ala Tyr Phe Ser Leu Arg Asn Ile Leu Glu Thr Glu Asn
385                 390                 395                 400
Glu Asn Gly Ile Thr Gly Arg Met Arg Gly Lys Thr Val Lys Asn Asn
                405                 410                 415
Lys Gly Glu Glu Lys Tyr Val Ser Gly Glu Val Asp Lys Ile Tyr Asn
            420                 425                 430
Glu Asn Lys Gln Asn Glu Val Lys Glu Asn Leu Lys Met Phe Tyr Ser
            435                 440                 445
Tyr Asp Phe Asn Met Asp Asn Lys Asn Glu Ile Glu Asp Phe Phe Ala
    450                 455                 460
Asn Ile Asp Glu Ala Ile Ser Ser Ile Arg His Gly Ile Val His Phe
465                 470                 475                 480
Asn Leu Glu Leu Glu Gly Lys Asp Ile Phe Ala Phe Lys Asn Ile Ala
                485                 490                 495
Pro Ser Glu Ile Ser Lys Lys Met Phe Gln Asn Glu Ile Asn Glu Lys
            500                 505                 510
Lys Leu Lys Leu Lys Ile Phe Lys Gln Leu Asn Ser Ala Asn Val Phe
            515                 520                 525
Asn Tyr Tyr Glu Lys Asp Val Ile Ile Lys Tyr Leu Lys Asn Thr Lys
    530                 535                 540
```

Phe Asn Phe Val Asn Lys Asn Ile Pro Phe Val Pro Ser Phe Thr Lys
545                 550                 555                 560

Leu Tyr Asn Lys Ile Glu Asp Leu Arg Asn Thr Leu Lys Phe Phe Trp
        565                 570                 575

Ser Val Pro Lys Asp Lys Glu Glu Lys Asp Ala Gln Ile Tyr Leu Leu
            580                 585                 590

Lys Asn Ile Tyr Tyr Gly Glu Phe Leu Asn Lys Phe Val Lys Asn Ser
                595                 600                 605

Lys Val Phe Phe Lys Ile Thr Asn Glu Val Ile Lys Ile Asn Lys Gln
            610                 615                 620

Arg Asn Gln Lys Thr Gly His Tyr Lys Tyr Gln Lys Phe Glu Asn Ile
625                 630                 635                 640

Glu Lys Thr Val Pro Val Glu Tyr Leu Ala Ile Ile Gln Ser Arg Glu
                645                 650                 655

Met Ile Asn Asn Gln Asp Lys Glu Lys Asn Thr Tyr Ile Asp Phe
            660                 665                 670

Ile Gln Gln Ile Phe Leu Lys Gly Phe Ile Asp Tyr Leu Asn Lys Asn
                675                 680                 685

Asn Leu Lys Tyr Ile Glu Ser Asn Asn Asn Asp Asn Asn Asp Ile
    690                 695                 700

Phe Ser Lys Ile Lys Ile Lys Asp Asn Lys Glu Lys Tyr Asp Lys
705                 710                 715                 720

Ile Leu Lys Asn Tyr Glu Lys His Asn Arg Asn Lys Glu Ile Pro His
                725                 730                 735

Glu Ile Asn Glu Phe Val Arg Glu Ile Lys Leu Gly Lys Ile Leu Lys
            740                 745                 750

Tyr Thr Glu Asn Leu Asn Met Phe Tyr Leu Ile Leu Lys Leu Leu Asn
                755                 760                 765

His Lys Glu Leu Thr Asn Leu Lys Gly Ser Leu Glu Lys Tyr Gln Ser
    770                 775                 780

Ala Asn Lys Glu Glu Thr Phe Ser Asp Glu Leu Glu Leu Ile Asn Leu
785                 790                 795                 800

Leu Asn Leu Asp Asn Asn Arg Val Thr Glu Asp Phe Glu Leu Glu Ala
            805                 810                 815

Asn Glu Ile Gly Lys Phe Leu Asp Phe Asn Glu Asn Lys Ile Lys Asp
        820                 825                 830

Arg Lys Glu Leu Lys Lys Phe Asp Thr Asn Lys Ile Tyr Phe Asp Gly
        835                 840                 845

Glu Asn Ile Ile Lys His Arg Ala Phe Tyr Asn Ile Lys Lys Tyr Gly
    850                 855                 860

Met Leu Asn Leu Leu Glu Lys Ile Ala Asp Lys Ala Lys Tyr Lys Ile
865                 870                 875                 880

Ser Leu Lys Glu Leu Lys Glu Tyr Ser Asn Lys Lys Asn Glu Ile Glu
            885                 890                 895

Lys Asn Tyr Thr Met Gln Gln Asn Leu His Arg Lys Tyr Ala Arg Pro
        900                 905                 910

Lys Lys Asp Glu Lys Phe Asn Asp Glu Asp Tyr Lys Glu Tyr Glu Lys
            915                 920                 925

Ala Ile Gly Asn Ile Gln Lys Tyr Thr His Leu Lys Asn Lys Val Glu
        930                 935                 940

Phe Asn Glu Leu Asn Leu Leu Gln Gly Leu Leu Leu Lys Ile Leu His
945                 950                 955                 960

```
Arg Leu Val Gly Tyr Thr Ser Ile Trp Glu Arg Asp Leu Arg Phe Arg
                965                 970                 975

Leu Lys Gly Glu Phe Pro Glu Asn His Tyr Ile Glu Glu Ile Phe Asn
            980                 985                 990

Phe Asp Asn Ser Lys Asn Val Lys Tyr Lys Ser Gly Gln Ile Val Glu
        995                 1000                1005

Lys Tyr Ile Asn Phe Tyr Lys Glu Leu Tyr Lys Asp Asn Val Glu
    1010                1015                1020

Lys Arg Ser Ile Tyr Ser Asp Lys Lys Val Lys Lys Leu Lys Gln
    1025                1030                1035

Glu Lys Lys Asp Leu Tyr Ile Arg Asn Tyr Ile Ala His Phe Asn
    1040                1045                1050

Tyr Ile Pro His Ala Glu Ile Ser Leu Leu Glu Val Leu Glu Asn
    1055                1060                1065

Leu Arg Lys Leu Leu Ser Tyr Asp Arg Lys Leu Lys Asn Ala Ile
    1070                1075                1080

Met Lys Ser Ile Val Asp Ile Leu Lys Glu Tyr Gly Phe Val Ala
    1085                1090                1095

Thr Phe Lys Ile Gly Ala Asp Lys Lys Ile Glu Ile Gln Thr Leu
    1100                1105                1110

Glu Ser Glu Lys Ile Val His Leu Lys Asn Leu Lys Lys Lys
    1115                1120                1125

Leu Met Thr Asp Arg Asn Ser Glu Glu Leu Cys Glu Leu Val Lys
    1130                1135                1140

Val Met Phe Glu Tyr Lys Ala Leu Glu Gly Asp Pro Asn Ser Ser
    1145                1150                1155

Ser Val Asp Lys Leu Ala Ala Ala Leu Glu His His His His His
    1160                1165                1170

His
```

```
<210> SEQ ID NO 11
<211> LENGTH: 4680
<212> TYPE: DNA
<213> ORGANISM: Artificial Sequence
<220> FEATURE:
<223> OTHER INFORMATION: Synthetic

<400> SEQUENCE: 11
```

| | | |
|---|---|---|
| atgaaaatcg aagaaggtaa actggtaatc tggattaacg gcgataaagg ctataacggt | 60 |
| ctcgctgaag tcggtaagaa attcgagaaa gataccggaa ttaaagtcac cgttgagcat | 120 |
| ccggataaac tggaagagaa attcccacag gttgcggcaa ctggcgatgg ccctgacatt | 180 |
| atcttctggg cacacgaccg ctttggtggc tacgctcaat ctggcctgtt ggctgaaatc | 240 |
| accccggaca aagcgttcca ggacaagctg tatccgttta cctgggatgc cgtacgttac | 300 |
| aacggcaagc tgattgctta cccgatcgct gttgaagcgt tatcgctgat ttataacaaa | 360 |
| gatctgctgc cgaacccgcc aaaaacctgg gaagagatcc cggcgctgga taagaactg | 420 |
| aaagcgaaag gtaagagcgc gctgatgttc aacctgcaag aaccgtactt cacctggccg | 480 |
| ctgattgctg ctgacggggg ttatgcgttc aagtatgaaa acggcaagta cgacattaaa | 540 |
| gacgtgggcg tggataacgc tggcgcgaaa gcgggtctga ccttcctggt tgacctgatt | 600 |
| aaaaacaaac acatgaatgc agacaccgat tactccatcg cagaagctgc ctttaataaa | 660 |
| ggcgaaacag cgatgaccat caacggcccg tgggcatggt ccaacatcga caccagcaaa | 720 |
| gtgaattatg gtgtaacggt actgccgacc ttcaagggtc aaccatccaa accgttcgtt | 780 |

```
ggcgtgctga gcgcaggtat taacgccgcc agtccgaaca aagagctggc aaaagagttc      840
ctcgaaaact atctgctgac tgatgaaggt ctggaagcgg ttaataaaga caaaccgctg      900
ggtgccgtag cgctgaagtc ttacgaggaa gagttggtga agatccgcg tattgccgcc       960
actatggaaa acgcccagaa aggtgaaatc atgccgaaca tcccgcagat gtccgctttc     1020
tggtatgccg tgcgtactgc ggtgatcaac gccgccagcg tcgtcagac tgtcgatgaa      1080
gccctgaaag acgcgcagac taattcgagc tcgaacaaca caacaataa caataacaac      1140
aacctcggga tcgagggaag gaaagtgacc aaagtggatg gcatcagcca caaaaatac     1200
atcgaagaag gcaaactggt taaaagcacc agcgaagaaa atcgtaccag cgaacgtctg     1260
agcgaactgc tgagcattcg tctggatatc tatatcaaaa atccggataa tgccagcgag    1320
gaagaaaacc gtattcgtcg tgaaaacctg aaaaagttct tcagcaataa agtgctgcac     1380
ctgaaagata gcgttctgta tctgaaaaac cgcaaagaaa aaatgccgt gcaggacaaa      1440
aactatagcg aagaggatat cagcgagtat gacctgaaga caaaaatag ctttagcgtg      1500
ctgaaaaaaa tcctgctgaa tgaagatgtg aatagcgagg aactggaaat ctttcgtaaa     1560
gatgttgaag ccaagctgaa caaaatcaac agcctgaaat atagctttga agaaaacaag    1620
gccaactatc agaaaatcaa cgagaacaac gtggaaaaag ttggtggtaa aagcaaacgc     1680
aacatcatct atgattatta tcgcgaaagc gcgaaacgca acgattatat caataatgtg     1740
caagaggcct tcgacaaact gtacaaaaaa gaggacatcg aaaaactgtt ttttctgatc    1800
gagaacagca gaagcacga gaaatacaaa atccgcgagt actaccataa aatcatcggt     1860
cgcaaaaacg ataaagagaa cttcgccaaa atcatctacg aagaaattca gaacgtgaac    1920
aacatcaaag aactgatcga aaaaattccg gacatgagcg agctgaagaa aagccaggtg     1980
ttctataaat actacctgga caaagaggaa ctgaacgaca aaaacatcaa atatgccttt     2040
tgccacttcg tcgaaattga atgagccag ctgcttaaaa actacgtgta taaacgcctg      2100
agcaacatca gcaacgataa aatcaaacgt atctttgaat atcagaatct gaagaaactg    2160
attgaaaaca aactgctgaa caagctggat acctatgttc gtaattgcgg caaatacaac    2220
tactatctgc aggttggtga aattgcaacc agcgatttta ttgcacgtaa tcgtcagaat    2280
gaagcctttc tgcgtaacat tattggtgtt agcagcgttg catatttag cctgcgtaat     2340
attctggaaa ccgaaaacga aatggtatt accggtcgta tgcgtggtaa aaccgttaaa     2400
aacaataaag gcgaagagaa gtatgtgagc ggtgaagtgg ataaaatcta taacgaaaac    2460
aagcagaaca aagtgaaaga aatctgaaa atgttttaca gctacgactt caacatggac     2520
aacaaaaacg agatcgaaga tttcttcgcc aacattgatg aagccattag cagtattcgt    2580
catggcattg tgcactttaa tctggaactt gaaggcaaag acatcttcgc gtttaaaaac    2640
attgcaccga gcgagatcag caaaaaaatg tttcagaacg agattaacga aaaaaaactg    2700
aaactgaaaa tcttcaaaca gctgaatagc gccaacgtgt tcaactatta tgagaaagac    2760
gtgatcatca aataccttaa aaacaccaaa ttcaacttcg tgaataaaaa catcccgttt    2820
gttccgagct tcaccaaact gtataacaaa attgaagatc tgcgcaatac cctgaagttt    2880
ttttggagcg ttccgaaaga caagaagaa aaagacgcac agatctacct gcttaagaac    2940
atctattatg gcgaatttct gaacaaattc gtgaaaaata gcaaagtgtt cttcaaaatc    3000
accaacgagg tgatcaagat taacaaacag cgtaatcaga aaaccggtca ctacaaatac    3060
cagaagtttg agaacattga aaaaaccgtg ccggttgaat atctggcaat tattcagagc    3120
```

-continued

```
cgtgagatga ttaacaacca ggataaagaa gagaaaaaca cctacatcga tttcatccag    3180
cagatctttc tgaaaggctt tatcgattac ctgaacaaga acaacctgaa gtatatcgag    3240
tcgaacaaca ataacgacaa caacgacatc tttagcaaaa tcaaaatcaa gaaagataat    3300
aaagaaaaat acgacaagat cctgaaaaac tatgagaagc acaaccgcaa caaagaaatt    3360
ccgcatgaga tcaatgaatt tgtgcgcgaa attaaactgg gcaaaatcct gaaatacacc    3420
gagaacctga atatgttcta tctgattctg aagctgctga accataaaga gctgaccaat    3480
ctgaaaggta gcctggaaaa atatcagagc gcaaacaaag aagagacatt ttctgacgaa    3540
ctggaactga ttaatctgct gaatctggat aataaccgtg tgaccgaaga ttttgaactg    3600
gaagcaaatg aaatcggcaa attcctggat ttcaatgaga acaaaattaa ggaccggaaa    3660
gagcttaaaa agtttgatac caacaaaatc tacttcgacg gcgagaacat tatcaaacat    3720
cgtgcctttt ataacatcaa aaagtatggc atgctgaacc tgctggaaaa aattgcagat    3780
aaagccaagt acaaaattag cctgaaagaa cttaaagagt acagcaacaa aaagaacgaa    3840
atcgagaaga actataccat gcagcagaat ctgcatcgta atatgcacg tccgaaaaaa    3900 gacgagaaat tcaacgatga ggactataaa gaatacgaga aagccattgg caacatccag    3960
aaatataccc acttgaaaaa caaagtggaa tttaacgagc tgaatttact gcagggtctg    4020
ctgctgaaaa ttctgcaccg tctggttggt tataccagca tttgggaacg tgatctgcgt    4080
tttcgcctga aggtgaatt tcctgaaaac cactatatcg aggaaatttt caactttgac    4140
aacagcaaaa acgtgaaata taagagcggt cagatcgtcg aaaagtacat caacttttac    4200
aaagaacttt acaaggataa tgtggaaaaa cgcagcatct cagcgacaa gaaagtgaaa    4260 aagctgaagc aagaaaagaa agacctgtac atccgtaatt atatcgccca ctttaactat    4320
atcccgcatg cagaaattag tctgctggaa gttctggaaa atctgcgtaa actgctgtca    4380
tatgatcgca aactgaagaa cgcaatcatg aaaagcattg tggatatcct gaaagagtat    4440
ggttttgtcg ccacctttaa aatcggtgcc gataagaaaa ttgagattca gaccctggaa    4500
agcgagaaaa ttgtgcatct taagaacctt aaaaagaaaa aactgatgac cgatcgcaac    4560
agcgaagagt tatgtgaact ggtgaaagtg atgttcgaat acaaagcact ggaagatccg    4620
aattcgagct ccgtcgacaa gcttgcggcc gcactcgagc accaccacca ccaccactga   4680
```

<210> SEQ ID NO 12
<211> LENGTH: 1559
<212> TYPE: PRT
<213> ORGANISM: Artificial Sequence
<220> FEATURE:
<223> OTHER INFORMATION: Synthetic

<400> SEQUENCE: 12

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95
```

```
Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
            290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
            370                 375                 380

Glu Gly Arg Lys Val Thr Lys Val Asp Gly Ile Ser His Lys Lys Tyr
385                 390                 395                 400

Ile Glu Glu Gly Lys Leu Val Lys Ser Thr Ser Glu Glu Asn Arg Thr
                405                 410                 415

Ser Glu Arg Leu Ser Glu Leu Leu Ser Ile Arg Leu Asp Ile Tyr Ile
            420                 425                 430

Lys Asn Pro Asp Asn Ala Ser Glu Glu Glu Asn Arg Ile Arg Arg Glu
            435                 440                 445

Asn Leu Lys Lys Phe Phe Ser Asn Lys Val Leu His Leu Lys Asp Ser
            450                 455                 460

Val Leu Tyr Leu Lys Asn Arg Lys Glu Lys Asn Ala Val Gln Asp Lys
465                 470                 475                 480

Asn Tyr Ser Glu Glu Asp Ile Ser Glu Tyr Asp Leu Lys Asn Lys Asn
                485                 490                 495

Ser Phe Ser Val Leu Lys Lys Ile Leu Leu Asn Glu Asp Val Asn Ser
            500                 505                 510
```

```
Glu Glu Leu Glu Ile Phe Arg Lys Asp Val Glu Ala Lys Leu Asn Lys
            515                 520                 525

Ile Asn Ser Leu Lys Tyr Ser Phe Glu Asn Lys Ala Asn Tyr Gln
    530                 535                 540

Lys Ile Asn Glu Asn Asn Val Glu Lys Val Gly Gly Lys Ser Lys Arg
545                 550                 555                 560

Asn Ile Ile Tyr Asp Tyr Tyr Arg Glu Ser Ala Lys Arg Asn Asp Tyr
                565                 570                 575

Ile Asn Asn Val Gln Glu Ala Phe Asp Lys Leu Tyr Lys Lys Glu Asp
            580                 585                 590

Ile Glu Lys Leu Phe Phe Leu Ile Glu Asn Ser Lys Lys His Glu Lys
            595                 600                 605

Tyr Lys Ile Arg Glu Tyr Tyr His Lys Ile Ile Gly Arg Lys Asn Asp
    610                 615                 620

Lys Glu Asn Phe Ala Lys Ile Ile Tyr Glu Glu Ile Gln Asn Val Asn
625                 630                 635                 640

Asn Ile Lys Glu Leu Ile Glu Lys Ile Pro Asp Met Ser Glu Leu Lys
                645                 650                 655

Lys Ser Gln Val Phe Tyr Lys Tyr Tyr Leu Asp Lys Glu Glu Leu Asn
            660                 665                 670

Asp Lys Asn Ile Lys Tyr Ala Phe Cys His Phe Val Glu Ile Glu Met
        675                 680                 685

Ser Gln Leu Leu Lys Asn Tyr Val Tyr Lys Arg Leu Ser Asn Ile Ser
    690                 695                 700

Asn Asp Lys Ile Lys Arg Ile Phe Glu Tyr Gln Asn Leu Lys Lys Leu
705                 710                 715                 720

Ile Glu Asn Lys Leu Leu Asn Lys Leu Asp Thr Tyr Val Arg Asn Cys
                725                 730                 735

Gly Lys Tyr Asn Tyr Tyr Leu Gln Val Gly Glu Ile Ala Thr Ser Asp
            740                 745                 750

Phe Ile Ala Arg Asn Arg Gln Asn Glu Ala Phe Leu Arg Asn Ile Ile
        755                 760                 765

Gly Val Ser Ser Val Ala Tyr Phe Ser Leu Arg Asn Ile Leu Glu Thr
    770                 775                 780

Glu Asn Glu Asn Gly Ile Thr Gly Arg Met Arg Gly Lys Thr Val Lys
785                 790                 795                 800

Asn Asn Lys Gly Glu Glu Lys Tyr Val Ser Gly Glu Val Asp Lys Ile
                805                 810                 815

Tyr Asn Glu Asn Lys Gln Asn Glu Val Lys Glu Asn Leu Lys Met Phe
            820                 825                 830

Tyr Ser Tyr Asp Phe Asn Met Asp Asn Lys Asn Glu Ile Glu Asp Phe
        835                 840                 845

Phe Ala Asn Ile Asp Glu Ala Ile Ser Ser Ile Arg His Gly Ile Val
    850                 855                 860

His Phe Asn Leu Glu Leu Glu Gly Lys Asp Ile Phe Ala Phe Lys Asn
865                 870                 875                 880

Ile Ala Pro Ser Glu Ile Ser Lys Lys Met Phe Gln Asn Glu Ile Asn
                885                 890                 895

Glu Lys Lys Leu Lys Leu Lys Ile Phe Lys Gln Leu Asn Ser Ala Asn
            900                 905                 910

Val Phe Asn Tyr Tyr Glu Lys Asp Val Ile Ile Lys Tyr Leu Lys Asn
        915                 920                 925

Thr Lys Phe Asn Phe Val Asn Lys Asn Ile Pro Phe Val Pro Ser Phe
```

```
                930             935             940
Thr Lys Leu Tyr Asn Lys Ile Glu Asp Leu Arg Asn Thr Leu Lys Phe
945                 950             955                 960

Phe Trp Ser Val Pro Lys Asp Lys Glu Glu Lys Asp Ala Gln Ile Tyr
                965             970                 975

Leu Leu Lys Asn Ile Tyr Tyr Gly Glu Phe Leu Asn Lys Phe Val Lys
            980             985                 990

Asn Ser Lys Val Phe Phe Lys Ile  Thr Asn Glu Val Ile  Lys Ile Asn
        995             1000            1005

Lys Gln  Arg Asn Gln Lys Thr  Gly His Tyr Lys Tyr  Gln Lys Phe
    1010            1015            1020

Glu Asn  Ile Glu Lys Thr Val  Pro Val Glu Tyr Leu  Ala Ile Ile
    1025            1030            1035

Gln Ser  Arg Glu Met Ile Asn  Asn Gln Asp Lys Glu  Glu Lys Asn
    1040            1045            1050

Thr Tyr  Ile Asp Phe Ile Gln  Gln Ile Phe Leu Lys  Gly Phe Ile
    1055            1060            1065

Asp Tyr  Leu Asn Lys Asn Asn  Leu Lys Tyr Ile Glu  Ser Asn Asn
    1070            1075            1080

Asn Asn  Asp Asn Asn Asp Ile  Phe Ser Lys Ile Lys  Ile Lys Lys
    1085            1090            1095

Asp Asn  Lys Glu Lys Tyr Asp  Lys Ile Leu Lys Asn  Tyr Glu Lys
    1100            1105            1110

His Asn  Arg Asn Lys Glu Ile  Pro His Glu Ile Asn  Glu Phe Val
    1115            1120            1125

Arg Glu  Ile Lys Leu Gly Lys  Ile Leu Lys Tyr Thr  Glu Asn Leu
    1130            1135            1140

Asn Met  Phe Tyr Leu Ile Leu  Lys Leu Leu Asn His  Lys Glu Leu
    1145            1150            1155

Thr Asn  Leu Lys Gly Ser Leu  Glu Lys Tyr Gln Ser  Ala Asn Lys
    1160            1165            1170

Glu Glu  Thr Phe Ser Asp Glu  Leu Glu Leu Ile Asn  Leu Leu Asn
    1175            1180            1185

Leu Asp  Asn Asn Arg Val Thr  Glu Asp Phe Glu Leu  Glu Ala Asn
    1190            1195            1200

Glu Ile  Gly Lys Phe Leu Asp  Phe Asn Glu Asn Lys  Ile Lys Asp
    1205            1210            1215

Arg Lys  Glu Leu Lys Lys Phe  Asp Thr Asn Lys Ile  Tyr Phe Asp
    1220            1225            1230

Gly Glu  Asn Ile Ile Lys His  Arg Ala Phe Tyr Asn  Ile Lys Lys
    1235            1240            1245

Tyr Gly  Met Leu Asn Leu Leu  Glu Lys Ile Ala Asp  Lys Ala Lys
    1250            1255            1260

Tyr Lys  Ile Ser Leu Lys Glu  Leu Lys Glu Tyr Ser  Asn Lys Lys
    1265            1270            1275

Asn Glu  Ile Glu Lys Asn Tyr  Thr Met Gln Gln Asn  Leu His Arg
    1280            1285            1290

Lys Tyr  Ala Arg Pro Lys Lys  Asp Glu Lys Phe Asn  Asp Glu Asp
    1295            1300            1305

Tyr Lys  Glu Tyr Glu Lys Ala  Ile Gly Asn Ile Gln  Lys Tyr Thr
    1310            1315            1320

His Leu  Lys Asn Lys Val Glu  Phe Asn Glu Leu Asn  Leu Leu Gln
    1325            1330            1335
```

```
Gly Leu Leu Leu Lys Ile Leu His Arg Leu Val Gly Tyr Thr Ser
    1340                1345                1350

Ile Trp Glu Arg Asp Leu Arg Phe Arg Leu Lys Gly Glu Phe Pro
    1355                1360                1365

Glu Asn His Tyr Ile Glu Glu Ile Phe Asn Phe Asp Asn Ser Lys
    1370                1375                1380

Asn Val Lys Tyr Lys Ser Gly Gln Ile Val Glu Lys Tyr Ile Asn
    1385                1390                1395

Phe Tyr Lys Glu Leu Tyr Lys Asp Asn Val Glu Lys Arg Ser Ile
    1400                1405                1410

Tyr Ser Asp Lys Lys Val Lys Lys Leu Lys Gln Glu Lys Lys Asp
    1415                1420                1425

Leu Tyr Ile Arg Asn Tyr Ile Ala His Phe Asn Tyr Ile Pro His
    1430                1435                1440

Ala Glu Ile Ser Leu Leu Glu Val Leu Glu Asn Leu Arg Lys Leu
    1445                1450                1455

Leu Ser Tyr Asp Arg Lys Leu Lys Asn Ala Ile Met Lys Ser Ile
    1460                1465                1470

Val Asp Ile Leu Lys Glu Tyr Gly Phe Val Ala Thr Phe Lys Ile
    1475                1480                1485

Gly Ala Asp Lys Lys Ile Glu Ile Gln Thr Leu Glu Ser Glu Lys
    1490                1495                1500

Ile Val His Leu Lys Asn Leu Lys Lys Lys Lys Leu Met Thr Asp
    1505                1510                1515

Arg Asn Ser Glu Glu Leu Cys Glu Leu Val Lys Val Met Phe Glu
    1520                1525                1530

Tyr Lys Ala Leu Glu Asp Pro Asn Ser Ser Ser Val Asp Lys Leu
    1535                1540                1545

Ala Ala Ala Leu Glu His His His His His His
    1550                1555

<210> SEQ ID NO 13
<211> LENGTH: 3525
<212> TYPE: DNA
<213> ORGANISM: Artificial Sequence
<220> FEATURE:
<223> OTHER INFORMATION: Synthetic

<400> SEQUENCE: 13
atgaaagtga ccaaagtgga tggcatcagc cacaaaaaat acatcgaaga aggcaaactg      60
gttaaaagca ccagcgaaga aaatcgtacc agcgaacgtc tgagcgaact gctgagcatt     120
cgtctggata tctatatcaa aaatccggat aatgccagcg aggaagaaaa ccgtattcgt     180
cgtgaaaacc tgaaaaagtt cttcagcaat aaagtgctgc acctgaaaga tagcgttctg     240
tatctgaaaa accgcaaaga aaaaaatgcc gtgcaggaca aaactatag cgaagaggat     300 atcagcgagt atgacctgaa gaacaaaaat agctttagcg tgctgaaaaa aatcctgctg     360
aatgaagatg tgaatagcga ggaactggaa atctttcgta agatgttga agccaagctg     420 aacaaaatca cagcctgaa atatagctt gaagaaaaca aggccaacta tcagaaaatc     480
aacgagaaca acgtggaaaa agttggtggt aaaagcaaac gcaacatcat ctatgattat     540
tatcgcgaaa gcgcgaaacg caacgattat atcaataatg tgcaagaggc cttcgacaaa     600
ctgtacaaaa agaggacat cgaaaaactg tttttcctga tcgagaacag caagaagcac     660
gagaaataca aaatccgcga gtactaccat aaaatcatcg gtcgcaaaaa cgataaagag     720
```

```
aacttcgcca aaatcatcta cgaagaaatt cagaacgtga acaacatcaa agaactgatc    780
gaaaaaattc cggacatgag cgagctgaag aaaagccagg tgttctataa atactacctg    840
gacaaagagg aactgaacga caaaaacatc aaatatgcct tttgccactt cgtcgaaatt    900
gaaatgagcc agctgcttaa aaactacgtg tataaacgcc tgagcaacat cagcaacgat    960
aaaatcaaac gtatctttga atatcagaat ctgaagaaac tgattgaaaa caaactgctg   1020
aacaagctgg atacctatgt tcgtaattgc ggcaaataca actactatct gcaggttggt   1080
gaaattgcaa ccagcgattt tattgcacgt aatcgtcaga tgaagccctt tctgcgtaac   1140
attattggtg ttagcagcgt tgcatatttt agcctgcgta atattctgga aaccgaaaac   1200
gaaaatgata ttaccggtcg tatgcgtggt aaaaccgtta aaacaataa aggcgaagag    1260 aagtatgtga gcggtgaagt ggataaaatc tataacgaaa acaagcagaa cgaagtgaaa   1320
gaaaatctga aaatgtttta cagctacgac ttcaacatgg acaacaaaaa cgagatcgaa   1380
gatttcttcg ccaacattga tgaagccatt agcagtattc gtcatggcat tgtgcacttt   1440
aatctggaac ttgaaggcaa agacatcttc gcgtttaaaa acattgcacc gagcgagatc   1500
agcaaaaaaa tgtttcagaa cgagattaac gaaaaaaaac tgaaactgaa atcttcaaa    1560 cagctgaata gcgccaacgt gttcaactat tatgagaaag acgtgatcat caaataccct   1620
aaaaacacca aattcaactt cgtgaataaa aacatcccgt tgttccgag cttcaccaaa    1680 ctgtataaca aaattgaaga tctgcgcaat accctgaagt tttttttggag cgttccgaaa   1740 gacaaagaag aaaaagacgc acagatctac ctgcttaaga acatctatta tggcgaattt   1800
ctgaacaaat tcgtgaaaaa tagcaaagtg ttcttcaaaa tcaccaacga ggtgatcaag   1860
attaacaaac agcgtaatca gaaaaccggt cactacaaat accagaagtt tgagaacatt   1920
gaaaaaaccg tgccggttga atatctggca attattcaga gccgtgagat gattaacaac   1980
caggataaag aagagaaaaa cacctacatc gatttcatcc agcagatctt tctgaaaggc   2040
tttatcgatt acctgaacaa gaacaacctg aagtatatcg agtcgaacaa caataacgac   2100
aacaacgaca tctttagcaa aatcaaaatc aagaaagata taaagaaaa atacgacaag    2160 atcctgaaaa actatgagaa gcacaaccgc aacaaagaaa ttccgcatga gatcaatgaa   2220
tttgtgcgcg aaattaaact gggcaaaatc ctgaaataca ccgagaacct gaatatgttc   2280
tatctgattc tgaagctgct gaaccataaa gagctgacca atctgaaagg tagcctggaa   2340
aaatatcaga gcgcaaacaa agaagagaca ttttctgacg aactggaact gattaatctg   2400
ctgaatctgg ataataaccg tgtgaccgaa gattttgaac tggaagcaaa tgaaatcggc   2460
aaattcctgg atttcaatga gaacaaaatt aaggaccgga aagagcttaa aaagtttgat   2520
accaacaaaa tctacttcga cggcgagaac attatcaaac atcgtgcctt ttataacatc   2580
aaaaagtatg gcatgctgaa cctgctggaa aaattgcag ataaagccaa gtacaaaatt    2640
agcctgaaag aacttaaaga gtacagcaac aaaaagaacg aaatcgagaa gaactatacc   2700
atgcagcaga atctgcatcg taaatatgca cgtccgaaaa aagacgagaa attcaacgat   2760
gaggactata aagaatacga gaaagccatt ggcaacatcc agaaatatac ccacttgaaa   2820
aacaaagtgg aatttaacga gctgaattta ctgcagggtc tgctgctgaa aattctgcac   2880
cgtctggttg gttataccag catttgggaa cgtgatctgc gttttcgcct gaaaggtgaa   2940
tttcctgaaa accactatat cgaggaaatt ttcaactttg acaacagcaa aaacgtgaaa   3000
tataagagcg gtcagatcgt cgaaaagtac atcaactttt acaagaaact ttacaaggat   3060
```

-continued

```
aatgtggaaa aacgcagcat ctacagcgac aagaaagtga aaaagctgaa gcaagaaaag      3120
aaagacctgt acatccgtaa ttatatcgcc cactttaact atatcccgca tgcagaaatt      3180
agtctgctgg aagttctgga aaatctgcgt aaactgctgt catatgatcg caaactgaag      3240
aacgcaatca tgaaaagcat tgtggatatc ctgaaagagt atggttttgt cgccaccttt      3300
aaaatcggtg ccgataagaa aattgagatt cagaccctgg aaagcgagaa aattgtgcat      3360
cttaagaacc ttaaaaagaa aaaactgatg accgatcgca acagcgaaga gttatgtgaa      3420
ctggtgaaag tgatgttcga atacaaagca ctggaagggg atccgaattc gagctccgtc      3480
gacaagcttg cggccgcact cgagcaccac caccaccacc actga                     3525
```

<210> SEQ ID NO 14
<211> LENGTH: 1174
<212> TYPE: PRT
<213> ORGANISM: Artificial Sequence
<220> FEATURE:
<223> OTHER INFORMATION: Synthetic

<400> SEQUENCE: 14

```
Met Lys Val Thr Lys Val Asp Gly Ile Ser His Lys Lys Tyr Ile Glu
1               5                   10                  15

Glu Gly Lys Leu Val Lys Ser Thr Ser Glu Glu Asn Arg Thr Ser Glu
            20                  25                  30

Arg Leu Ser Glu Leu Leu Ser Ile Arg Leu Asp Ile Tyr Ile Lys Asn
        35                  40                  45

Pro Asp Asn Ala Ser Glu Glu Asn Arg Ile Arg Arg Glu Asn Leu
    50                  55                  60

Lys Lys Phe Phe Ser Asn Lys Val Leu His Leu Lys Asp Ser Val Leu
65                  70                  75                  80

Tyr Leu Lys Asn Arg Lys Glu Lys Asn Ala Val Gln Asp Lys Asn Tyr
                85                  90                  95

Ser Glu Glu Asp Ile Ser Glu Tyr Asp Leu Lys Asn Lys Asn Ser Phe
            100                 105                 110

Ser Val Leu Lys Lys Ile Leu Leu Asn Glu Asp Val Asn Ser Glu Glu
        115                 120                 125

Leu Glu Ile Phe Arg Lys Asp Val Glu Ala Lys Leu Asn Lys Ile Asn
    130                 135                 140

Ser Leu Lys Tyr Ser Phe Glu Glu Asn Lys Ala Asn Tyr Gln Lys Ile
145                 150                 155                 160

Asn Glu Asn Asn Val Glu Lys Val Gly Gly Lys Ser Lys Arg Asn Ile
                165                 170                 175

Ile Tyr Asp Tyr Tyr Arg Glu Ser Ala Lys Arg Asn Asp Tyr Ile Asn
            180                 185                 190

Asn Val Gln Glu Ala Phe Asp Lys Leu Tyr Lys Lys Glu Asp Ile Glu
        195                 200                 205

Lys Leu Phe Phe Leu Ile Glu Asn Ser Lys Lys His Glu Lys Tyr Lys
    210                 215                 220

Ile Arg Glu Tyr Tyr His Lys Ile Ile Gly Arg Lys Asn Asp Lys Glu
225                 230                 235                 240

Asn Phe Ala Lys Ile Ile Tyr Glu Glu Ile Gln Asn Val Asn Asn Ile
                245                 250                 255

Lys Glu Leu Ile Glu Lys Ile Pro Asp Met Ser Glu Leu Lys Lys Ser
            260                 265                 270

Gln Val Phe Tyr Lys Tyr Tyr Leu Asp Lys Glu Glu Leu Asn Asp Lys
        275                 280                 285
```

```
Asn Ile Lys Tyr Ala Phe Cys His Phe Val Glu Ile Glu Met Ser Gln
    290             295                 300

Leu Leu Lys Asn Tyr Val Tyr Lys Arg Leu Ser Asn Ile Ser Asn Asp
305                 310                 315                 320

Lys Ile Lys Arg Ile Phe Glu Tyr Gln Asn Leu Lys Lys Leu Ile Glu
                325                 330                 335

Asn Lys Leu Leu Asn Lys Leu Asp Thr Tyr Val Arg Asn Cys Gly Lys
            340                 345                 350

Tyr Asn Tyr Tyr Leu Gln Val Gly Glu Ile Ala Thr Ser Asp Phe Ile
        355                 360                 365

Ala Arg Asn Arg Gln Asn Glu Ala Phe Leu Arg Asn Ile Ile Gly Val
370                 375                 380

Ser Ser Val Ala Tyr Phe Ser Leu Arg Asn Ile Leu Glu Thr Glu Asn
385                 390                 395                 400

Glu Asn Asp Ile Thr Gly Arg Met Arg Gly Lys Thr Val Lys Asn Asn
                405                 410                 415

Lys Gly Glu Glu Lys Tyr Val Ser Gly Glu Val Asp Lys Ile Tyr Asn
            420                 425                 430

Glu Asn Lys Gln Asn Glu Val Lys Glu Asn Leu Lys Met Phe Tyr Ser
        435                 440                 445

Tyr Asp Phe Asn Met Asp Asn Lys Asn Glu Ile Glu Asp Phe Phe Ala
450                 455                 460

Asn Ile Asp Glu Ala Ile Ser Ser Ile Arg His Gly Ile Val His Phe
465                 470                 475                 480

Asn Leu Glu Leu Glu Gly Lys Asp Ile Phe Ala Phe Lys Asn Ile Ala
                485                 490                 495

Pro Ser Glu Ile Ser Lys Lys Met Phe Gln Asn Glu Ile Asn Glu Lys
            500                 505                 510

Lys Leu Lys Leu Lys Ile Phe Lys Gln Leu Asn Ser Ala Asn Val Phe
        515                 520                 525

Asn Tyr Tyr Glu Lys Asp Val Ile Ile Lys Tyr Leu Lys Asn Thr Lys
530                 535                 540

Phe Asn Phe Val Asn Lys Asn Ile Pro Phe Val Pro Ser Phe Thr Lys
545                 550                 555                 560

Leu Tyr Asn Lys Ile Glu Asp Leu Arg Asn Thr Leu Lys Phe Phe Trp
                565                 570                 575

Ser Val Pro Lys Asp Lys Glu Glu Lys Asp Ala Gln Ile Tyr Leu Leu
            580                 585                 590

Lys Asn Ile Tyr Tyr Gly Glu Phe Leu Asn Lys Phe Val Lys Asn Ser
        595                 600                 605

Lys Val Phe Phe Lys Ile Thr Asn Glu Val Ile Lys Ile Asn Lys Gln
610                 615                 620

Arg Asn Gln Lys Thr Gly His Tyr Lys Tyr Gln Lys Phe Glu Asn Ile
625                 630                 635                 640

Glu Lys Thr Val Pro Val Glu Tyr Leu Ala Ile Ile Gln Ser Arg Glu
                645                 650                 655

Met Ile Asn Asn Gln Asp Lys Glu Glu Lys Asn Thr Tyr Ile Asp Phe
            660                 665                 670

Ile Gln Gln Ile Phe Leu Lys Gly Phe Ile Asp Tyr Leu Asn Lys Asn
        675                 680                 685

Asn Leu Lys Tyr Ile Glu Ser Asn Asn Asn Asn Asp Asn Asn Asp Ile
690                 695                 700
```

```
Phe Ser Lys Ile Lys Ile Lys Asp Asn Lys Glu Lys Tyr Asp Lys
705                 710                 715                 720

Ile Leu Lys Asn Tyr Glu Lys His Asn Arg Asn Lys Glu Ile Pro His
            725                 730                 735

Glu Ile Asn Glu Phe Val Arg Glu Ile Lys Leu Gly Lys Ile Leu Lys
                740                 745                 750

Tyr Thr Glu Asn Leu Asn Met Phe Tyr Leu Ile Leu Lys Leu Leu Asn
            755                 760                 765

His Lys Glu Leu Thr Asn Leu Lys Gly Ser Leu Glu Lys Tyr Gln Ser
        770                 775                 780

Ala Asn Lys Glu Glu Thr Phe Ser Asp Glu Leu Glu Leu Ile Asn Leu
785                 790                 795                 800

Leu Asn Leu Asp Asn Asn Arg Val Thr Glu Asp Phe Glu Leu Glu Ala
                805                 810                 815

Asn Glu Ile Gly Lys Phe Leu Asp Phe Asn Glu Asn Lys Ile Lys Asp
                820                 825                 830

Arg Lys Glu Leu Lys Lys Phe Asp Thr Asn Lys Ile Tyr Phe Asp Gly
            835                 840                 845

Glu Asn Ile Ile Lys His Arg Ala Phe Tyr Asn Ile Lys Lys Tyr Gly
        850                 855                 860

Met Leu Asn Leu Leu Glu Lys Ile Ala Asp Lys Ala Lys Tyr Lys Ile
865                 870                 875                 880

Ser Leu Lys Glu Leu Lys Glu Tyr Ser Asn Lys Lys Asn Glu Ile Glu
                885                 890                 895

Lys Asn Tyr Thr Met Gln Gln Asn Leu His Arg Lys Tyr Ala Arg Pro
            900                 905                 910

Lys Lys Asp Glu Lys Phe Asn Asp Glu Asp Tyr Lys Glu Tyr Glu Lys
        915                 920                 925

Ala Ile Gly Asn Ile Gln Lys Tyr Thr His Leu Lys Asn Lys Val Glu
    930                 935                 940

Phe Asn Glu Leu Asn Leu Leu Gln Gly Leu Leu Leu Lys Ile Leu His
945                 950                 955                 960

Arg Leu Val Gly Tyr Thr Ser Ile Trp Glu Arg Asp Leu Arg Phe Arg
                965                 970                 975

Leu Lys Gly Glu Phe Pro Glu Asn His Tyr Ile Glu Glu Ile Phe Asn
            980                 985                 990

Phe Asp Asn Ser Lys Asn Val Lys Tyr Lys Ser Gly Gln Ile Val Glu
        995                 1000                1005

Lys Tyr Ile Asn Phe Tyr Lys Glu Leu Tyr Lys Asp Asn Val Glu
    1010                1015                1020

Lys Arg Ser Ile Tyr Ser Asp Lys Lys Val Lys Lys Leu Lys Gln
    1025                1030                1035

Glu Lys Lys Asp Leu Tyr Ile Arg Asn Tyr Ile Ala His Phe Asn
    1040                1045                1050

Tyr Ile Pro His Ala Glu Ile Ser Leu Leu Glu Val Leu Glu Asn
    1055                1060                1065

Leu Arg Lys Leu Leu Ser Tyr Asp Arg Lys Leu Lys Asn Ala Ile
    1070                1075                1080

Met Lys Ser Ile Val Asp Ile Leu Lys Glu Tyr Gly Phe Val Ala
    1085                1090                1095

Thr Phe Lys Ile Gly Ala Asp Lys Lys Ile Glu Ile Gln Thr Leu
    1100                1105                1110

Glu Ser Glu Lys Ile Val His Leu Lys Asn Leu Lys Lys Lys Lys
```

```
            1115                1120                1125

Leu Met Thr Asp Arg Asn Ser Glu Glu Leu Cys Glu Leu Val Lys
        1130                1135                1140

Val Met Phe Glu Tyr Lys Ala Leu Glu Gly Asp Pro Asn Ser Ser
    1145                1150                1155

Ser Val Asp Lys Leu Ala Ala Ala Leu Glu His His His His His
    1160                1165                1170

His
```

<210> SEQ ID NO 15
<211> LENGTH: 60
<212> TYPE: DNA
<213> ORGANISM: Artificial Sequence
<220> FEATURE:
<223> OTHER INFORMATION: Synthetic

<400> SEQUENCE: 15

```
gaaataattt tgtttaactt taagaaggag atataccatg aaggtgacca aagttggtgg    60
```

<210> SEQ ID NO 16
<211> LENGTH: 73
<212> TYPE: DNA
<213> ORGANISM: Artificial Sequence
<220> FEATURE:
<223> OTHER INFORMATION: Synthetic

<400> SEQUENCE: 16

```
cggccgcaag cttgtcgacg gagctcgaat tcggatcccc attttcggat ttcttctctt    60
ccattttata ctc                                                       73
```

<210> SEQ ID NO 17
<211> LENGTH: 60
<212> TYPE: DNA
<213> ORGANISM: Artificial Sequence
<220> FEATURE:
<223> OTHER INFORMATION: Synthetic

<400> SEQUENCE: 17

```
aataacaata caacaacct cgggatcgag ggaaggaagg tgaccaaagt tggtggtatc    60
```

<210> SEQ ID NO 18
<211> LENGTH: 73
<212> TYPE: DNA
<213> ORGANISM: Artificial Sequence
<220> FEATURE:
<223> OTHER INFORMATION: Synthetic

<400> SEQUENCE: 18

```
gtgcggccgc aagcttgtcg acggagctcg aattcggatc attttcggat ttcttctctt    60
ccattttata ctc                                                       73
```

<210> SEQ ID NO 19
<211> LENGTH: 60
<212> TYPE: DNA
<213> ORGANISM: Artificial Sequence
<220> FEATURE:
<223> OTHER INFORMATION: Synthetic

<400> SEQUENCE: 19

```
ataattttgt ttaactttaa gaaggagata taccatgggt aacctgtttg gtcataaacg    60
```

<210> SEQ ID NO 20

<211> LENGTH: 69
<212> TYPE: DNA
<213> ORGANISM: Artificial Sequence
<220> FEATURE:
<223> OTHER INFORMATION: Synthetic

<400> SEQUENCE: 20

```
cggccgcaag cttgtcgacg gagctcgaat tcggatcccc cagggtatca ttggtatttt      60
caatcttgg                                                              69
```

<210> SEQ ID NO 21
<211> LENGTH: 60
<212> TYPE: DNA
<213> ORGANISM: Artificial Sequence
<220> FEATURE:
<223> OTHER INFORMATION: Synthetic

<400> SEQUENCE: 21

```
taacaataac aacaacctcg ggatcgaggg aagggtaac ctgtttggtc ataaacgttg       60
```

<210> SEQ ID NO 22
<211> LENGTH: 69
<212> TYPE: DNA
<213> ORGANISM: Artificial Sequence
<220> FEATURE:
<223> OTHER INFORMATION: Synthetic

<400> SEQUENCE: 22

```
gtgcggccgc aagcttgtcg acggagctcg aattcggatc cagggtatca ttggtatttt     60
caatcttgg                                                             69
```

<210> SEQ ID NO 23
<211> LENGTH: 59
<212> TYPE: DNA
<213> ORGANISM: Artificial Sequence
<220> FEATURE:
<223> OTHER INFORMATION: Synthetic

<400> SEQUENCE: 23

```
aaataatttt gtttaactttt aagaaggaga tataccatga aagtgaccaa agtggatgg      59
```

<210> SEQ ID NO 24
<211> LENGTH: 60
<212> TYPE: DNA
<213> ORGANISM: Artificial Sequence
<220> FEATURE:
<223> OTHER INFORMATION: Synthetic

<400> SEQUENCE: 24

```
gcaagcttgt cgacggagct cgaattcgga tcccttcca gtgctttgta ttcgaacatc       60
```

<210> SEQ ID NO 25
<211> LENGTH: 60
<212> TYPE: DNA
<213> ORGANISM: Artificial Sequence
<220> FEATURE:
<223> OTHER INFORMATION: Synthetic

<400> SEQUENCE: 25

```
acaataacaa taacaacaac ctcgggatcg agggaaggaa agtgaccaaa gtggatggca      60
```

<210> SEQ ID NO 26
<211> LENGTH: 60
<212> TYPE: DNA
<213> ORGANISM: Artificial Sequence

```
<220> FEATURE:
<223> OTHER INFORMATION: Synthetic

<400> SEQUENCE: 26
caagcttgtc gacggagctc gaattcggat ccccttccag tgctttgtat tcgaacatca    60

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ggggatccga attcgagctc                                                20

<210> SEQ ID NO 28
<211> LENGTH: 37
<212> TYPE: DNA
<213> ORGANISM: Artificial Sequence
<220> FEATURE:
<223> OTHER INFORMATION: Synthetic

<400> SEQUENCE: 28
ggtatatctc cttcttaaag ttaaacaaaa ttatttc                              37

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
gatccgaatt cgagctccgt                                                20

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
ccttccctcg atcccgagg                                                 19

<210> SEQ ID NO 31
<211> LENGTH: 53
<212> TYPE: DNA
<213> ORGANISM: Artificial Sequence
<220> FEATURE:
<223> OTHER INFORMATION: Synthetic

<400> SEQUENCE: 31
gtaatattct ggaaccgaa acgaaaatg atattaccgg tcgtatgcgt ggt              53

<210> SEQ ID NO 32
<211> LENGTH: 53
<212> TYPE: DNA
<213> ORGANISM: Artificial Sequence
<220> FEATURE:
<223> OTHER INFORMATION: Synthetic

<400> SEQUENCE: 32
accacgcata cgaccggtaa tatcattttc gttttcggtt tccagaatat tac            53
```

<210> SEQ ID NO 33
<211> LENGTH: 67
<212> TYPE: RNA
<213> ORGANISM: Artificial Sequence
<220> FEATURE:
<223> OTHER INFORMATION: Synthetic

<400> SEQUENCE: 33
ggggauuuag acuaccccaa aaacgaaggg gacuaaaacu agauugcugu ucuaccaagu    60
aauccau                                                              67

<210> SEQ ID NO 34
<211> LENGTH: 59
<212> TYPE: RNA
<213> ORGANISM: Artificial Sequence
<220> FEATURE:
<223> OTHER INFORMATION: Synthetic

<400> SEQUENCE: 34
gaccacccca aaaugaagg ggacuaaaac auagauugcu guucuaccaa guaauccau     59

<210> SEQ ID NO 35
<211> LENGTH: 56
<212> TYPE: RNA
<213> ORGANISM: Artificial Sequence
<220> FEATURE:
<223> OTHER INFORMATION: Synthetic

<400> SEQUENCE: 35
ccaccccaau aucgaagggg acuaaaacua gauugcuguu cuaccaagua auccau       56

<210> SEQ ID NO 36
<211> LENGTH: 8752
<212> TYPE: DNA
<213> ORGANISM: Artificial Sequence
<220> FEATURE:
<223> OTHER INFORMATION: Synthetic

<400> SEQUENCE: 36
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggggc tccctttagg   180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta tagggatttt tgccgatttc ggcctattgg ttaaaaaatg agctgattta   420
acaaaaattt aacgcgaatt ttaacaaaat attaacgttt acaatttcag gtggcacttt   480
tcggggaaat gtgcgcggaa cccctatttg tttattttc taaatacatt caaatatgta   540
tccgctcatg aattaattct tagaaaaact catcgagcat caaatgaaac tgcaatttat   600
tcatatcagg attatcaata ccatattttt gaaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga gacgaaatac gcgatcgctg ttaaaaggac   960

```
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg caacgctac    1200 ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc    1620
agagcgcaga taccaaatac tgtccttcta gtgtagccgt agttaggcca cacttcaag    1680 aactctgtag caccgcctac atacctcgct ctgctaatcc tgttaccagt ggctgctgcc   1740
agtggcgata gtcgtgtct taccggggttg gactcaagac gatagttacc ggataaggcg    1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
```

```
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggtttttc ttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacgcggga tataacatga gctgtcttcg gtatcgtcgt    3780
atcccactac cgagatatcc gcaccaacgc gcagcccgga ctcggtaatg cgcgcattg     3840 cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacgcg cgatttgctg gtgacccaat gcgaccagat     4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgaaggtga ccaaagttgg tggtatcagc    5100
cataaaaagt ataccagcga aggtcgtctg gttaaaagcg aaagcgaaga aaatcgtacc    5160
gatgaacgtc tgagcgcact gctgaatatg cgtctggata tgtatatcaa aaatccgagc    5220
agcaccgaaa ccaaagaaaa tcagaaacgt atcggcaagc tgaaaaagtt cttcagcaac    5280
aaaatggtgt acctgaaaga taacaccctg agcctgaaaa acggcaagaa agaaaatatc    5340
gatcgcgagt atagcgaaac cgatattctg gaaagtgatg tgcgtgacaa aaaaaacttt    5400
gccgtcctga aaagatcta tctgaacgaa aatgtgaaca cgaagaact ggaagtgttt     5460 cgcaacgaca ttaaaagaa gctgaacaag atcaacagcc tgaaatatag cttcgagaaa    5520
aacaaagcca actatcagaa gatcaacgag aacaacatcg aaaagtgga aggtaaaagc    5580 aagcgcaaca tcatctatga ttattatcgt gaaagcgcca acgtgatgc ctatgttagc    5640 aatgttaaag aggccttcga caagctgtat aaagaagaag atattgccaa actggtgctg    5700
```

```
gaaattgaaa atctgaccaa gctggaaaaa tacaagatcc gcgaattcta tcacgaaatc   5760
attggtcgca aaacgataa agagaacttc gccaaaatca tctacgaaga aattcagaac    5820
gtgaataaca tgaaagaact gatcgagaaa gttccggata tgagcgaact gaaaaaaagc   5880
caggtgttct acaaatatta cctggacaaa gaggaactga acgataaaaa catcaaatac   5940
gccttttgcc acttcgtgga aatcgaaatg agccagctgc tgaaaaacta tgtgtataaa   6000
cgcctgagca catcagcaa cgataagatt aaacgcatct tcgagtacca gaacctgaag    6060
aaactgattg aaaacaaact gcttaacaaa ctggatacct atgtgcgtaa ttgcggcaaa   6120
tacaactatt atctgcagga tggtgaaatt gcgaccagcg atttattgc acgtaatcgt    6180 cagaatgaag cctttctgcg taacattatt ggtgttagca gcgttgcata ttttagcctg   6240
cgtaatatcc tggaaaccga aaacgagaat gatatcaccg tcgtatgcg tggtaaaacc    6300 gtgaaaaaca ataaggcga agagaaatat gtgagcggtg aggtggataa aatctacaac    6360
gaaaacaaaa agaacgaagt gaaagaaaac ctgaaaatgt tttacagcta cgactttaac   6420
atggacaaca agaacgagat cgaagatttt ttcgccaaca ttgatgaagc cattagcagc   6480
attcgtcatg gcattgttca ctttaatctg gaacttgagg gcaaagacat cttcgcgttt   6540
aaaaacattg caccgagcga gattagcaaa aagatgttcc agaacgaaat taacgagaaa   6600
aaactgaaac tgaagatctt tcgccagctg aatagcgcaa atgttttcg ctatcttgag    6660 aaatacaaaa tcctgaacta tctgaaacgc accgctttg aatttgtgaa caaaaacatt    6720
ccgtttgtgc cgagctttac caaactgtat agccgtattg atgatctgaa aaacagcctg   6780
ggcatttatt ggaaaacccc gaaaaccaac gatgataaca agacgaaaga aatcatcgat   6840
gcccagattt atctgcttaa gaacatctac tatggcgaat ttctgaacta ttttatgagc   6900
aacaacggca acttctttga aatcagcaaa gagattatcg agctgaataa aaacgacaaa   6960
cgcaatctga aaccggctt ctataaactg cagaagtttg aggatatcca agaaaagatc    7020
ccgaaagaat atctggcgaa tattcagagc ctgtacatga ttaatgcagg caatcaggat   7080
gaggaagaga aagataccta tatcgatttc atccagaaaa tctttctgaa aggctttatg   7140
acctatctgg ccaataatgg tcgtctgagt ctgatttata tcggtagtga tgaagaaacc   7200
aataccagcc tggcagaaaa aaaacaagag ttcgataagt tcctgaagaa gtacgaacag   7260
aacaacaaca tcaagatccc gtatgaaatc aatgaatttc tgcgcgaaat caagctgggc   7320
aacattctga aatacaccga acgcctgaat atgttctatc tgattctgaa actgctgaac   7380
cataaagagc tgacgaatct gaaaggtagc ctggaaaagt atcagagcgc aaataaagag   7440
gaagcattta gcgatcagct ggaactgatt aatctgctga atctggataa taccgtgtg    7500 accgaagatt tcgaattaga agcagatgag atcggcaaat tcctggattt taatggcaac   7560
aaagtgaagg acaacaaaga gcttaagaag ttcgacacca caagatcta ttttgatggc    7620 gagaacatca tcaaacaccg tgccttttat aacatcaaaa aatacggtat gctgaacctg   7680
ctggaaaaga ttgcagataa agcaggctat aaaatcagca ttgaagagtt gaaaaaatac   7740
agcaacaaga aaaacgagat tgagaaaaac cacaaaatgc aagaaaatct gcaccgcaaa   7800
tatgcacgtc cgcgtaaaga tgaaaaattc accgatgaag attatgaaag ctacaaacag   7860
gccatcgaaa acatcgaaga atatacccat ctgaagaaca agtcgaatt caacgaactg    7920 aatctgctgc agggtctgct gctgcgtatt ctgcatcgtc tggtgggtta taccagcatt   7980
tgggaacgtg atctgcgttt tcgcctgaaa ggtgaatttc ctgaaaacca gtatatcgag   8040
```

```
gaaatcttca acttcgagaa taaaaagaat gtgaagtata aaggtggcca gatcgtcgag    8100
aaatatatca aattctacaa agaactgcac cagaacgacg aggtgaaaat caacaaatat    8160
agcagcgcga acatcaaagt gctgaaacaa gagaaaaaag acctgtacat ccgcaactat    8220
atcgcccact ttaactatat tccgcatgca gaaattagtc tgctggaagt tctggaaaac    8280
ctgcgtaaac tgctgtcata tgatcgtaaa cttaaaaacg ccgtgatgaa aagcgttgtg    8340
gacatcctga aagagtatgg ttttgttgcg acctttaaaa tcggtgccga taaaaagatt    8400
ggtattcaga ccctggaaag cgagaagatt gttcacctga aaaatcttaa gaaaaagaaa    8460
cttatgaccg atcgcaatag cgaggaactg tgtaaactgg tgaaaattat gtttgagtat    8520
aaaatggaag agaagaaatc cgaaaatggg gatccgaatt cgagctccgt cgacaagctt    8580
gcggccgcac tcgagcacca ccaccaccac cactgagatc cggctgctaa caaagcccga    8640
aaggaagctg agttggctgc tgccaccgct gagcaataac tagcataacc ccttggggcc    8700
tctaaacggg tcttgagggg ttttttgctg aaaggaggaa ctatatccgg at            8752

<210> SEQ ID NO 37
<211> LENGTH: 9907
<212> TYPE: DNA
<213> ORGANISM: Artificial Sequence
<220> FEATURE:
<223> OTHER INFORMATION: Synthetic

<400> SEQUENCE: 37
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt gccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttcttttcc     840 agacttgttc aacaggccag ccattacgct cgtcatcaaa atcactcgca tcaaccaaac     900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
```

```
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggttttt cttttcacca gtgagacggg caacagctga ttgcccttca    3660
ccgcctggcc ctgagagagt tgcagcaagc ggtccacgct ggtttgcccc agcaggcgaa    3720
```

```
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgaaaatcg aagaaggtaa actggtaatc   5100
tggattaacg gcgataaagg ctataacggt ctcgctgaag tcggtaagaa attcgagaaa   5160
gataccggaa ttaaagtcac cgttgagcat ccggataaac tggaagagaa attcccacag   5220
gttgcggcaa ctggcgatgg ccctgacatt atcttctggg cacacgaccg ctttggtggc   5280
tacgctcaat ctggcctgtt ggctgaaatc accccggaca aagcgttcca ggacaagctg   5340
tatccgttta cctgggatgc cgtacgttac aacggcaagc tgattgctta cccgatcgct   5400
gttgaagcgt tatcgctgat ttataacaaa gatctgctgc cgaacccgcc aaaaacctgg   5460
gaagagatcc cggcgctgga taagaactg aaagcgaaag gtaagagcgc gctgatgttc   5520
aacctgcaag aaccgtactt cacctggccg ctgattgctg ctgacggggg ttatgcgttc   5580
aagtatgaaa acggcaagta cgacattaaa gacgtgggcg tggataacgc tggcgcgaaa   5640
gcgggtctga ccttcctggt tgacctgatt aaaaacaaac acatgaatgc agacaccgat   5700
tactccatcg cagaagctgc ctttaataaa ggcgaaacag cgatgaccat caacggcccg   5760
tgggcatggt ccaacatcga caccagcaaa gtgaattatg gtgtaacggt actgccgacc   5820
ttcaagggtc aaccatccaa accgttcgtt ggcgtgctga gcgcaggtat taacgccgcc   5880
agtccgaaca aagagctggc aaaagagttc ctcgaaaact atctgctgac tgatgaaggt   5940
ctggaagcgg ttaataaaga caaaccgctg ggtgccgtag cgctgaagtc ttacgaggaa   6000
gagttggtga agatccgcg tattgccgcc actatgaaa acgccagaa aggtgaaatc   6060
atgccgaaca tcccgcagat gtccgctttc tggtatgccg tgcgtactgc ggtgatcaac   6120
```

```
gccgccagcg gtcgtcagac tgtcgatgaa gccctgaaag acgcgcagac taattcgagc   6180
tcgaacaaca acaacaataa caataacaac aacctcggga tcgagggaag gaaggtgacc   6240
aaagttggtg gtatcagcca taaaaagtat accagcgaag gtcgtctggt taaaagcgaa   6300
agcgaagaaa atcgtaccga tgaacgtctg agcgcactgc tgaatatgcg tctggatatg   6360
tatatcaaaa atccgagcag caccgaaacc aagaaaatc agaaacgtat cggcaagctg    6420
aaaaagttct tcagcaacaa aatggtgtac ctgaaagata cacccctgag cctgaaaaac   6480
ggcaagaaag aaaatatcga tcgcgagtat agcgaaaccg atattctgga aagtgatgtg   6540
cgtgacaaaa aaaactttgc cgtcctgaaa aagatctatc tgaacgaaaa tgtgaacagc   6600
gaagaactgg aagtgtttcg caacgacatt aaaaagaagc tgaacaagat caacagcctg   6660
aaatatagct tcgagaaaaa caaagccaac tatcagaaga tcaacgagaa caacatcgaa   6720
aaagtggaag gtaaaagcaa gcgcaacatc atctatgatt attatcgtga aagcgccaaa   6780
cgtgatgcct atgttagcaa tgttaaagag gccttcgaca agctgtataa agaagaagat   6840
attgccaaac tggtgctgga aattgaaaat ctgaccaagc tggaaaaata caagatccgc   6900
gaattctatc acgaaatcat tggtcgcaaa aacgataaag agaacttcgc caaaatcatc   6960
tacgaagaaa ttcagaacgt gaataacatg aaagaactga tcgagaaagt tccggatatg   7020
agcgaactga aaaaagcca ggtgttctac aaatattacc tggacaaaga ggaactgaac   7080
gataaaaaca tcaaatacgc cttttgccac ttcgtggaaa tcgaaatgag ccagctgctg   7140
aaaaactatg tgtataaacg cctgagcaac atcagcaacg ataagattaa acgcatcttc   7200
gagtaccaga acctgaagaa actgattgaa aacaaactgc ttaacaaact ggataccat   7260 gtgcgtaatt gcggcaaata caactattat ctgcaggatg gtgaaattgc gaccagcgat   7320
tttattgcac gtaatcgtca gaatgaagcc tttctgcgta acattattgg tgttagcagc   7380
gttgcatatt ttagcctgcg taatatcctg gaaaccgaaa acgagaatga tatcaccggt   7440
cgtatgcgtg gtaaaaccgt gaaaaacaat aaaggcgaag agaaatatgt gagcggtgag   7500
gtggataaaa tctacaacga aaacaaaaag aacgaagtga agaaaaacct gaaaatgttt   7560
tacagctacg actttaacat ggacaacaag aacgagatcg aagatttttt cgccaacatt   7620
gatgaagcca ttagcagcat tcgtcatggc attgttcact ttaatctgga acttgagggc   7680
aaagacatct tcgcgtttaa aaacattgca ccgagcgaga ttagcaaaaa gatgttccag   7740
aacgaaatta cgagaaaaaa actgaaactg aagatctttc gccagctgaa tagcgcaaat   7800
gtttttcgct atcttgagaa atacaaaatc ctgaactatc tgaaacgcac ccgctttgaa   7860
tttgtgaaca aaaacattcc gtttgtgccg agctttacca aactgtatag ccgtattgat   7920
gatctgaaaa acagcctggg catttattgg aaaaccccga aaaccaacga tgataacaag   7980
acgaaagaaa tcatcgatgc ccagatttat ctgcttaaga acatctacta tggcgaattt   8040
ctgaactatt ttatgagcaa caacggcaac ttctttgaaa tcagcaaaga gattatcgag   8100
ctgaataaaa acgacaaacg caatctgaaa accggcttct ataaactgca gaagtttgag   8160
gatatccaag aaaagatccc gaaagaatat ctggcgaata ttcagagcct gtacatgatt   8220
aatgcaggca atcaggatga ggaagagaaa gataccata tcgatttcat ccagaaaatc   8280
tttctgaaag gctttatgac ctatctggcc aataatggtc gtctgagtct gatttatatc   8340
ggtagtgatg aagaaaccaa taccagcctg gcagaaaaaa aacaagagtt cgataagttc   8400
ctgaagaagt acgaacagaa caacaacatc aagatcccgt atgaaatcaa tgaatttctg   8460
```

| | |
|---|---:|
| cgcgaaatca agctgggcaa cattctgaaa tacaccgaac gcctgaatat gttctatctg | 8520 |
| attctgaaac tgctgaacca taaagagctg acgaatctga aaggtagcct ggaaaagtat | 8580 |
| cagagcgcaa ataaagagga agcatttagc gatcagctgg aactgattaa tctgctgaat | 8640 |
| ctggataata accgtgtgac cgaagatttc gaattagaag cagatgagat cggcaaattc | 8700 |
| ctggatttta atggcaacaa agtgaaggac aacaaagagc ttaagaagtt cgacaccaac | 8760 |
| aagatctatt ttgatggcga gaacatcatc aaacaccgtg cctttttataa catcaaaaaa | 8820 |
| tacggtatgc tgaacctgct ggaaaagatt gcagataaag caggctataa aatcagcatt | 8880 |
| gaagagttga aaaatacag caacaagaaa acgagattg agaaaaacca caaaatgcaa | 8940 |
| gaaaatctgc accgcaaata tgcacgtccg cgtaaagatg aaaaattcac cgatgaagat | 9000 |
| tatgaaagct acaaacaggc catcgaaaac atcgaagaat ataccatctc gaagaacaaa | 9060 |
| gtcgaattca acgaactgaa tctgctgcag gtctgctgc tgcgtattct gcatcgtctg | 9120 |
| gtgggttata ccagcatttg gaacgtgat ctgcgttttc gcctgaaagg tgaatttcct | 9180 |
| gaaaaccagt atatcgagga atcttcaac ttcgagaata aaaagaatgt gaagtataaa | 9240 |
| ggtggccaga tcgtcgagaa atatatcaaa ttctacaaag aactgcacca gaacgacgag | 9300 |
| gtgaaaatca caaatatag cagcgcgaac atcaaagtgc tgaaacaaga gaaaaaagac | 9360 |
| ctgtacatcc gcaactatat cgcccacttt aactatattc gcatgcagaa aattagtctg | 9420 |
| ctggaagttc tggaaaacct gcgtaaactg ctgtcatatg atcgtaaact taaaaacgcc | 9480 |
| gtgatgaaaa gcgttgtgga catcctgaaa gagtatggtt ttgttgcgac ctttaaaatc | 9540 |
| ggtgccgata aaaagattgg tattcagacc ctggaaagcg agaagattgt tcacctgaaa | 9600 |
| aatcttaaga aaagaaact tatgaccgat cgcaatagcg aggaactgtg taaactggtg | 9660 |
| aaaattatgt ttgagtataa aatggaagag aagaaatccg aaaatgatcc gaattcgagc | 9720 |
| tccgtcgaca agcttgcggc cgcactcgag caccaccacc accaccactg agatccggct | 9780 |
| gctaacaaag cccgaaagga agctgagttg gctgctgcca ccgctgagca ataactagca | 9840 |
| taaccccttg gggcctctaa acgggtcttg agggtttt tgctgaaagg aggaactata | 9900 |
| tccggat | 9907 |

<210> SEQ ID NO 38
<211> LENGTH: 9442
<212> TYPE: DNA
<213> ORGANISM: Artificial Sequence
<220> FEATURE:
<223> OTHER INFORMATION: Synthetic

<400> SEQUENCE: 38

| | |
|---|---:|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct tgacgttgg agtccacgtt | 300 |
| ctttaatagt ggactcttgt tccaaactgg aacaacactc aaccctatct cggtctattc | 360 |
| ttttgattta agggatttt gccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg aattaattct tagaaaaact catcgagcat caaatgaaac tgcaatttat | 600 |

```
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg caacgctac    1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccggggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccaggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg cctttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
```

```
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgggtaacc tgtttggtca taacgttgg   5100 tatgaagtgc gcgacaaaaa agactttaaa atcaaacgca aggtgaaagt gaaacgcaac   5160
tatgatggca acaaatatat cctgaacatc aacgagaaca acaacaaaga gaagatcgat   5220
aataataaat tcatccgcaa atacatcaac tacaaaaaaa acgataacat cctgaaagaa   5280 ttcaccccgca agtttcatgc aggcaacatt ctgtttaaac tgaaaggcaa agaaggcatc   5340
```

```
attcgcatcg aaaacaatga tgattttctg gaaaccgaag aggtggtgct gtatattgaa    5400
gcatatggca aaagcgaaaa actgaaggca ctgggcatta ccaaaaaaaa gattatcgat    5460
gaagccattc gccagggtat taccaaagat gacaaaaaga tcgagatcaa gcgccaagaa    5520
aacgaagaag aaatcgaaat tgatatccgc gacgagtata ccaataaaac cctgaatgat    5580
tgcagcatta ttctgcgcat tatcgagaat gatgagctgg aaacgaaaaa gagcatctac    5640
gagatcttca aaacatcaa catgagcctg tacaaaatca tcgagaaaat tatcgaaaac    5700
gaaaccgaga aggtgttcga gaatcgctat tatgaagaac atctgcgtga aaactgctg    5760 aaagatgata aaattgatgt gatcctgacc aacttcatgg aaatccgcga aaagattaaa    5820
agcaacctgg aaattctggg cttcgtgaaa ttctatctga atgttggtgg cgacaagaaa    5880
aaaagcaaga acaagaaaat gctggtcgaa aaaattctga acattaacgt tgatctgacc    5940
gtggaagata ttgccgattt tgtgattaaa gagctggaat tctggaacat caccaaacgc    6000
attgagaagg tgaaaaaagt gaacaacgag ttcctggaaa aacgtcgtaa tcgcaccctat    6060 atcaaaagct atgttctgct ggataagcac gagaaattca aaattgaacg cgagaacaaa    6120
aaggacaaaa tcgtgaagtt tttcgtggaa aatatcaaaa acaacagcat caaagaaaaa    6180
atcgagaaga tcctggccga gttcaaaatc gatgaactga tcaaaaagct ggaaaaagaa    6240
ctgaaaaaag caactgcga taccgaaatt ttcggcatct ttaagaaaca ctataaagtg    6300
aacttcgata gcaaaaaatt cagcaaaaag agcgacgaag agaaagagct gtataagatc    6360
atttaccgct atctgaaagg ccgtattgaa aaaatcctgg tgaatgaaca gaaagtgcgc    6420
ctgaaaaaaa tggaaaaaat tgagattgag aagattctga acgagagcat cctgagtgag    6480
aaaatcctga acgtgttaa acagtatacc ctggaacaca ttatgtatct gggtaaactg    6540
cgccataacg atattgatat gaccaccgtt aataccgatg atttcagccg tctgcatgca    6600
aaagaagaac tggatctgga actgattacc ttttttgcaa gcaccaatat ggaactgaac    6660
aagatcttta gccgtgaaaa cattaacaac gacgagaaca ttgatttctt tggtggtgat    6720
cgcgagaaaa actatgtcct ggataaaaag atcctgaata gcaaaatcaa gatcatccgc    6780
gatctggatt tcatcgacaa taagaacaac attaccaaca actttattcg caaatttacc    6840
aaaattggca ccaatgaacg caaccgtatt ctgcatgcca ttagcaaaga acgtgatctg    6900
cagggcaccc aggatgatta taacaaagtg attaacatca tccagaacct gaaaatctcc    6960
gatgaagaag ttagcaaagc actgaatctg gatgtggtgt tcaaagataa gaaaaatatc    7020
atcaccaaga tcaacgatat caaaatcagc gaagagaaca taacgacat caaatatctg    7080 ccgagcttta gcaaagttct gccggaaatt cttaatctgt atcgcaataa cccgaaaaac    7140
gaaccgtttg ataccatcga aacagagaaa attgttctga acgccctgat ctatgtgaac    7200
aaagaactgt acaagaaact gatcctggaa gatgatctgg aagagaacga atcgaaaaac    7260
atctttctgc aagagctgaa aaagaccctg gtaacattg atgagatcga tgaaaacatc    7320
atcgaaaatt actacaagaa cgcacagatt agcgcaagca aaggtaataa caaagccatc    7380
aaaaaatacc agaaaaaggt gatcgaatgc tacattggtt atctgcgcaa aaactacgaa    7440
gaactgttcg atttcagcga tttcaaaatg aacatccaag agatcaagaa gcagatcaag    7500
gacattaacg acaacaaaac ctatgaacgc atcaccgtta aaaccagcga taaaccatt    7560 gtgatcaacg acgatttcga gtacatcatt agcattttg cactgctgaa ttccaacgcc    7620
gtgatcaaca aaattcgcaa tcgcttttt gccaccagtg tttggctgaa taccagcgaa    7680
```

| | |
|---|---|
| tatcagaaca ttatcgatat cctggatgag atcatgcagc tgaatacact gcgtaatgaa | 7740 |
| tgcattaccg aaaactggaa tctgaacctt gaagaattta ttcagaaaat gaaagagatc | 7800 |
| gagaaagact tcgacgactt caaaatccag accaaaaaag aaatcttcaa caactactac | 7860 |
| gaggacatca aaataacat tctgaccgaa ttcaaagacg atattaacgg ctgtgacgtg | 7920 |
| ctggaaaaga gttggaaaaa gatcgttatc ttcgatgacg aaaccaaatt cgaaatcgac | 7980 |
| aaaaagtcca acatccttca ggatgaacag cgtaaactga gcaatatcaa caagaaagac | 8040 |
| ctgaagaaga aggtcgacca gtacatcaaa gacaaagacc aagaaattaa gagcaaaatc | 8100 |
| ctgtgccgca tcatctttaa cagcgacttt ctgaaaaagt ataagaaaga gattgacaac | 8160 |
| ctgatcgagg atatggaaag cgagaacgaa aacaagtttc aagagatcta ctatccgaaa | 8220 |
| gaacgcaaaa acgagctgta catctacaag aagaacctgt tcctgaatat tggcaacccg | 8280 |
| aacttcgaca aaatctatgg tctgatcagc aacgacatta aatggccga tgcaaaattc | 8340 |
| ctgtttaata tcgatggtaa aaacatccgt aaaaacaaaa ttagcgagat cgacgcgatc | 8400 |
| ctgaaaaacc tgaacgataa actgaatggc tacagcaaag aatataaaga gaaatacatt | 8460 |
| aaaaagctga agaaaatga cgacttcttc gccaagaaca tccagaataa aaactataaa | 8520 |
| agcttcgaga aggactacaa tcgcgtgtcc gaatataaga aaattcgtga tctggtggaa | 8580 |
| ttcaactatc tgaacaaaat cgaaagctat ctgatcgata tcaactggaa actggcaatt | 8640 |
| cagatggcac gttttgagcg tgatatgcac tatattgtta atggtctgcg tgaactgggc | 8700 |
| atcattaaac tgagtggtta taatccggc attagccgtg catatccgaa acgtaatggt | 8760 |
| tccgatggtt tttataccac caccgcctat tacaaatttt tcgacgaaga aagctacaag | 8820 |
| aaatttgaga aatttgcta cggcttcggc attgatctga gcgaaaatag cgaaattaac | 8880 |
| aagccggaaa atgagagcat tcgcaactat atctcccact tttatatcgt gcgtaatccg | 8940 |
| tttgccgatt atagcattgc agagcagatt gatcgtgtta gcaatctgct gagctatagt | 9000 |
| acccgttata caaatagcac ctatgccagc gtgtttgagg tgtttaaaaa ggatgttaac | 9060 |
| ctggactatg acgagctgaa gaaaaagttc aaactgatcg gcaacaatga catcctggaa | 9120 |
| cgtctgatga aaccgaaaaa agttagtgtg ctggaacttg agagctacaa cagcgattat | 9180 |
| atcaagaacc tgattatcga gctgctgacc aagattgaaa ataccaatga taccctgggg | 9240 |
| gatccgaatt cgagctccgt cgacaagctt gcggccgcac tcgagcacca ccaccaccac | 9300 |
| cactgagatc cggctgctaa caaagcccga aggaagctg agttggctgc tgccaccgct | 9360 |
| gagcaataac tagcataacc ccttggggcc tctaaacggg tcttgagggg ttttttgctg | 9420 |
| aaaggaggaa ctatatccgg at | 9442 |

<210> SEQ ID NO 39
<211> LENGTH: 10597
<212> TYPE: DNA
<213> ORGANISM: Artificial Sequence
<220> FEATURE:
<223> OTHER INFORMATION: Synthetic

<400> SEQUENCE: 39

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |

```
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcaggggggc ggagcctat ggaaaaacgc cagcaacgcg   2100 gccttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
```

```
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtcccgga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgcggccac gatgcgtccg gcgtagagga tcgagatctc gatcccgcga   4980
aattaatacg actcactata ggggaattgt gagcggataa caattcccct ctagaaataa   5040
```

```
ttttgtttaa ctttaagaag gagatatacc atgaaaatcg aagaaggtaa actggtaatc    5100
tggattaacg gcgataaagg ctataacggt ctcgctgaag tcggtaagaa attcgagaaa    5160
gataccggaa ttaaagtcac cgttgagcat ccggataaac tggaagagaa attcccacag    5220
gttgcggcaa ctggcgatgg ccctgacatt atcttctggg cacacgaccg ctttggtggc    5280
tacgctcaat ctggcctgtt ggctgaaatc accccggaca aagcgttcca ggacaagctg    5340
tatccgttta cctgggatgc cgtacgttac aacggcaagc tgattgctta cccgatcgct    5400
gttgaagcgt tatcgctgat ttataacaaa gatctgctgc cgaacccgcc aaaaacctgg    5460
gaagagatcc cggcgctgga taagaactg aaagcgaaag gtaagagcgc gctgatgttc    5520
aacctgcaag aaccgtactt cacctggccg ctgattgctg ctgacggggg ttatgcgttc    5580
aagtatgaaa acggcaagta cgacattaaa gacgtgggcg tggataacgc tggcgcgaaa    5640
gcgggtctga ccttcctggt tgacctgatt aaaaacaaac acatgaatgc agacaccgat    5700
tactccatcg cagaagctgc ctttaataaa ggcgaaacag cgatgaccat caacggcccg    5760
tgggcatggt ccaacatcga caccagcaaa gtgaattatg gtgtaacggt actgccgacc    5820
ttcaagggtc aaccatccaa accgttcgtt ggcgtgctga gcgcaggtat taacgccgcc    5880
agtccgaaca aagagctggc aaaagagttc ctcgaaaact atctgctgac tgatgaaggt    5940
ctggaagcgg ttaataaaga caaaccgctg ggtgccgtag cgctgaagtc ttacgaggaa    6000
gagttggtga agatccgcg tattgccgcc actatggaaa cgcccagaa aggtgaaatc    6060
atgccgaaca tcccgcagat gtccgctttc tggtatgccg tgcgtactgc ggtgatcaac    6120
gccgccagcg gtcgtcagac tgtcgatgaa gccctgaaag acgcgcagac taattcgagc    6180
tcgaacaaca caacaataa caataacaac aacctcggga tcgagggaag gggtaacctg    6240
tttggtcata acgttggta tgaagtgcgc gacaaaaag actttaaaat caaacgcaag    6300
gtgaaagtga acgcaacta tgatggcaac aaatatatcc tgaacatcaa cgagaacaac    6360
aacaaagaga agatcgataa taataaattc atccgcaaat acatcaacta caaaaaaaac    6420
gataacatcc tgaaagaatt cacccgcaag tttcatgcag gcaacattct gtttaaactg    6480
aaaggcaaag aaggcatcat tcgcatcgaa aacaatgatg attttctgga aaccgaagag    6540
gtggtgctgt atattgaagc atatggcaaa agcgaaaaac tgaaggcact gggcattacc    6600
aaaaaaaaga ttatcgatga agccattcgc cagggtatta ccaaagatga caaaaagatc    6660
gagatcaagc gccaagaaaa cgaagaagaa atcgaaattg atatccgcga cgagtatacc    6720
aataaaccc tgaatgattg cagcattatt ctgcgcatta tcgagaatga tgagctggaa    6780
acgaaaaaga gcatctacga gatcttcaaa aacatcaaca tgagcctgta caaaatcatc    6840
gagaaaatta tcgaaaacga aaccgagaag gtgttcgaga atcgctatta tgaagaacat    6900
ctgcgtgaga aactgctgaa agatgataaa attgatgtga tcctgaccaa cttcatggaa    6960
atccgcgaaa agattaaaag caacctggaa attctgggct tcgtgaaatt ctatctgaat    7020
gttggtggcg acaagaaaaa aagcaagaac aagaaaatgc tggtcgaaaa aattctgaac    7080
attaacgttg atctgaccgt ggaagatatt gccgattttg tgattaaaga gctggaattc    7140
tggaacatca ccaaacgcat tgagaaggtg aaaaaagtga caacgagtt cctggaaaaa    7200
cgtcgtaatc gcacctatat caaaagctat gttctgctgg ataagcacga gaaattcaaa    7260
attgaacgcg agaacaaaaa ggacaaaatc gtgaagtttt tcgtggaaaa tatcaaaaac    7320
aacagcatca agaaaaaaat cgagaagatc ctggccgagt tcaaaatcga tgaactgatc    7380
```

```
aaaaagctgg aaaaagaact gaaaaaaggc aactgcgata ccgaaatttt cggcatcttt    7440
aagaaacact ataaagtgaa cttcgatagc aaaaaattca gcaaaaagag cgacgaagag    7500
aaagagctgt ataagatcat ttaccgctat ctgaaaggcc gtattgaaaa aatcctggtg    7560
aatgaacaga aagtgcgcct gaaaaaaatg gaaaaaattg agattgagaa gattctgaac    7620
gagagcatcc tgagtgagaa aatcctgaaa cgtgttaaac agtataccct ggaacacatt    7680
atgtatctgg gtaaactgcg ccataacgat attgatatga ccaccgttaa taccgatgat    7740
ttcagccgtc tgcatgcaaa agaagaactg gatctggaac tgattacctt ttttgcaagc    7800
accaatatgg aactgaacaa gatctttagc cgtgaaaaca ttaacaacga cgagaacatt    7860
gatttctttg gtggtgatcg cgagaaaaac tatgtcctgg ataaaaagat cctgaatagc    7920
aaaatcaaga tcatccgcga tctggatttc atcgacaata agaacaacat taccaacaac    7980
tttattcgca aatttaccaa aattggcacc aatgaacgca accgtattct gcatgccatt    8040
agcaaagaac gtgatctgca gggcacccag gatgattata acaaagtgat taacatcatc    8100
cagaacctga aaatctccga tgaagaagtt agcaaagcac tgaatctgga tgtggtgttc    8160
aaagataaga aaaatatcat caccaagatc aacgatatca aaatcagcga agagaacaat    8220
aacgacatca atatctgcc gagctttagc aaagttctgc cggaaattct taatctgtat    8280
cgcaataacc cgaaaaacga accgtttgat accatcgaaa cagagaaaat tgttctgaac    8340
gccctgatct atgtgaacaa agaactgtac aagaaactga tcctggaaga tgatctggaa    8400
gagaacgaat cgaaaaacat ctttctgcaa gagctgaaaa agaccctggg taacattgat    8460
gagatcgatg aaaacatcat cgaaaattac tacaagaacg cacagattag cgcaagcaaa    8520
ggtaataaca aagccatcaa aaaataccag aaaaaggtga tcgaatgcta cattggttat    8580
ctgcgcaaaa actacgaaga actgttcgat ttcagcgatt tcaaaatgaa catccaagag    8640
atcaagaagc agatcaagga cattaacgac aacaaaacct atgaacgcat caccgttaaa    8700
accagcgata aaaccattgt gatcaacgac gatttcgagt acatcattag cattttttgca    8760 ctgctgaatt ccaacgccgt gatcaacaaa attcgcaatc gcttttttgc caccagtgtt    8820
tggctgaata ccagcgaata tcagaacatt atcgatatcc tggatgagat catgcagctg    8880
aatacactgc gtaatgaatg cattaccgaa aactggaatc tgaaccttga agaatttatt    8940
cagaaaatga aagagatcga gaagacttc gacgacttca aaatccagac caaaaaagaa    9000
atcttcaaca actactacga ggacatcaaa aataacattc tgaccgaatt caaagacgat    9060
attaacggct gtgacgtgct ggaaagaag ttggaaaaga tcgttatctt cgatgacgaa    9120
accaaattcg aaatcgacaa aaagtccaac atccttcagg atgaacagcg taaactgagc    9180
aatatcaaca agaagacct gaagaagaag gtcgaccagt acatcaaaga caagaccaa    9240 gaaattaaga gcaaaatcct gtgccgcatc atctttaaca gcgactttct gaaaaagtat    9300
aagaaagaga ttgacaacct gatcgaggat atggaaagcg agaacgaaaa caagtttcaa    9360
gagatctact atccgaaaga acgcaaaaac gagctgtaca tctacaagaa gaacctgttc    9420
ctgaatattg gcaacccgaa cttcgacaaa atctatggtc tgatcagcaa cgacattaaa    9480
atggccgatg caaattcct gtttaatatc gatggtaaaa acatccgtaa aaacaaaatt    9540
agcgagatcg acgcgatcct gaaaaacctg aacgataaac tgaatggcta cagcaaagaa    9600
tataaagaga aatacattaa aaagctgaaa gaaaatgacg acttcttcgc caagaacatc    9660
cagaataaaa actataaaag cttcgagaag gactacaatc gcgtgtccga atataagaaa    9720
attcgtgatc tggtggaatt caactatctg aacaaaatcg aaagctatct gatcgatatc    9780
```

```
aactggaaac tggcaattca gatggcacgt tttgagcgtg atatgcacta tattgttaat    9840
ggtctgcgtg aactgggcat cattaaactg agtggttata ataccggcat tagccgtgca    9900
tatccgaaac gtaatggttc cgatggtttt tataccacca ccgcctatta caaattttc    9960 gacgaagaaa gctacaagaa atttgagaaa atttgctacg gcttcggcat tgatctgagc   10020
gaaaatagcg aaattaacaa gccggaaaat gagagcattc gcaactatat ctcccacttt   10080
tatatcgtgc gtaatccgtt tgccgattat agcattgcag agcagattga tcgtgttagc   10140
aatctgctga gctatagtac ccgttataac aatagcacct atgccagcgt gtttgaggtg   10200
tttaaaaagg atgttaacct ggactatgac gagctgaaga aaaagttcaa actgatcggc   10260
aacaatgaca tcctggaacg tctgatgaaa ccgaaaaaag ttagtgtgct ggaacttgag   10320
agctacaaca gcgattatat caagaacctg attatcgagc tgctgaccaa gattgaaaat   10380
accaatgata ccctggatcc gaattcgagc tccgtcgaca gcttgcggc cgcactcgag   10440 caccaccacc accaccactg agatccggct gctaacaaag cccgaaagga agctgagttg   10500
gctgctgcca ccgctgagca ataactagca taaccccttg gggcctctaa acgggtcttg   10560
aggggttttt tgctgaaagg aggaactata tccggat                            10597

<210> SEQ ID NO 40
<211> LENGTH: 8731
<212> TYPE: DNA
<213> ORGANISM: Artificial Sequence
<220> FEATURE:
<223> OTHER INFORMATION: Synthetic

<400> SEQUENCE: 40
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcggggc tcccctttagg    180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta agggattt tgccgattc ggcctattgg ttaaaaaatg agctgattta    420 acaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttcttcc    840 agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
```

```
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccggggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt cctgcgtta   2160 tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
```

```
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg cgcgcattg     3840 cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatatacc atgaaagtga ccaaagtgga tggcatcagc    5100
cacaaaaaat acatcgaaga aggcaaactg gttaaaagca ccagcgaaga aaatcgtacc    5160
agcgaacgtc tgagcgaact gctgagcatt cgtctggata tctatatcaa aaatccggat    5220
aatgccagcg aggaagaaaa ccgtattcgt cgtgaaaacc tgaaaaagtt cttcagcaat    5280
aaagtgctgc acctgaaaga tagcgttctg tatctgaaaa accgcaaaga aaaaaatgcc    5340
gtgcaggaca aaaactatag cgaagaggat atcagcgagt atgacctgaa gaacaaaaat    5400
agctttagcg tgctgaaaaa aatcctgctg aatgaagatg tgaatagcga ggaactggaa    5460
atctttcgta aagatgttga agccaagctg aacaaaatca cagcctgaa atatagcttt     5520 gaagaaaaca aggccaacta tcagaaaatc aacgagaaca acgtggaaaa agttggtggt    5580
aaaagcaaac gcaacatcat ctatgattat tatcgcgaaa gcgcgaaacg caacgattat    5640
atcaataatg tgcaagaggc cttcgacaaa ctgtacaaaa aagaggacat cgaaaaactg    5700 tttttttctga tcgagaacag caagaagcac gagaaataca aaatccgcga gtactaccat    5760
aaaatcatcg gtcgcaaaaa cgataaagag aacttcgcca aaatcatcta cgaagaaatt    5820
cagaacgtga acaacatcaa agaactgatc gaaaaaattc cggacatgag cgagctgaag    5880
aaaagccagg tgttctataa atactacctg gacaaagagg aactgaacga caaaaacatc    5940
```

```
aaatatgcct tttgccactt cgtcgaaatt gaaatgagcc agctgcttaa aaactacgtg   6000
tataaacgcc tgagcaacat cagcaacgat aaaatcaaac gtatctttga atatcagaat   6060
ctgaagaaac tgattgaaaa caaactgctg aacaagctgg atacctatgt tcgtaattgc   6120
ggcaaataca actactatct gcaggttggt gaaattgcaa ccagcgattt tattgcacgt   6180
aatcgtcaga atgaagcctt tctgcgtaac attattggtg ttagcagcgt tgcatatttt   6240
agcctgcgta atattctgga aaccgaaaac gaaaatggca ttaccggtcg tatgcgtggt   6300
aaaaccgtta aaaacaataa aggcgaagag aagtatgtga gcggtgaagt ggataaaatc   6360
tataacgaaa acaagcagaa cgaagtgaaa gaaaatctga aatgttttta cagctacgac   6420
ttcaacatgg acaacaaaaa cgagatcgaa gatttcttcg ccaacattga tgaagccatt   6480
agcagtattc gtcatggcat tgtgcacttt aatctggaac ttgaaggcaa agacatcttc   6540
gcgtttaaaa acattgcacc gagcgagatc agcaaaaaaa tgtttcagaa cgagattaac   6600
gaaaaaaaac tgaaactgaa aatcttcaaa cagctgaata gcgccaacgt gttcaactat   6660
tatgagaaag acgtgatcat caaataccct aaaaacacca aattcaactt cgtgaataaa   6720
aacatcccgt tgttccgag cttcaccaaa ctgtataaca aaattgaaga tctgcgcaat   6780
accctgaagt ttttttggag cgttccgaaa gacaaagaag aaaaagacgc acagatctac   6840
ctgcttaaga acatctatta tggcgaattt ctgaacaaat tcgtgaaaaa tagcaaagtg   6900
ttcttcaaaa tcaccaacga ggtgatcaag attaacaaac agcgtaatca gaaaaccggt   6960
cactacaaat accagaagtt tgagaacatt gaaaaaaccg tgccggttga atatctggca   7020
attattcaga gccgtgagat gattaacaac caggataaag aagagaaaaa cacctacatc   7080
gatttcatcc agcagatctt tctgaaaggc tttatcgatt acctgaacaa gaacaacctg   7140
aagtatatcg agtcgaacaa caataacgac aacaacgaca tctttagcaa aatcaaaatc   7200
aagaaagata ataagaaaa atacgacaag atcctgaaaa actatgagaa gcacaaccgc   7260
aacaaagaaa ttccgcatga gatcaatgaa tttgtgcgcg aaattaaact gggcaaaatc   7320
ctgaaataca ccgagaacct gaatatgttc tatctgattc tgaagctgct gaaccataaa   7380
gagctgacca atctgaaagg tagcctggaa aaatatcaga gcgcaaacaa agaagagaca   7440
ttttctgacg aactggaact gattaatctg ctgaatctgg ataataaccg tgtgaccgaa   7500
gattttgaac tggaagcaaa tgaaatcggc aaattcctgg atttcaatga gaacaaaatt   7560
aaggaccgga aagagcttaa aaagtttgat accaacaaaa tctacttcga cggcgagaac   7620
attatcaaac atcgtgcctt ttataacatc aaaaagtatg gcatgctgaa cctgctggaa   7680
aaaattgcag ataaagccaa gtacaaaatt agcctgaaag aacttaaaga gtacagcaac   7740
aaaaagaacg aaatcgagaa gaactatacc atgcagcaga tctgcatcg taaatatgca   7800 cgtccgaaaa aagacgagaa attcaacgat gaggactata agaatacga gaaagccatt   7860 ggcaacatcc agaaatatac ccacttgaaa aacaaagtgg aatttaacga gctgaattta   7920
ctgcagggtc tgctgctgaa aattctgcac cgtctggttg ttataccag catttgggaa   7980 cgtgatctgc gttttcgcct gaaaggtgaa tttcctgaaa accactatat cgaggaaatt   8040
ttcaactttg acaacagcaa aaacgtgaaa tataagagcg gtcagatcgt cgaaaagtac   8100
atcaactttt acaaagaact ttacaaggat aatgtggaaa acgcagcat ctacagcgac   8160 aagaaagtga aaagctgaa gcaagaaaag aaagacctgt acatccgtaa ttatatcgcc   8220
cactttaact atatcccgca tgcagaaatt agtctgctgg aagttctgga aaatctgcgt   8280
aaactgctgt catatgatcg caaactgaag aacgcaatca tgaaaagcat tgtggatatc   8340
```

```
ctgaaagagt atggttttgt cgccaccttt aaaatcggtg ccgataagaa aattgagatt    8400
cagaccctgg aaagcgagaa aattgtgcat cttaagaacc ttaaaaagaa aaaactgatg    8460
accgatcgca acagcgaaga gttatgtgaa ctggtgaaag tgatgttcga atacaaagca    8520
ctggaagggg atccgaattc gagctccgtc gacaagcttg cggccgcact cgagcaccac    8580
caccaccacc actgagatcc ggctgctaac aaagcccgaa aggaagctga gttggctgct    8640
gccaccgctg agcaataact agcataaccc cttggggcct ctaaacgggt cttgaggggt    8700
tttttgctga aaggaggaac tatatccgga t                                   8731
```

<210> SEQ ID NO 41
<211> LENGTH: 9886
<212> TYPE: DNA
<213> ORGANISM: Artificial Sequence
<220> FEATURE:
<223> OTHER INFORMATION: Synthetic

<400> SEQUENCE: 41

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa     1440 cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
```

```
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa acgcctggta tctttatagt cctgtcgggt ttcgccacct ctgacttgag    2040
cgtcgatttt tgtgatgctc gtcaggggggg cggagcctat ggaaaaacgc cagcaacgcg    2100 gccttttac ggttcctggc cttttgctgg cctttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
```

```
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgaaaatcg aagaaggtaa actggtaatc   5100
tggattaacg gcgataaagg ctataacggt ctcgctgaag tcggtaagaa attcgagaaa   5160
gataccggaa ttaaagtcac cgttgagcat ccggataaac tggaagagaa attcccacag   5220
gttgcggcaa ctggcgatgg ccctgacatt atcttctggg cacacgaccg ctttggtggc   5280
tacgctcaat ctggcctgtt ggctgaaatc accccggaca aagcgttcca ggacaagctg   5340
tatccgtttt cctgggatgc cgtacgttac aacggcaagc tgattgctta cccgatcgct   5400
gttgaagcgt tatcgctgat ttataacaaa gatctgctgc cgaacccgcc aaaaacctgg   5460
gaagagatcc cggcgctgga taaagaactg aaagcgaaag gtaagagcgc gctgatgttc   5520
aacctgcaag aaccgtactt cacctggccg ctgattgctg ctgacggggg ttatgcgttc   5580
aagtatgaaa acggcaagta cgacattaaa gacgtgggcg tggataacgc tggcgcgaaa   5640
gcgggtctga ccttcctggt tgacctgatt aaaaacaaac acatgaatgc agacaccgat   5700
tactccatcg cagaagctgc ctttaataaa ggcgaaacag cgatgaccat caacggcccg   5760
tgggcatggt ccaacatcga caccagcaaa gtgaattatg gtgtaacggt actgccgacc   5820
ttcaagggtc aaccatccaa accgttcgtt ggcgtgctga gcgcaggtat taacgccgcc   5880
agtccgaaca aagagctggc aaaagagttc ctcgaaaact atctgctgac tgatgaaggt   5940
ctggaagcgg ttaataaaga caaaccgctg ggtgccgtag cgctgaagtc ttacgaggaa   6000
gagttggtga agatccgcg tattgccgcc actatggaaa cgcccagaa aggtgaaatc   6060 atgccgaaca tcccgcagat gtccgctttc tggtatgccg tgcgtactgc ggtgatcaac   6120
gccgccagcg gtcgtcagac tgtcgatgaa gccctgaaag acgcgcagac taattcgagc   6180
tcgaacaaca acaacaataa caataacaac aacctcggga tcgagggaag gaaagtgacc   6240
aaagtggatg gcatcagcca caaaaaatac atcgaagaag gcaaactggt taaaagcacc   6300
agcgaagaaa atcgtaccag cgaacgtctg agcgaactgc tgagcattcg tctggatatc   6360
```

```
tatatcaaaa atccggataa tgccagcgag gaagaaaacc gtattcgtcg tgaaaacctg    6420
aaaaagttct tcagcaataa agtgctgcac ctgaaagata gcgttctgta tctgaaaaac    6480
cgcaaagaaa aaatgccgt gcaggacaaa aactatagcg aagaggatat cagcgagtat    6540
gacctgaaga acaaaaatag ctttagcgtg ctgaaaaaaa tcctgctgaa tgaagatgtg    6600
aatagcgagg aactggaaat ctttcgtaaa gatgttgaag ccaagctgaa caaaatcaac    6660
agcctgaaat atagctttga agaaaacaag gccaactatc agaaaatcaa cgagaacaac    6720
gtggaaaaag ttggtggtaa aagcaaacgc aacatcatct atgattatta tcgcgaaagc    6780
gcgaaacgca acgattatat caataatgtg caagaggcct tcgacaaaact gtacaaaaaa    6840 gaggacatcg aaaaactgtt ttttctgatc gagaacagca gaagcacga gaaatacaaa    6900 atccgcgagt actaccataa aatcatcggt cgcaaaaacg ataaagagaa cttcgccaaa    6960
atcatctacg aagaaattca gaacgtgaac aacatcaaag aactgatcga aaaaattccg    7020
gacatgagcg agctgaagaa aagccaggtg ttctataaat actacctgga caaagaggaa    7080
ctgaacgaca aaaacatcaa atatgccttt tgccacttcg tcgaaattga aatgagccag    7140
ctgcttaaaa actacgtgta taaacgcctg agcaacatca gcaacgataa aatcaaacgt    7200
atctttgaat atcagaatct gaagaaactg attgaaaaca aactgctgaa caagctggat    7260
acctatgttc gtaattgcgg caaatacaac tactatctgc aggttggtga aattgcaacc    7320
agcgatttta ttgcacgtaa tcgtcagaat gaagcctttc tgcgtaacat tattggtgtt    7380
agcagcgttg catattttag cctgcgtaat attctggaaa ccgaaaacga aaatggtatt    7440
accggtcgta tgcgtggtaa aaccgttaaa aacaataaag gcgaagagaa gtatgtgagc    7500
ggtgaagtgg ataaaatcta taacgaaaac aagcagaacg aagtgaaaga aaatctgaaa    7560
atgttttaca gctacgactt caacatggac aacaaaaacg agatcgaaga tttcttcgcc    7620
aacattgatg aagccattag cagtattcgt catggcattg tgcactttaa tctggaactt    7680
gaaggcaaag acatcttcgc gtttaaaaac attgcaccga gcgagatcag caaaaaaatg    7740
tttcagaacg agattaacga aaaaaaactg aaactgaaaa tcttcaaaca gctgaatagc    7800
gccaacgtgt tcaactatta tgagaaagac gtgatcatca aataccttaa aaacaccaaa    7860
ttcaacttcg tgaataaaaa catcccgttt gttccgagct tcaccaaaact gtataacaaa    7920 attgaagatc tgcgcaatac cctgaagttt ttttggagcg ttccgaaaga caagaagaa    7980 aaagacgcac agatctacct gcttaagaac atctattatg gcgaatttct gaacaaattc    8040
gtgaaaaata gcaaagtgtt cttcaaaatc accaacgagg tgatcaagat taacaaacag    8100
cgtaatcaga aaaccggtca ctacaaatac cagaagtttg agaacattga aaaaaccgtg    8160
ccggttgaat atctggcaat tattcagagc cgtgagatga ttaacaacca ggataaagaa    8220
gagaaaaaca cctacatcga tttcatccag cagatctttc tgaaaggctt tatcgattac    8280
ctgaacaaga acaacctgaa gtatatcgag tcgaacaaca ataacgacaa caacgacatc    8340
tttagcaaaa tcaaaatcaa gaaagataat aaagaaaaat acgacaagat cctgaaaaac    8400
tatgagaagc acaaccgcaa caaagaaatt ccgcatgaga tcaatgaatt tgtgcgcgaa    8460
attaaactgg gcaaaatcct gaaatacacc gagaacctga atatgttcta tctgattctg    8520
aagctgctga accataaaga gctgaccaat ctgaaaggta gcctggaaaa atatcagagc    8580
gcaaacaaag aagagacatt ttctgacgaa ctggaactga ttaatctgct gaatctggat    8640 aataccgtg tgaccgaaga ttttgaactg gaagcaaatg aaatcggcaa attcctggat    8700
ttcaatgaga acaaaattaa ggaccggaaa gagcttaaaa agtttgatac caacaaaatc    8760
```

```
tacttcgacg gcgagaacat tatcaaacat cgtgccttt  ataacatcaa aaagtatggc   8820
atgctgaacc tgctggaaaa aattgcagat aaagccaagt acaaaattag cctgaaagaa   8880
cttaaagagt acagcaacaa aaagaacgaa atcgagaaga actataccat gcagcagaat   8940
ctgcatcgta aatatgcacg tccgaaaaaa gacgagaaat caacgatga  ggactataaa   9000 gaatacgaga aagccattgg caacatccag aaatataccc acttgaaaaa caaagtggaa   9060
tttaacgagc tgaatttact gcagggtctg ctgctgaaaa ttctgcaccg tctggttggt   9120
tataccagca tttgggaacg tgatctgcgt tttcgcctga aggtgaatt  tcctgaaaac   9180 cactatatcg aggaaatttt caactttgac aacagcaaaa acgtgaaata  taagagcggt   9240
cagatcgtcg aaaagtacat caacttttac aaagaacttt acaaggataa tgtggaaaaa   9300
cgcagcatct acagcgacaa gaaagtgaaa aagctgaagc aagaaaagaa agacctgtac   9360
atccgtaatt atatcgccca ctttaactat atcccgcatg cagaaattag tctgctggaa   9420
gttctggaaa atctgcgtaa actgctgtca tatgatcgca aactgaagaa cgcaatcatg   9480
aaaagcattg tggatatcct gaaagagtat ggttttgtcg ccacctttaa aatcggtgcc   9540
gataagaaaa ttgagattca gaccctggaa agcgagaaaa ttgtgcatct taagaaccttt  9600 aaaaagaaaa aactgatgac cgatcgcaac agcgaagagt tatgtgaact ggtgaaagtg   9660
atgttcgaat acaaagcact ggaagatccg aattcgagct ccgtcgacaa gcttgcggcc   9720
gcactcgagc accaccacca ccaccactga gatccggctg ctaacaaagc ccgaaaggaa   9780
gctgagttgg ctgctgccac cgctgagcaa taactagcat aacccctttgg ggcctctaaa  9840 cgggtcttga ggggtttttt gctgaaagga ggaactatat ccggat   9886
```

<210> SEQ ID NO 42
<211> LENGTH: 8731
<212> TYPE: DNA
<213> ORGANISM: Artificial Sequence
<220> FEATURE:
<223> OTHER INFORMATION: Synthetic

<400> SEQUENCE: 42

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120 cttttctcgcc acgttcgccg gctttccccg tcaagctcta aatcgggggc tccctttagg   180
gttccgattt agtgctttac ggcacctcga ccccaaaaaa cttgattagg gtgatggttc   240
acgtagtggg ccatcgccct gatagacggt ttttcgccct tgacgttgg  agtccacgtt   300 ctttaatagt ggactcttgt tccaaactgg aacaacactc aaccctatct cggtctattc   360
ttttgattta aagggatttt tgccgatttc ggcctattgg ttaaaaaatg agctgattta   420
acaaaaattt aacgcgaatt ttaacaaaat attaacgttt acaatttcag gtggcacttt   480
tcggggaaat gtgcgcggaa cccctatttg tttattttc  taaatacatt caaatatgta   540
tccgctcatg aattaattct tagaaaaact catcgagcat caaatgaaac tgcaatttat   600
tcatatcagg attatcaata ccatatttt  gaaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttcttttcc  840 agacttgttc aacaggccag ccattacgct cgtcatcaaa atcactcgca tcaaccaaac   900
```

```
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200
ctttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa atcccttaa      1440 cgtgagtttt cgttccactg agcgtcagac cccgtagaaa agatcaaagg atcttcttga     1500
gatccttttt ttctgcgcgt aatctgctgc ttgcaaacaa aaaaaccacc gctaccagcg     1560
gtggtttgtt tgccggatca agagctacca actctttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc gaagggagaa     1920
aaggcggaca ggtatccggt aagcggcagg gtcggaacag gagagcgcac gagggagctt     1980 ccaggggaa acgcctggta tctttatagt cctgtcgggt ttcgccacct ctgacttgag      2040
cgtcgatttt tgtgatgctc gtcagggggg cggagcctat ggaaaaacgc cagcaacgcg     2100 gccttttac ggttcctggc cttttgctgg ccttttgctc acatgttctt tcctgcgtta      2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt ttcctgtttt     2700
ggtcactgat gcctccgtgt aagggggatt tctgttcatg ggggtaatga taccgatgaa     2760
acgagagagg atgctcacga tacgggttac tgatgatgaa catgcccggt tactggaacg     2820
ttgtgagggt aaacaactgg cggtatggat gcggcgggac cagagaaaaa tcactcaggg     2880
tcaatgccag cgcttcgtta atacagatgt aggtgttcca cagggtagcc agcagcatcc     2940
tgcgatgcag atccggaaca taatggtgca gggcgctgac ttccgcgttt ccagacttta     3000
cgaaacacgg aaaccgaaga ccattcatgt tgttgctcag gtcgcagacg ttttgcagca     3060
gcagtcgctt cacgttcgct cgcgtatcgg tgattcattc tgctaaccag taaggcaacc     3120
ccgccagcct agccgggtcc tcaacgacag gagcacgatc atgcgcaccc gtggggccgc     3180
catgccggcg ataatggcct gcttctcgcc gaaacgtttg gtggcgggac cagtgacgaa     3240
ggcttgagcg agggcgtgca agattccgaa taccgcaagc gacaggccga tcatcgtcgc     3300
```

```
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat tgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgaaagtga ccaaagtgga tggcatcagc    5100
cacaaaaaat acatcgaaga aggcaaactg gttaaagca ccagcgaaga aaatcgtacc    5160
agcgaacgtc tgagcgaact gctgagcatt cgtctggata tctatatcaa aaatccggat    5220
aatgccagcg aggaagaaaa ccgtattcgt cgtgaaaacc tgaaaaagtt cttcagcaat    5280
aaagtgctgc acctgaaaga tagcgttctg tatctgaaaa accgcaaaga aaaaaatgcc    5340
gtgcaggaca aaaactatag cgaagaggat atcagcgagt atgacctgaa gaacaaaaat    5400
agctttagcg tgctgaaaaa aatcctgctg aatgaagatg tgaatagcga ggaactggaa    5460
atctttcgta agatgttga agccaagctg aacaaaatca acagcctgaa atatagcttt    5520
gaagaaaaca aggccaacta tcagaaaatc aacgagaaca acgtgaaaaa agttggtggt    5580
aaaagcaaac gcaacatcat ctatgattat tatcgcgaaa gcgcgaaacg caacgattat    5640
```

```
atcaataatg tgcaagaggc cttcgacaaa ctgtacaaaa agaggacat cgaaaaactg      5700 ttttttctga tcgagaacag caagaagcac gagaaataca aaatccgcga gtactaccat      5760
aaaatcatcg gtcgcaaaaa cgataaagag aacttcgcca aaatcatcta cgaagaaatt      5820
cagaacgtga acaacatcaa agaactgatc gaaaaaattc cggacatgag cgagctgaag      5880
aaaagccagg tgttctataa atactacctg acaaagagg aactgaacga caaaaacatc      5940
aaatatgcct tttgccactt cgtcgaaatt gaaatgagcc agctgcttaa aaactacgtg      6000
tataaacgcc tgagcaacat cagcaacgat aaaatcaaac gtatctttga atatcagaat      6060
ctgaagaaac tgattgaaaa caaactgctg aacaagctgg ataccatgt tcgtaattgc      6120 ggcaaataca actactatct gcaggttggt gaaattgcaa ccagcgattt tattgcacgt      6180
aatcgtcaga atgaagcctt tctgcgtaac attattggtg ttagcagcgt tgcatatttt      6240
agcctgcgta atattctgga aaccgaaaac gaaatgata ttaccggtcg tatgcgtggt      6300
aaaaccgtta aaacaataa aggcgaagag aagtatgtga gcggtgaagt ggataaaatc      6360
tataacgaaa acaagcagaa cgaagtgaaa gaaaatctga aatgttttta cagctacgac      6420
ttcaacatgg acaacaaaaa cgagatcgaa gatttcttcg ccaacattga tgaagccatt      6480
agcagtattc gtcatggcat tgtgcacttt aatctggaac ttgaaggcaa agacatcttc      6540
gcgtttaaaa acattgcacc gagcgagatc agcaaaaaaa tgtttcagaa cgagattaac      6600 gaaaaaaac tgaaactgaa aatcttcaaa cagctgaata gcgccaacgt gttcaactat      6660
tatgagaaag acgtgatcat caaataccct aaaaacacca aattcaactt cgtgaataaa      6720
aacatcccgt tgttccgag cttcaccaaa ctgtataaca aaattgaaga tctgcgcaat      6780
accctgaagt tttttttggag cgttccgaaa gacaagaag aaaaagacgc acagatctac      6840
ctgcttaaga acatctatta tggcgaattt ctgaacaaat tcgtgaaaaa tagcaaagtg      6900
ttcttcaaaa tcaccaacga ggtgatcaag attaacaaac agcgtaatca gaaaaccggt      6960 cactacaat accagaagtt tgagaacatt gaaaaaaccg tgccggttga atatctggca      7020
attattcaga gccgtgagat gattaacaac caggataaag aagagaaaaa cacctacatc      7080
gatttcatcc agcagatctt tctgaaaggc tttatcgatt accctgaacaa gaacaacctg      7140 aagtatatcg agtcgaacaa caataacgac aacaacgaca tcttagcaa aatcaaaatc      7200 aagaaagata taaagaaaa atacgacaag atccctgaaaa actatgagaa gcacaaccgc      7260
aacaaagaaa ttccgcatga gatcaatgaa tttgtgcgcg aaattaaact gggcaaaatc      7320
ctgaaataca ccgagaaacct gaatatgttc tatctgattc tgaagctgct gaaccataaa      7380
gagctgacca atctgaaagg tagcctggaa aaatatcaga gcgcaaacaa agaagagaca      7440
ttttctgacg aactggaact gattaatctg ctgaatctgg ataataaccg tgtgaccgaa      7500 gatttgaac tggaagcaaa tgaaatcggc aaattcctgg atttcaatga aacaaaatt      7560 aaggaccgga aagagcttaa aaagtttgat accaacaaaa tctacttcga cggcgagaac      7620
attatcaaac atcgtgcctt ttataacatc aaaaagtatg gcatgctgaa cctgctggaa      7680
aaaattgcag ataaagccaa gtacaaaatt agcctgaaag aacttaaaga gtacagcaac      7740
aaaaagaacg aaatcgagaa gaactatacc atgcagcaga tctgcatcg taaatatgca      7800 cgtccgaaaa aagacgagaa attcaacgat gaggactata agaatacga gaaagccatt      7860 ggcaacatcc agaaatatac ccacttgaaa aacaaagtgg aatttaacga gctgaattta      7920
ctgcagggtc tgctgctgaa aattctgcac cgtctggttg ttataccag catttgggaa      7980 cgtgatctgc gttttcgcct gaaaggtgaa tttcctgaaa accactatat cgaggaaatt      8040
```

| | |
|---|---|
| ttcaactttg acaacagcaa aaacgtgaaa tataagagcg gtcagatcgt cgaaaagtac | 8100 |
| atcaactttt acaagaaact ttacaaggat aatgtggaaa aacgcagcat ctacagcgac | 8160 |
| aagaaagtga aaaagctgaa gcaagaaaag aaagacctgt acatccgtaa ttatatcgcc | 8220 |
| cactttaact atatcccgca tgcagaaatt agtctgctgg aagttctgga aaatctgcgt | 8280 |
| aaactgctgt catatgatcg caaactgaag aacgcaatca tgaaaagcat tgtggatatc | 8340 |
| ctgaaagagt atggttttgt cgccaccttt aaaatcggtg ccgataagaa aattgagatt | 8400 |
| cagaccctgg aaagcgagaa aattgtgcat cttaagaacc ttaaaaagaa aaaactgatg | 8460 |
| accgatcgca acagcgaaga gttatgtgaa ctggtgaaag tgatgttcga atacaaagca | 8520 |
| ctggaagggg atccgaattc gagctccgtc gacaagcttg cggccgcact cgagcaccac | 8580 |
| caccaccacc actgagatcc ggctgctaac aaagcccgaa aggaagctga gttggctgct | 8640 |
| gccaccgctg agcaataact agcataaccc cttggggcct ctaaacgggt cttgaggggt | 8700 |
| tttttgctga aggaggaac tatatccgga t | 8731 |

<210> SEQ ID NO 43
<211> LENGTH: 5206
<212> TYPE: DNA
<213> ORGANISM: Artificial Sequence
<220> FEATURE:
<223> OTHER INFORMATION: Synthetic

<400> SEQUENCE: 43

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta agggattt tgccgatttc ggcctattgg ttaaaaaatg agctgattta | 420 |
| acaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg aattaattct tagaaaaact catcgagcat caaatgaaac tgcaatttat | 600 |
| tcatatcagg attatcaata ccatattttt gaaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga cgaaatac gcgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |

-continued

```
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc     1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctaacggg gggttcgtgc acacagccca gcttggagcg aacgacctac     1860
accgaactga gatacctaca gcgtgagcta tgagaaagcg ccacgcttcc gaagggagga    1920
aaggcggaca ggtatccggt aagcggcagg gtcggaacag gagagcgcac gagggagctt    1980
ccaggggggaa acgcctggta tctttatagt cctgtcgggt ttcgccacct ctgacttgag   2040
cgtcgatttt tgtgatgctc gtcagggggg cggagcctat ggaaaaacgc cagcaacgcg    2100
gcctttttac ggttcctggc cttttgctgg ccttttgctc acatgttctt cctgcgtta     2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac accgctgac gcgccctgac gggcttgtct     2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aaggggggatt tctgttcatg ggggtaatga taccgatgaa   2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
```

```
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccacttttt tcccgcgttt    4500
tcgcagaaac gtggctggcc tggttcacca cgcggggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatatacc gatccggctg ctaacaaagc ccgaaaggaa    5100
gctgagttgg ctgctgccac cgctgagcaa taactagcat aaccccttgg ggcctctaaa    5160
cgggtcttga ggggttttt gctgaaagga ggaactatat ccggat                    5206
```

<210> SEQ ID NO 44
<211> LENGTH: 6367
<212> TYPE: DNA
<213> ORGANISM: Artificial Sequence
<220> FEATURE:
<223> OTHER INFORMATION: Synthetic

<400> SEQUENCE: 44

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
```

```
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500 gatcctttt tttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
```

```
tgcgatgcag atccggaaca taatggtgca gggcgctgac ttccgcgttt ccagactttta  3000 cgaaacacgg aaaccgaaga ccattcatgt tgttgctcag gtcgcagacg ttttgcagca  3060
gcagtcgctt cacgttcgct cgcgtatcgg tgattcattc tgctaaccag taaggcaacc  3120
ccgccagcct agccgggtcc tcaacgacag gagcacgatc atgcgcaccc gtggggccgc  3180
catgccggcg ataatggcct gcttctcgcc gaaacgtttg gtggcgggac cagtgacgaa  3240
ggcttgagcg agggcgtgca agattccgaa taccgcaagc gacaggccga tcatcgtcgc  3300
gctccagcga aagcggtcct cgccgaaaat gacccagagc gctgccggca cctgtcctac  3360
gagttgcatg ataaagaaga cagtcataag tgcggcgacg atagtcatgc cccgcgccca  3420
ccggaaggag ctgactgggt tgaaggctct caagggcatc ggtcgagatc ccggtgccta  3480
atgagtgagc taacttacat taattgcgtt gcgctcactg cccgctttcc agtcgggaaa  3540
cctgtcgtgc cagctgcatt aatgaatcgg ccaacgcgcg gggagaggcg gtttgcgtat  3600
tgggcgccag gtggtttttt cttttcacca gtgagacggg caacagctga ttgcccttca  3660
ccgcctggcc ctgagagagt tgcagcaagc ggtccacgct ggtttgcccc agcaggcgaa  3720
aatcctgttt gatggtggtt aacggcggga tataacatga gctgtcttcg gtatcgtcgt  3780
atcccactac cgagatatcc gcaccaacgc gcagcccgga ctcggtaatg gcgcgcattg  3840
cgcccagcgc catctgatcg ttggcaacca gcatcgcagt gggaacgatg ccctcattca  3900
gcatttgcat ggtttgttga aaaccggaca tggcactcca gtcgccttcc cgttccgcta  3960
tcggctgaat ttgattgcga gtgagatatt tatgccagcc agccagacgc agacgcgccg  4020
agacagaact taatgggccc gctaacagcg cgatttgctg gtgacccaat gcgaccagat  4080
gctccacgcc cagtcgcgta ccgtcttcat gggagaaaat aatactgttg atgggtgtct  4140
ggtcagagac atcaagaaat aacgccggaa cattagtgca ggcagcttcc acagcaatgg  4200
catcctggtc atccagcgga tagttaatga tcagcccact gacgcgttgc gcgagaagat  4260
tgtgcaccgc cgctttacag gcttcgacgc cgcttcgttc taccatcgac accaccacgc  4320
tggcacccag ttgatcggcg cgagatttaa tcgccgcgac aatttgcgac ggcgcgtgca  4380
gggccagact ggaggtggca acgccaatca gcaacgactg tttgcccgcc agttgttgtg  4440
ccacgcggtt gggaatgtaa ttcagctccg ccatcgccgc ttccactttt tcccgcgttt  4500
tcgcagaaac gtggctggcc tggttcacca cgcgggaaac ggtctgataa gagacaccgg  4560
catactctgc gacatcgtat aacgttactg gtttcacatt caccaccctg aattgactct  4620
cttccgggcg ctatcatgcc ataccgcgaa aggttttgcg ccattcgatg gtgtccggga  4680
tctcgacgct ctcccttatg cgactcctgc attaggaagc agcccagtag taggttgagg  4740
ccgttgagca ccgccgccgc aaggaatggt gcatgcaagg agatggcgcc caacagtccc  4800
ccggccacgg ggcctgccac catacccacg ccgaaacaag cgctcatgag cccgaagtgg  4860
cgagcccgat cttccccatc ggtgatgtcg gcgatatagg cgccagcaac cgcacctgtg  4920
gcgccggtga tgccggccac gatgcgtccg cgtagagga tcgagatctc gatcccgcga  4980
aattaatacg actcactata ggggaattgt gagcggataa caattcccct ctagaaataa  5040
ttttgtttaa cttaagaag gagatatacc atgaaaatcg aagaaggtaa actggtaatc  5100
tggattaacg gcgataaagg ctataacggt ctcgctgaag tcggtaagaa attcgagaaa  5160
gataccggaa ttaaagtcac cgttgagcat ccggataaac tggaagagaa attcccacag  5220
gttgcggcaa ctggcgatgg ccctgacatt atcttctggg cacacgaccg ctttggtggc  5280
```

```
tacgctcaat ctggcctgtt ggctgaaatc accccggaca aagcgttcca ggacaagctg    5340
tatccgttta cctgggatgc cgtacgttac aacggcaagc tgattgctta cccgatcgct    5400
gttgaagcgt tatcgctgat ttataacaaa gatctgctgc cgaacccgcc aaaaacctgg    5460
gaagagatcc cggcgctgga taaagaactg aaagcgaaag gtaagagcgc gctgatgttc    5520
aacctgcaag aaccgtactt cacctggccg ctgattgctg ctgacggggg ttatgcgttc    5580
aagtatgaaa acggcaagta cgacattaaa gacgtgggcg tggataacgc tggcgcgaaa    5640
gcgggtctga ccttcctggt tgacctgatt aaaaacaaac acatgaatgc agacaccgat    5700
tactccatcg cagaagctgc ctttaataaa ggcgaaacag cgatgaccat caacggcccg    5760
tgggcatggt ccaacatcga caccagcaaa gtgaattatg gtgtaacggt actgccgacc    5820
ttcaagggtc aaccatccaa accgttcgtt ggcgtgctga gcgcaggtat taacgccgcc    5880
agtccgaaca aagagctggc aaaagagttc ctcgaaaact atctgctgac tgatgaaggt    5940
ctggaagcgg ttaataaaga caaaccgctg ggtgccgtag cgctgaagtc ttacgaggaa    6000
gagttggtga aagatccgcg tattgccgcc actatggaaa acgcccagaa aggtgaaatc    6060
atgccgaaca tcccgcagat gtccgctttc tggtatgccg tgcgtactgc ggtgatcaac    6120
gccgccagcg gtcgtcagac tgtcgatgaa gccctgaaag acgcgcagac taattcgagc    6180
tcgaacaaca acaacaataa caataacaac aacctcggga tcgagggaag ggatccggct    6240
gctaacaaag cccgaaagga agctgagttg gctgctgcca ccgctgagca ataactagca    6300
taaccccttg gggcctctaa acgggtcttg aggggttttt tgctgaaagg aggaactata    6360
tccggat                                                              6367
```

What is claimed:

1. A method for expressing and purifying a Cas13a protein, the method comprising:
   (a) inserting a nucleotide sequence encoding a polypeptide having the polypeptide sequences of SEQ ID NO: 10 into an expression plasmid;
   (b) transforming one or more cells with the expression plasmid;
   (c) inducing expression of the transformed plasmid;
   (d) isolating the cells;
   (e) extracting the Cas13a protein; and
   (f) purifying the protein using affinity purification and ion exchange purification.

2. The method of claim 1, wherein the cell comprises *E. coli* BL21(DE3).

3. The method of claim 1, wherein the expression plasmid comprises pET28 or pET28-MBP-TEV plasmids.

4. The method of claim 1, wherein the nucleotide sequence is inserted into the expression plasmid using isothermal assembly.

5. The method of claim 1, wherein the affinity purification comprises a nickel or a maltose affinity media.

6. The method of claim 1, wherein the affinity purification comprises affinity chromatography comprising:
   (f1) a equilibrating a nickel affinity column with a binding buffer and loading the extracted Cas13a protein;
   f(2) washing the nickel affinity column with a wash buffer; and
   f(3) eluting the affinity purified Cas13a protein from the nickel affinity column using elution buffer.

7. The method of claim 1, wherein the affinity purification comprises affinity chromatography comprising:
   f(1) equilibrating a maltose affinity column with a binding buffer and loading the extracted Cas13a protein;
   f(2) washing the maltose affinity column with a wash buffer; and
   f(3) eluting the affinity purified Cas13a protein from the maltose affinity column using elution buffer.

8. The method of claim 1, wherein the ion exchange purification comprises a cation exchange media.

9. The method of claim 1, wherein the ion exchange purification comprises cation exchange chromatography comprising:
   (1) equilibrating a cation exchange column with a binding buffer and loading the extracted Cas13a protein;
   (2) washing the cation exchange column with a wash buffer; and
   (3) eluting the cation exchange purified Cas13a protein from the cation exchange column using an elution buffer.

10. The method of claim 1, further comprising concentrating the purified Cas13a protein to approximately 10 mg/mL.

11. The method of claim 10, further comprising dialyzing the concentrated purified Cas13a protein.

12. A method for purifying a recombinant Cas13a protein, the method comprising:
   (a) providing an expressed recombinant Cas13a protein having the polypeptide sequence of SEQ ID NO: 10;
   (b) performing an affinity purification comprising a nickel affinity media or a maltose affinity media;
   (c) performing an ion exchange purification comprising a cation exchange media; and
   (d) collecting the purified Cas13a protein.

13. The method of claim 12, further comprising concentrating the purified Cas13a protein to approximately 10 mg/mL.

14. The method of claim 13, further comprising dialyzing the concentrated purified Cas13a protein against three rounds of dialysis buffer.

* * * * *